United States Patent [19]
Collins et al.

[11] Patent Number: 5,859,195
[45] Date of Patent: Jan. 12, 1999

[54] NEUROFIBROMATOSIS GENE

[75] Inventors: Francis S. Collins; Margaret R. Wallace; Douglas A. Marchuk; Lone B. Andersen; David H. Gutmann, all of Ann Arbor, Mich.

[73] Assignee: The Regents of the University of Michigan, Ann Arbor, Mich.

[21] Appl. No.: 449,933

[22] Filed: May 25, 1995

Related U.S. Application Data

[60] Division of Ser. No. 966,049, filed as PCT/US94/04624 Jun. 28, 1991, which is a continuation-in-part of Ser. No. 547,090, Jun. 29, 1990, abandoned.

[51] Int. Cl.$^6$ ............... C07K 14/435; C07H 21/04
[52] U.S. Cl. ............... 530/350; 536/23.5; 536/24.31; 435/69.1; 530/828; 935/9
[58] Field of Search ............... 530/350, 828; 435/69.1; 536/23.5, 23.1, 24.31; 935/9

[56] References Cited

U.S. PATENT DOCUMENTS

| 5,227,292 | 7/1993 | White et al. | 435/69.1 |
| 5,532,351 | 7/1996 | Stefansson | 536/23.1 |
| 5,578,462 | 11/1996 | Seizinger et al. | 435/69.1 |
| 5,580,955 | 12/1996 | Nur-E-Kamal et al. | 530/324 |

OTHER PUBLICATIONS

Ruddle, Frank H. "The William Allan Memorial Award Address: Reverse Genetics and Beyond" *Am. J. Hum. Genes* 36:944–53 (1984).

Sevier et al. "Monoclonal Antibodies in Clinical Immunology" (1981) *J. Clin. Chem.* 27(11):1797–1806.

Buchberg, A.M. et al., "Localization of Evi–2 to Chromosome 11: Linkage to Other Proto–oncogene and Growth Factor Loci Using Interspecific Backcross Mice", *Oncogene Research* 2: 149–165 (1988).

Call, K.M. et al., "Isolation and Characterization of a Zinc Finger Polypeptide Gene at the Human Chromosome 11 Wilms' Tumor Locus", *Cell* 60:509–520 (1990).

Cohen, M.M., "Invited Historical Comment: Further Diagnostic Thoughts About the Elephant Man", *Am. J. Med. Gent.* 29:777–782 (1988).

Collins, F.S. et al., "Editorial: The von Recklinghausen Neurofibromatosis Region on Chromosome 17–Genetic and Physical Maps Come into Focus", *Am. J. Hum. Genet.* 44:1–5 (1989).

Collins, F.S. et al., "Progress Towards Identifying the Neurofibromatosis (NF1) Gene", *Trends in Genetics* 5:217–221 (1989).

Diehl, S.R. et al., "A Refined Genetic Map of the Region of Chromosome 17 Surrounding the von Recklinghausen Neurofibromatosis (NF1) Gene", *Am. J. Hum. Genet.* 44:33–37 (1989).

Fain, P.R. et al., "The Order of Loci in the Pericentric Region of Chromosome 17, Based on Evidence from Physical and Genetic Breakpoints", *Am. J. Hum. Genet.* 44:68–72 (1989).

Gessler, M. et al., "Homozygous Deletion in Wilms Tumours of a Zinc–finger Gene Identified by Chromosome Jumping", *Nature* 343:774–778 (1990).

Goldgar, D.E. et al., "Multipoint Linkage Analysis in Neurofibromatosis Type 1: An International Collaboration", *Am. J. Hum. Genet.* 44:6–12 (1989).

Hadfield, C., "Chromosome Walking", *Focus* vol. 5 No. 4:1–5 (1983).

(List continued on next page.)

*Primary Examiner*—Carla J. Myers
*Attorney, Agent, or Firm*—Morrison & Foerster LLP

[57] ABSTRACT

The entire coding region of the gene involved in von Recklinghausen neurofibromatosis (NF1) and a ubiquitously expressed large transcript (NF1LT) of the gene have been identified, cloned and sequenced. With the identification of the NF1 gene and its gene product, nucleic acid probes and antibodies raised to the gene product can be used in a variety of hybridization and immunological assays to screen for NF1 and detect it in its early stages. Conventional and gene therapies can also be developed to treat those afflicted with the disease.

18 Claims, 29 Drawing Sheets

OTHER PUBLICATIONS

Kittur, S.D. et al., "Linkage Analysis of Neurofibromatosis Type 1, Using Chromosome 17 DNA Markers", *Am. J. Hum. Genet.* 44:48–50 (1989).

Kyte, J. et al., "A Simple Method for Displaying the Hydropathic Character of a Protein", *J. Mol. Biol.* 157:105–132 (1982).

Ledbetter, D.H. et al., "Precise Localization of NF1 to 17q11.2 by Balanced Translocation", *Am. J. Hum. Genet.* 44:20–24 (1989).

Matthew, C.G.P. et al., "Linkage Analysis of Chromosome 17 Markers in British and South African Families with Neurofibromatosis Type 1", *Am. J. Hum. Genet.* 44:38–40 (1989).

Menon, A.G. et al., "Characterization of a Translocation within the von Recklinghausen Neurofibromatosis Region of Chromosome 17", *Genomics* 5:245–249 (1989).

O'Connell, P. et al., "Fine Structure DNA Mapping Studies of the Chromosomal Region Harboring the Genetic Defect in Neurofibromatosis Type 1", *Am. J. Hum. Genet.* 44:51–57 (1989).

Schmidt, M.A. et al., "Cases of Neurofibromatosis with Rearrangements of Chromosome 17 in Band 17q11.2", *Am. J. Med. Genet.* 28:771–777 (1987).

Seizinger, B.R. et al., "Genetic Linkage of von Recklinghausen Neurofibromatosis to the Nerve Growth Factor Receptor Gene", *Cell* 49:589–594 (1987).

Seizinger, B.R. et al., "Flanking Markers for the Gene Causing von Recklinghausen Neurobiromatosis (NF1)", *Am. J. Hum. Genet.* 44:30–32 (1989).

Stephens, K. et al., "Genetic Analysis of Eight Loci Tightly Linked to Neurofibromatosis 1", *Am. J. Hum. Genet.* 44:13–19 (1989).

Upadhyaya, M. et al., "Close Flanking Markers for Neurofibromatosis Type 1 (NF1)", *Am. J. Hum. Genet.* 44:41–47 (1989).

vanTuinen, P. et al., "Regional Mapping Panel for Human Chromosome 17 Application to Neurofibromatosis Type 1", *Genomics* 1:374–381 (1987).

Vance, J.M. et al., "Genetic Linkage Mapping Chromosome 17 Markers and Neurofibromatosis Type 1", *Am. J. Hum. Genet.* 44:25–29 (1989).

Wallace, R.W. et al., "Type 1 Neurofibromatosis Gene: Identification of a Large Transcript Disrupted in Three NFI Patients", *Science* 249:181–186 (1990).

Xu, G. et al., "The Neurofibromatosis Type 1 Gene Encodes a Protein Related to GAP", *Cell* 62:599–608 (1990).

Adari, H. et al., "Guanosine Triphosphatase Activating Protein (GAP) Interacts with the p21 ras Effector Binding Domain", *Science* 240:518–521 (1988).

Andersen, L.B. et al., "Formation of a Minichromosome by Excision of the Proximal Region of 17q in a Patient with von Recklinghausen Neurofibromatosis", *Cytogenet. Cell Genet.* 53:206–210 (1990).

Ballester, R. et al., "The NF1 Locus Encodes a Protein Functionally Related to Mammalian GAP and Yeast IRA Proteins", *Cell* 63:851–859 (1990).

Bar–Sagi, D. et al., "Microinjection of the ras Oncogene Protein into PC12 Cells Induces Morphological Differentiation", *Cell* 42:841–848 (1985).

Benton, W.D. et al., "Screening λgt Recombinant Clones by Hybridization to Single Plaques in situ", *Science* 196:180–182 (1977).

Boorstein, W.R. et al., In "Methods in Enzymology" (J.E. Dahlberg and J.N. Abelson, Eds.), vol. 180, pp. 347–369, *Academic Press,* San Diego (1989).

Boulton, T.G. et al., "ERKs: A Family of Protein–Serine/Threonine Kinases that are Activated and Tyrosine Phosphorylated in Response to Insulin and NGF", *Cell* 65:663–675 (1991).

Buchberg, A. et al., "Sequence Homology Shared by Neurofibromatosis Type 1 Gene and IRA–1 and IRA–2 Negative Regulators of the RAS Cyclic AMP Pathway", *Nature* 347:291–294 (1990).

Cales, C. et al., "The Cytoplasmic Protein GAP is Implicated as the Target for Regulation by the ras Gene Product", *Nature* 332:548–551 (1988).

Carey, T.E. et al., "Cell Surface Antigens of Human Malignant Melanoma: Mixed Hemadsorption Assays for Humoral Immunity to Cultured Autologous Melanoma Cells", *Proc. Natl. Acad. Sci. U.S.A.* 73:3278–3282 (1976).

Cawthon, R. et al., "A Major Segment of the Neurofibromatosis Type 1 Gene: cDNA Sequence, Genomic Structure, and Point Mutations", *Cell* 62:193–201 (1990).

Cawthon, R. et al., "Identification and Characterization of Transcripts from the Neurofibromatosis 1 Region: The Sequence and Genomic Structure of EVI2 and Mapping of Other Transcripts", *Genomics* 7:555–565 (1990).

Cawthon, R.M. et al., "cDNA Sequence and Genomics Structure of EVI2B, a Gene Lying with an Intron of the Neurofibromatosis Type 1 Gene", *Genomics* 9:446–460 (1991).

DeClue, J.E. et al., "A ras Effector Domain Mutant which is Temperature Sensitive for Cellular Transformation: Interactions with GTPase–Activating Protein and NF–1", *Mol. Cell, Biol.* 11:3132–3138 (1991).

Diekmann, D. et al., "Bcr Encodes a GTPase–activating Protein for p21$^{rac}$", *Nature* 351:400–402 (1991).

Fountain, J.W. et al., "Physical Mapping of the von Recklinghausen Neurofibromatosis Region on Chromosome 17", *Amer. J. Hum. Genet.* 44:58–67 (1989).

Ginsburg, D. et al., "Human von Willebrand Factor (vWF): Isolation of Complementary DNA (cDNA) Clones and Chromosomal Localization", *Science* 228:1401–1406 (1985).

Glover, T.W. et al., "Molecular and Cytogenetic Analysis of Tumors in von Recklinghausen Neurofibromatosis", *Genes, Chrom. Cancer* 3:62–70 (1991).

Hagag, N. et al., "Inhibition of Growth Factor–Induced Differentiation of PC12 Cells by Microinjection of Antibody to ras p21", *Nature* 319:680–682 (1986).

Hall, A. "ras and Gap–Who's Controlling Whom?", *Cell* 61:921–923 (1990).

Jadayel, D. et al. "Patenal Origin of New Mutations in von Recklinghausen Neurofibromatosis", *Nature* 343:558–559 (1990).

Klein, P. et al., "The Detection and Classification of Membrane–Spanning Proteins", *Biochem. Biophys. Acta* 815:468–476 (1985).

Knudson, A.G., "Hereditary Cancer, Oncogenes, and Antioncogenes", *Caner Res.* 45:1437–1443 (1985).

Koch, C.A. et al., "SH2 and SH3 Domains: Elements that Control Interations of Cytoplasmic Signaling Proteins", *Science* 252:668–674 (1991).

Koenig, M. et al., "Complete Cloning of the Duchenne Muscular Dystrophy (DMD) cDNA and Preliminary Genomic Organization of the DMD Gene in Normal and Affected Individuals", *Cell* 50:509–517 (1987).

Kozak, M., "Point Mutations Define a Sequence Flanking the AUG Initiator Codon that Modulates Translation by Eukaryotic Ribosomes", *Cell* 44:283–292 (1986).

Martin, G.A. et al., "The GAP–Related Domain of the Neurofibromatosis Type 1 Gene Product Interacts with ras p21", *Cell* 63:843–849 (1990).

Menon, A.G. et al., "Chromosome 17p Deletions and p53 Gene Mutations Associated with the Formation of Malignant Neurofibrosarcomas in von Recklinghausen Neurofibromatosis", *Proc. Natl. Acad. Sci. U.S.A.* 87:5435–5439 (1990).

Mikol, D.D. et al., "The Oligodendrocyte–Myelin Glycoprotein Belongs to a Distinct Family of Proteins and Contains the HNK–1 Carbohydrate", *J. Cell Biol.* 110:471–479 (1990).

Nigro, J.M. et al., "Mutations of the p53 Gene Occur in Diverse Human Tumour Types", *Nature* 342:705–708 (1989).

Noda, M. et al., "Sarcoma Viruses Carrying ras Oncogenes Induce Differentiation–Associated Properties in a Neuronal Cell Line", *Nature* 318:73–75 (1985).

O'Connel, P. et al., "The Human Homolog of Murine Evi–2 Lies Between Two von Recklinghausen Neurofibromatosis Translocations", *Genomics* 7:547–554 (1990).

Otsu, M. et al., "Characterization of Two 85 kd Proteins that Associate with Receptor Tyrosine Kinases, Middle–T/pp60$^{c-src}$ Complexes, and PI3–Kinase", *Cell* 65:91–104 (1991).

Ratner, N. et al., "Mitogen Accumulation in von Recklinghausen Neurofibromatosis", *Ann. Neurol.* 27:298–303 (1990).

Riccardi, V.M., "von Recklinghausen Neurofibromatosis", *New Engl. J. Med.* 305:1617–1626 (1981).

Riccardi, V.M. et al., Neurofibromatosis: Phenotype, Natural History, and Pathogenesis, Johns Hopkins University Press, Baltimore, MD, p. 305 (1986).

Riccardi, V.M. et al., "Penetrance of von Recklinghausen Neurofibromatosis: A Distinction Between Predecessors and Descendants", *Amer. J. Hum. Genet.* 42:284–289 (1988).

Ridley, A.J. et al., "ras–Mediated Cell Cycle Arrest is Altered by Nuclear Oncogenes to Induce Schwann Cell Transformation", *EMBO J.* 7:1635–1645 (1988).

Sharp, P.A., "Splicing of Messenger RNA Precursors", *Science* 235:766–771 (1987).

Sheela, S. et al., "Angiogenic and Invasive Properties of Neurofibroma Schwann Cells", *J. Cell Biol.* 111:645–653 (1990).

Skuse, G.R. et al., "Molecular Genetic Analysis of Tumors in von Recklinghausen Neurofibromatosis: Loss of Heterozygosity for Chromosome 17", *Cancer* 1:36–41 (1989).

Skuse, G.R., "Type 1 Neurofibromatosis Gene: Correction", *Science* 250:1749 (1990).

Stumpf, D.A. et al., *Neurofibromatosis, NIH Consensus Development Conference Statement*, vol. 6, No. 12 (1987).

Szeberenyi, J. et al., "Effect of a Dominant Inhibitory Ha–ras Mutation on Neuronal Differentiation of PC12 Cells", *Mol. Cell Biol.* 10:5324–5332 (1990).

Tanaka, K. et al., "IRA1, an Inhibitory Regulator of the RAS–Cyclic AMP Pathway in *Saccharomyces cerevisiae*", *Mol. Cell Biol.* 9:757–768 (1989).

Tanaka, K. et al., "*S. cerevisiae* Genes IRA1 and IRA2 Encode Proteins that may be Functionally Equivalent to Mammalian ras GTPase Activating Protein", *Cell* 60:803–807 (1990).

Tanaka, K. et al., "IRA2, a Second gene of *Saccharomyces cerevisiae* That Encodes a Protein with a Domain Homologous to Mammalian ras GTPase–Activating Protein", *Mol. Cell Biol.* 10:4303–4313 (1990).

Trahey, M. et al., "A Cytoplasmic Protein Stimulates Normal N–ras p21 GTPase, but Does Not Affect Oncogenic Mutants", *Science* 238:542–545 (1987).

Trahey, M. et al., "Molecular Cloning of Two Types of GAP Complementary DNA from Human Placenta", *Science* 242:1697–1700 (1988).

Viskochil, D. et al., "Deletions and a Translocation Interrupt a Cloned Gene at the Neurofibromatosis Type 1 Locus", *Cell* 62:187–192 (1990).

Viskochil, D. et al., "The Gene Encoding the Oligodendrocyte–Myelin Glycoprotein is Embedded within the Neurofibromatosis Type 1 Gene", *Mol. Cell Biol.* 11:906–912 (1991).

Vogel, U. et al., "Cloning of Bovine GAP and its Interaction with Oncogenic ras p21", *Nature* 335:90–93 (1988).

Wang, Y. et al., "Sar1, a Gene from *Schizosaccharomyces pombe* Encoding a Protein that Regulates ras1", *Cell Regulation* 2:453–465 (1991).

Xu, G. et al., "The Catalytic Domain of the Neurofibromatosis Type 1 Gene Product Stimulates ras GTPase and Complements ira Mutants of *S. cerevisiae*", *Cell* 63:835–841 (1990).

Yatani, A. et al., "ras p21 and GAP Inhibit Coupling a Muscarinic Receptors to Atrial K$^+$ Channels", *Cell* 61:769–776 (1990).

Adelman, J.P. et al., "Two Mammalian Genes Transcribed from Opposite Strands of the Same DNA Locus", *Science* 235:1514–1517 (1987).

Bader, J.L. et al., "Neurofibromatosis and Chilhood Leukemia", *J. Pediatr.* 92:925–929 (1978).

Baker, S.J. et al., "Chromosome 17 Deletions and p53 Gene Mutations in Colorectal Carcinomas", *Science* 244:217–221 (1989).

Barker, D. et al., "Gene for von Recklinghausen Neurofibromatosis is the Pericentromeric Region of Chromosome 17", *Science* 236:1100–1102 (1987).

Barker, W.C. et al., "Protein Sequence Database", *Meth. Enzyol.* 183:31–49 (1990).

Bird, A.P., "CpG–rich Islands and the Function of DNA Methylation", *Nature* 321:209–213 (1986).

Bonthron, D.T. et al., "Identification of a Point Mutation in the Adenosine Deaminase Gene Responsible for Immunodeficiency", *J. Clin. Invest.* 76:894–897 (1985).

Burke, D.T. et al., "Cloning of Large Segments of Exogenous DNA into Yeast by Means of Artificial Chromosome Vectors", *Science* 236:806–812 (1987).

Burks, C. et al., "GenBank: Current Status and Future Directions", *Methods Enzymol.* 183:3–22 (1990).

Chen, C.N. et al., "At Least Two Genes Reside Within a Large Intron of the Dunce Gene of Drosophila", *Nature* 329:721–724 (1987).

Crump, T., "Translation of Case Reports in Ueber die multiplen Fibrome der Haut und ihre Beziehung zu den multiplen Neuromen by F. v. Recklinghausen", *Adv. Neurol.* 29:259–275 (1981).

Dang, C.V. et al., "Nuclear and Nucleolar Targeting Sequences of c–erb–A, c–myb, N–mye, p53, HSP70, and HIV tat Proteins", *J. Biol. Chem.* 264:18019–18023 (1989).

Drumm, M.L. et al., "Physical Mapping of the Cystic Fibrosis Region by Pulsed–Field Gel Electrophoresis", *Genomics* 2:346–354 (1988).

Fearon, E.R. et al., "Identification of a Chromosome 18q Gene that is Altered in Colorectal Cancers", *Science*, 247:49–56 (1990).

Feinberg, A.P. et al., "A Technique for Radiolabeling DNA Restriction Endonulcease Fragments to High Specific Activity", *Anal. Biochem.* 137:266–267 (1984).

Fialkow, P.J. et al., "Multiple Cell Origin of Hereditary Neurofibromas", *N. Engl. J. Med.* 284:298–300 (1971).

Finlay, C.A. et al., "The p53 Proto–Oncogene Can Act as a Suppressor of Transformation", *Cell* 57:1083–1093 (1989).

Fountain, J.W. et al., "Physical Mapping of a Translocation Breakpoint in Neurofibromatosis", *Science* 244:1085–1086 (1989).

Friend, S.H. et al., "A Human DNA Segement with Properties of the Gene that Predisposes to Retinoblastoma and Osteosarcoma", *Nature*, 323:643–646 (1986).

Gibbs, R.A. et al., *Proc. Natl. Acad. Sci. U.S.A.* 86:1919–1923 (1989).

Ginsburg, D. et al., "Molecular Basis of Human von Willebrand Disease: Analysis of Platelet von Willebrand factor mRNA", *Proc. Natl. Acad. Sci. U.S.A.* 86:3723–3727 (1989).

Green, E.D. et al., "Systematic Screening of Yeast Artificial–Chromosome Libraries by use of the Polymerase Chain Reaction", *Proc. Natl. Acad. Sci. U.S.A.* 87:1213 (1990).

Henikoff, S. et al., "Gene within a Gene: Nested Drosophila Genes Encode Unrelated Proteins on Opposite DNA Strands", *Cell* 44:33–42 (1986).

Inotuye, M., "Antisense RNA: Its Functions and Applications in Gene Regulation", *Gene* 72:25–34 (1988).

Kahn, P. et al., "EMBL Data Library", *Meth. Enzymol.* 183:23–31 (1990).

Kerem, B.S. et al., "Identification of the Cystic Fiborsis Gene: Genetic Analysis", *Science* 245:1073–1080 (1989).

Lazar M.A, et al., "A Novel Member of the Thyroid/Steroid Hormone Receptor Family is Encoded by the Opposite Strand of the Rat c–erbAα Transcriptional Unit", *Mol., Cell Biol.* 9:1128–1136 (1989).

Levinson, B. et al., "A Transcribed Gene in an Intron of the Human Factor VIII Gene", *Genomics* 7:1–11 (1990).

Lindsay, S. et al., "Use of Restriction Enzymes to Detect Potential Gene Sequences in Mammalian DNA", *Nature* 327:336–338 (1987).

Marchuck, D. et al, "cDNA Cloning of the Type 1 Neurofibromatosis Gene: Complete Sequence of the NF1 Gene Product", *Genomics* 11:931–940 (1991).

McKeen, E.A. et al., "Rhabdomyosarcoma Complicating Multiple Neurofibromatosis", *J. Pediat.* 93:992–993 (1978).

Miyajima, N. et al., "Two erbA Homologs Encoding Proteins with Different $T_3$ Binding Capacities are Transcribed from Opposite DNA Strands of the Same Genetic Locus", *Cell* 57:31–39 (1989).

Monaco, A.P. et al., "Isolation of Candidate cDNAs for Portions of the Duchenne Muscular Dystrophy Gene", *Nature* 323:646–650 (1986).

Nakamura, Y. et al., "Variable Number of Tandem Repeat (VNTR) Markers for Human Gene Mapping", *Science* 235:1616–1622 (1987).

O'Connell, P. et al., "NF1 Translocations Map Within a 600–Kilobase Segment of 17q11.2", *Science* 244:1087–1088 (1989).

Orkin, S.H., "Reverse Genetics and Human Disease", *Cell* 47:845–850 (1986).

Riordan, J.R. et al., "Identification of the Cystic Fibrosis Gene: Cloning and Characterization of Complementary DNA", *Science* 245:1066–1072 (1989).

Rommens, J.M. et al., "Identification of the Cystic Fibrosis Gene: Chromosome Walking and Jumping", *Science* 245:1059–1065 (1989).

Royer–Pokora, B. et al., "Cloning the Gene for an Inherited Human Disorder–Chronic Granulomatous Disease–on the Basis of its Chromosomal Location", *Nature* 322:32–38 (1986).

Simons, R.W., "Naturally Occuring Antisense RNA Control", *Gene* 72:35–44 (1988).

Sorensen, S.A. et al., "Long–Term Follow–Up of von Recklinghausen Neurofibromatosis", *N.Engl, J. Med.* 314:1010–1015 (1986).

Wallace, M.R. et al., "Direct Construction of a Chromosome–specific Not1 Linking Library from Flow–Sorted Chromosome", *Nucleic Acids Res.* 17:1665–1677 (1989).

Wallace, M.R. et al., "A de novo Alu Insertion Results in Neurofibromatosis Type 1", *Nature* 353:864–866 (1991).

Weinberg, R.A., "The Rb Gene and the Negative Regulation of Cell Growth", *Blood* 74:529–532 (1989).

```
  1  ACAGAACTAGCTCAAAGATTTGCATTCCAATATAATCCATCCCTGCAACCAAGAGCTCTTGTTGTCTTTGGGTGTATTAGCAAACGAGTG
     T  E  L  A  Q  R  F  A  F  Q  Y  [N] P  S  L  Q  P  R  A  L  V  V  F  G  C  I  S  K  R  V

91  TCTCATGGGCAGATAAAGCAGATAATCCGTATTCTTAGCAAGGCACTTGAGAGTTGCTTAAAAGGACCTGACACTTACAACAGTCAAGTT
     S  H  G  Q  I  K  Q  D  N  P  Y  S  *  A  L  E  S  C  L  K  G  P  D  T  Y  N  S  Q  V

181  CTGATAGAAGCTACAGTAATAGCACTAACCAAATTACAGCCACTTCTTAATAGGACTCGCCTCTGCACAAAGCCCTCTTTGGGTAGCT
     L  I  E  A  T  V  I  A  L  T  K  L  Q  P  L  L  N  K  D  S  P  L  H  K  A  L  F  W  V  A

271  GTGGCTGTGCTGCAGCTTGATGAGGTCAACTTGTATTCAGCAGGTACCGCACTTCTTGAACAAAACCTGCATACTTTAGATAGTCTCCGT
     V  A  V  L  Q  L  D  E  V  N  L  Y  S  A  G  T  A  L  L  E  Q  N  L  H  T  L  D  S  L  R

361  ATATTCAATGACAAGAGTCCAGAGGAAGTATTTATGGCAATCCGGAATCCTCTGGAGTGGCACTGCAAGCAAATGGATCATTTTGTTGGA
     I  F  N  D  K  S  P  E  E  V  F  M  A  I  R  N  P  L  E  W  H  C  K  Q  M  D  H  F  V  G

451  CTCAATTTCAACTCTAACTTTGCATTGGTTGGACACCTTTTAAAAGGGTACAGGCATCCTCACCTGCTATTGTTGCAAGAACA
     L  N  F  N  S  N  F  A  L  V  G  H  L  L  K  G  Y  R  H  P  S  P  A  I  V  A  R  T

541  GTCAGAATTTTACATACAGTGTCTGAAGAAGTTCGAAGTCGCTGCAGCCTAAAACATAGAAAAGTCACTTCTTCTTACTGATATTTCAATGGAA
     V  R  I  L  H  T  L  L  T  L  V  N  K  H  R  N  C  D  K  F  E  V  N  T  Q  S  V  A  Y  L

631  GCAGCTTTACTTACAGTGTCTGAAGAAGTTCGAAGTCGCTGCAGCCTAAAACATAGAAAAGTCACTTCTTCTTACTGATATTTCAATGGAA
     A  A  L  L  T  V  S  E  E  V  R  S  R  C  S  L  K  H  R  K  S  L  L  L  T  D  I  S  M  E

721  AATGTTCCTATGGATACATATCCCATTCATCATGGTGATCCCAACTGTCGGGCCAGACCAGTCCCCGAGCCAGGAAATCCATGAGCCTGGGACATGGGGCAACCT
     N  V  P  M  D  T  Y  P  I  H  H  G  D  P  S  Y  R  T  L  K  E  T  Q  P  W  S  S  P  K  G

811  TCTGAAGGATACCTTGCAGCCACCTATCCCACTGTCGGGCCAGACCAGTCCCCGAGCCAGGAAATCCATGAGCCTGGGACATGGGGCAACCT
     S  E  G  Y  L  A  A  T  Y  P  T  V  G  Q  T  S  P  R  A  R  K  S  M  S  L  D  M  G  Q  P

901  TCTCAGGCCAACACTAAGAAGTTGCTTGGAACAAGGAAAAGTTTTGATCACTTGATATCAGACACAAAGGCTCCTAAAAAGGCAAGAAATG
     S  Q  A  N  T  K  K  L  L  G  T  R  K  S  F  D  H  L  I  S  D  T  K  A  P  K  R  Q  E  M
```

FIG. 6A

```
 991  GAATCAGGGATCACAACACCCCCAAAATGAGGAGAGTAGCAGAAACTGATTATGAAATGGAAACTCAGAGGATTCCTCATCACAACAG
      E  S  G  I  T  T  P  P  K  M  R  R  R  V  A  E  T  D  Y  E  M  E  T  Q  R  I  S  S  S  Q  Q
1081  CACCCACATTTACGTAAAGTTTCAGTGTCTGAATCAAATGTTCTCTTGGATGAAGAAGTACTTACTGATCCGAAGATCCAGGCGCTTCTT
      H  P  H  L  R  K  V  S  V  S  E  S  N  V  L  D  E  E  V  L  T  D  P  K  I  Q  A  L  L
1171  CTTACTGTTCTAGCTACACTGGTAAAATATACCACAGATGAGTTTGATCAACGAATTCTTTATGAATACTTAGCAGAGGCCAGTGTTGTG
      L  T  V  L  A  T  L  V  K  Y  T  T  D  E  F  D  Q  R  I  L  Y  E  Y  L  A  E  A  S  V  V
                                                A →
1261  TTTCCCAAAGTCTTTCCTGTTGTGCATAATTTGTTGGACTCTAAGATCAACACCCTGTTATCATTGTGCCAAGATCCAAATTTGTTAAAT
      F  P  K  V  F  P  V  V  H  N  L  L  D  S  K  I  N  T  L  L  S  L  C  Q  D  P  N  L  L  N
1351  CCAATCCATGGAATTGTGCAGAGTGTGGTGTACCATGAAGAATCCCCACCACAATACCAAACATCTTACCTGCAAAGTTTTGGTTTTAAT
      P  I  H  G  I  V  Q  S  V  V  Y  H  E  E  S  P  P  Q  Y  Q  T  S  Y  L  Q  S  F  G  F  N
1441  GGCTTGTGGCGGTTTGCAGGACCGTTTTCAAAGCAAACACAAATTCCAGACTATGCTGAGCTTATTGTTAAGTTTCTTGATGCCTTGATT
      G  L  W  R  F  A  G  P  F  S  K  Q  T  Q  I  P  D  Y  A  E  L  I  V  K  F  L  D  A  L  I
                  C →                                                                        B
1531  GACACGTACCTGCCTGGAATTGATGAAGAAACCAGTGAAGAATCCCTCCTTGACTCCCACATCTCCTTACCCTCCTGCACTGCAGAGCCAG
      D  T  Y  L  P  G  I  D  E  E  T  S  E  E  S  L  L  T  P  T  S  P  Y  P  P  A  L  Q  S  Q
1621  CTTAGTATCACTGCCAACCTTCACTTTCTAATTCCATGAACCTTCACTTGCAACTTCCCAGACATTCCCAGGATCGACAAGGAGAACGTT
      L  S  I  T  A  N  L  N  L  S  N  S  M  T  S  L  A  T  S  Q  H  S  P  G  I  D  K  E  N  V
1711  GAACTCTCCCCTACCACTGGCCACTGTAACAGTGGACGAACTCGCACGGATCCGCAAGCCAAGTGCAGAAGCAAAGAAGGCTGGCAGT
      E  L  S  P  T  T  G  H  C  N  S  G  R  T  R  H  G  S  A  S  Q  V  Q  K  Q  R  S  A  G  S
1801  TTCAAACGTAATAGCATTAAGAAGATCGTGTGAAGCTTGCTTGCTTTCTTTTTTAAAATCAACTTAACATGGGCTCTTCACTAGTGACCC
      F  K  R  N  S  I  K  K  I  V  *
                    D →
1891  CTTCCCTGTCCTTGCCTTTCCCCCATGTGTAATGCTGCACTTCCTGTTTTATAATGAACCCATCCGGTTTGCCATGTGCCAGATGA
1981  TCAACTCTTCGAAGCCTTGCCTAAATTTAATG
```

```
 991  AAACGTAAAGCAGCAGTTTGGCCACTACAAATCATTCTCCTTATCTTGTCCAGAAATAATCCAGGATATATCCAAAGACGTGGTTGAT
 260   K  R  K  A  A  V  W  P  L  Q  I  I  L  L  I  L  C  P  E  I  I  Q  D  I  S  K  D  V  V  D

1081  GAAAACAACATGAATAAGAAGTTATTTCTGGACAGTCTACGAAAAGCTCTTGCTGCCATGGAGGAAGTAGGCAGTGACAGAAAGTGCT
 290   E  N  N  M  N  K  K  L  F  L  D  S  L  R  K  A  L  A  G  H  G  G  S  R  Q  L  T  E  S  A

1171  GCAATTGCCTGTGTCAAACTGTGTAAAGCAAGTACTTACATC 1212
 320   A  I  A  C  V  K  L  C  K  A  S  T  Y  I

FIG. 9B
```

1. ... TAT TTA TGG TCG TTT TTA AGG ATA AGC TGT TAA CGT GTT TTT TTT TTC TTT TTT TTT CAG

2. ... ATG GCC GCG CAC AGG CCG GTG GAA TGG GTC CAG GCC GTG GTC AGC CGC TTC GAC GAG CAG CTT CCA ATA AAA ACA GGA CAG CAG ...
       M   A   A   H   R   P   V   E   W   V   Q   A   V   V   S   R   F   D   E   Q   L   P   I   K   T   G   Q   Q

3. ... AGC CTC TTG TGG CTT TGA ATT TTG TTT CAT CAA TTC CTA GGG TTT TGG CAA CTT CTC CTG
       S   L   L   W   L   -   I   L   F   H   Q   F   L   G   F   W   Q   L   L   L

FIG. 11

```
   1  MAAHRPVEWV  QAVVSRFDEQ  LPIKTGQQNT  HTKVSTEHNK  ECLINISKYK  FSLVISGLTT  ILKNVNNMRI  FGEAAEKNLY  LSQLIILDTL  EKCLAGQPKD
 101  TMRLDETMLB  KQLLPEICHF  LHTCREGNQH  AAELRNSASG  VLFSLSCNNF  NAVFSRISTR  LQELTVCSED  NVDVHDIELL  QYINVDCAKL  KRLLKETAFK
 201  FKALKKVAQL  AVINSLEKAF  WNWVENYPDE  FTKLLYQIPQT  DMAECAEKLF  DLVDGFAEST  KRKAAVWPLQ  IILLILCPEI  IQDISKDVVD  ENNMKKKLFL
 301  DSLRKALAGH  GGSRQLTESA  AIACVKLCKA  STYINWEDNS  VIFLLVQSMV  VDLKNLLFNP  SKPFSRGSQP  ADVDLMIDCL  VSCFRISPHN  NQHFKICLAQ
 401  NSPSTFHYVL  VNSLHRIITN  SALDWWPKID  AVYCHSVELR  NMFGETLHKA  VQGCGAHPAI  RMAPSLITFKE  KVTSLKFKEK  PTDLETRSYK  YLLLSMVKLI
 501  HADPKLLLCN  PRKQGPETQG  STAELITGLV  QLVPQSHMPE  IAQEAMEALL  VLHQLDSIDL  WNPDAPVETF  WEISSQMLFY  ICKKLTSHQM  LSSTEILKWL
 601  REILICRNKF  LLKNKQADRS  SCHFLLFYGV  GCDIPSSGNT  SQMSMDHEEL  LRTPGASLRK  GKGNSSMDSA  AGCSGTPPIC  RQAQTKLEVA  LYMFLWNPDT
 701  EAVLVAMSCF  RHLCEEADIR  CGVDEVSVHN  LLPNYNTFME  FASVSNMMST  GRAALQKRVM  ALLRRIEHPT  AGNTEAWEDT  HAKWEQATKL  ILNYPKAKME
 801  DGQAAESLHK  TIVKRRMSHV  SGGGSIDLSD  TDSLQEWINM  TGFLCALGGV  CLQQRSNSGL  ATYSPPMGPV  SERKGSMISV  MSSEGNADTP  VSKFMDRLLS
 901  LMVCNHEKVG  LQIRTNVKDL  VGLELSPALY  PMLFNKLKNT  ISKFFDSQGQ  VLLTDTNTQF  VEQTIAIMKN  LLDNHTEGSS  EHLGQASIET  MMLNLVRYVR
1001  VLGNMVHAIQ  IKTKLCQLVE  VMMARRDDLS  FCQEMKFRNK  MVEYLTDWVM  GTSNQAADDD  VKCLTRDLDQ  ASMEAVVSLL  AGLPLQPEEG  DGVELMEAKS
1101  QLFLKYFTLF  MNLLNDCSEV  EDESAQTGGR  KRGMSRRLAS  LRHCTVLAMS  NLLNANVDSG  LMHSIGLGYH  KDLQTRATFM  EVLTKILQQG  TEFDTLAETV
1201  LADRFERLVE  LVTMMGDQGE  LPIAMALANV  VPCSQWDELA  RVLVTLFDSR  HLLYQLLWNM  FSKEVELADS  MOTLFRGNSL  ASKIMTFCFK  VYGATYLQKL
1301  LDPLLRIVIT  SSDWQHVSFE  VDPTRLEPSE  SLEENQRNLL  QMTEKFFHAI  ISSSSEFPPQ  LRSVCHCLYQ  VVSQRFPQNS  IGAVGSAMFL  RFINPAIVSP
1401  YEAGILDKKP  PPRIERGLKL  MSKILQSIAN  HVLFTKEEHM  RPFNDFVKSN  FDAARRFFLD  IASDCPTSDA  VNHSLSFISD  GNVLALHRLL  WNNQEKIGQY
1501  LSSNRDHKAV  GRRPFDKMAT  LLAYLGPPEH  KPVADTHWSS  LNLTSSKFEE  FMTRHQVHEK  EEFKALKTLS  IFYQAGTSKA  GNPIFYYVAR  RFKTGQINGD
```

FIG. 12A

1601  LLIYHVLLTL KPYYAKPYEI VVDLTHTGPS NRFKTDFLSK WFVVFPGFAY DNVSAVYIYN CNSWVREYTK YHERLLTGLK GSKRLVFIDC PGKLAEHIEH

1701  EQQKLPAATL ALEEDLKVFH NALKLAHKDT KVSIKVGSTA VQVTSAERTK VLGQSVFLND IYYASEIEEI CLVDENQFTL TIANQGTPLT FMHQECEAIV

1801  QSIIHIRTRW ELSQPDSIPQ HTKIRPKDVP GTLLNIALLN LGSSDPSLRS AAYNLLCALT CTFNLKIEGQ LLETSGLCIP ANNTLFIVSI SKTLAANEPH

1901  LTLEFLEECI SGFSKSSIEL KHLCLEYMTP WLSNLVRFCK HNDDAKRQRV TAILDKLITM TINEKQMYPS IQAKIWGSLG QITDLLDVVL DSFIKTSATG

2001  GLGSIKAEVM ADTAVALASG NVKLVSSKVI GRMCKIIDKT CLSPTPTLEQ HLMWDDIAIL ARYMLMLSFN NSLDVAAHLP YLFHVVTFLV ATGPLSLRAS

2101  THGLVINIIH SLCTCSQLHF SEETKQVLRL SLTEFSLPKF YLLFGISKVK SAAVIAFRSS YRDRSFSPGS YERETFALTS LETVTEALLE IMEACMRDIP

2201  TCKWLDQWTE LAQRFAFQYN PSLQPRALVV FGCISKRVSH GQIKQIIRIL SKALESCLKG PDTYNSQVLI EATVIALTKL QPLLMKDSPL HKALFWVAVA

2301  VLQLDEVNLY SAGTALLEQN LHTLDSLRIF NDKSPEEVFM AIRNPLEWHC KQMDHFVGLN FNSNFNFALV GHLLKGYRHP SPAIVARTVR ILHTLLTLVN

2401  KHRNCDKFEV NTQSVAYLAA LLTVSEEVRS RCSLKHRKSL LLTDISMENV PMDTYPIHHG DPSYRTLKET QPWSSPKGSE GYLAATYPTV GQTSPRARKS

2501  MSLDMGQPSQ ANTKKLLGTR KSFDHLISDT KAPKRQEMES GITTPPKMRR VAETDYEMET QRISSSQQHP HLRKVSVSES NVLLDEEVLT DPKIQALLLT

2601  VLATLVKYTT DEFDQRILYE YLAEASVVFP KVFPVVHNLL DSKINTLLSL CQDPNLLNPI HGIVQSVVYH EESPPQYQTS YLQSFGFNGL WRFAGPFSKQ

2701  TQIPDYAELI VKFLDALIDT YLPGIDEETS EESLLTPTSP YPPALQSQLS ITANLNLSNS MTSLATSQHS PGIDKENVEL SPTTGHCNSG RTRHGSASQV

2801  QKQRSAGSFK RNSIKKIV

FIG. 12B

NEUROFIBROMATOSIS GENE

RELATED APPLICATIONS

This application is a divisional of U.S. Ser. No. 07/966,049, filed Aug. 2, 1993, which is a filing under 35 U.S.C. § 371 of International Application No. PCT/US91/04624, filed Jun. 28, 1991 which in turn is a continuation-in-part of U.S. Ser. No. 547,090, filed Jun. 29, 1990, now abandoned, the contents of which are hereby incorporated by reference into the present disclosure.

This invention was made in part with governmental support under National Institute of Health grants NS23410 and NS23427. The government may have certain rights to this invention.

FIELD OF THE INVENTION

The present invention relates generally to the gene involved in the von Recklinghausen neurofibromatosis (NF1) disease process and, more particularly, to the identification, isolation and cloning of a nucleic acid sequence corresponding to the gene. The present invention further relates to the NF1 gene product and sequence and antibodies raised thereto. The present invention also relates to methods of screening for NF1 and NF1 diagnosis, as well as conventional treatment and gene therapy utilizing recombinant technologies.

BACKGROUND OF THE INVENTION

Von Recklinghausen neurofibromatosis (NF1), often referred to as the "elephant man disease,"[1] is one of the most common autosomal dominant human disorders, affecting about 1 in 3,000 of the general population. The disease primarily involves neural crest-derived tissue and is characterized by café-au-lait spots, neurofibromas increasing in size and number with age, learning disabilities and mental retardation, seizures, and an increased risk of malignancy. The expression of the disease is extremely variable in its symptoms and severity, and the spontaneous mutation rate is remarkably high, with about 30 to 50% of all cases representing new mutations. Clinical diagnosis of NF1 has been relatively difficult early in life, due to the variability of the symptoms and their delayed appearance.

[1] An NIH panel, however, recently concluded that "Elephant Man" J. Merrick did not actually suffer from neurofibromatosis, but from an extremely rare disease known as the Proteus syndrome.

Direct cloning of the NF1 gene has not been possible due to the lack of a consistent abnormality in NF1 tissue which would provide sufficient information about the gene product. The remaining alternative has been positional cloning of the gene, utilizing its chromosomal map position rather than its functional properties. Using this approach, genetic linkage analysis led to the assignment of the NF1 gene to the proximal long arm of chromosome 17. Subsequent collaborative multipoint mapping efforts narrowed its genetic location to about 3 centiMorgans of 17q11.2. A combination of somatic cell hybrid techniques, linking clones and pulsed field gel electrophoresis (PFGE) applied to two unrelated NF1 patients having balanced translocations t(1;17) and t(17;22), with breakpoints approximately 60 kb apart on chromosome 17, further narrowed the location of the gene to a few hundred kilobases of chromosome band 17q11.2. See Collins, F. S. et al., *Trends in Genetics* 5:217–221 (1989).

The first NF1 candidate gene was identified in mice as a site of retroviral integration in murine leukemia. See Buchberg, A. M. et al., *Oncogene Research* 2:149 (1988). It has now been found, however, that the human homolog EVI2A, previously named EVI2, which maps between the NF1 breakpoints, is not interrupted by the aforementioned NF1 translocations, and no abnormalities in this gene have been identified as the cause of NF1. Similarly, EVI2B, previously named NF1-c2, a gene newly identified in the course of this invention by chromosomal walking and jumping, mapped between the NF1 breakpoints, was not interrupted by the NF1 translocations and exhibited no abnormalities in NF1 patients. It thus became clear that the NF1 gene had not yet been identified.

Recently, a gene was identified by positional cloning showing mutations in individuals affected with NF1. Cawthon, R. et al., *Cell* 62:193–201 (1990); Viskochil, D. et al., *Cell* 62:187–192 (1990); Wallace, M. R. et al., *Science* 249:181–186 (1990). Further cloning and partial sequence analysis demonstrated that the gene product contains a domain showing approximately 30% similarity to the catalytic domains of yeast IRA1 and IRA2 proteins and the mammalian GTPase activating protein (GAP). Buchberg, A. et al., *Nature* 347:291–294 (1990); Xu, G. et al., *Cell* 62:599–605 (1990). GAP is a cytosolic protein that catalyzes the conversion of active GTP-bound ras p21 to the inactive GDP-bound form. Trahey M. et al., *Science* 238:542–545 (1987). It was subsequently shown that the GAP related domain of the NF1 gene product can also interact with human and yeast RAS p21 to down-regulate its activity. Ballester, R. et al., *Cell* 63:851–859 (1990); Martin, G. A. et al., *Cell* 63:343–349 (1990); Xu, G. et al., *Cell* 63:835–841 (1990). Our previous reports of cDNA cloning of NF1 contained in parent application U.S. Ser. No. 547,090 were based on partial fragments of the transcript which is approximately 13 kb by Northern blotting. Wallace, M. R. et al., *Science* 249:181–186 (1990). The entire coding region of the NF1 gene has now been cloned and sequenced, the gene product identified and antibodies raised thereto, as described and claimed herein.

SUMMARY OF THE INVENTION

The entire coding region of the gene involved in von Recklinghausen neurofibromatosis (NF1 gene) and a ubiquitously expressed large transcript (NF1LT) of approximately 13 kb have been isolated, cDNA cloned and sequenced as set forth in FIGS. 6, 12 and the Sequence Listing. Analysis of the sequences revealed an open reading frame of 2818 amino acids, although alternatively spliced products may code for different sized protein products. The gene extends for a minimum of 270 kb on chromosome 17, with its promoter in a CpG rich island. The NF1 sequence is highly conserved and shows homology to the GTPase activating proteins family (GAP). The gene is interrupted by both NF1 translocations and altered in a new mutation NF1 patient, and contains previous candidate genes EVI2A (EVI2) and EVI2B (NF1-c2) within it. Antibodies which specifically recognize the NF1 gene product have been generated against both fusion proteins and synthetic peptides. Initial characterization of the NF1 gene product by both immunoprecipitation and Western blotting has revealed a unique protein of approximately 250 kDa. The protein has been found in a variety of human tissues and cell lines and is also present in rat and mouse tissues.

With the identification and sequencing of the gene and its corresponding gene product, nucleic acid probes and antibodies raised to the NF1 gene product can be used within the scope of the invention in a variety of hybridization and immunological assays to screen for the presence of a normal or defective NF1 gene or gene product. Functional assays to measure levels of gene function can also been employed for diagnosis or to monitor treatment. Assay kits for such screening and diagnosis in accordance with the principles of the invention can also be provided.

Patient therapy through supplementation with the normal NF1 protein, whose production can be amplified using genetic and recombinant techniques, or with its functional equivalent, is also possible. In addition, NF1 may be cured or controlled through gene therapy by correcting the gene defect in situ or using recombinant or other vehicles to deliver a DNA sequence capable of expression of the normal gene product to the patient. Treatment of non-NF1 tumors of the nervous system and growth stimulation of nervous tissue is also contemplated.

Other features and advantages of the present invention will become apparent from the following description and appended claims, taken in conjunction with the accompanying drawings.

BRIEF DESCRIPTION OF THE DRAWINGS

FIG. 6 (Sequence ID NO:3 and SEQ ID NO:4) is a partial nucleotide sequence of NF1LT cDNA with its corresponding amino acid sequence.

Figure 9A:
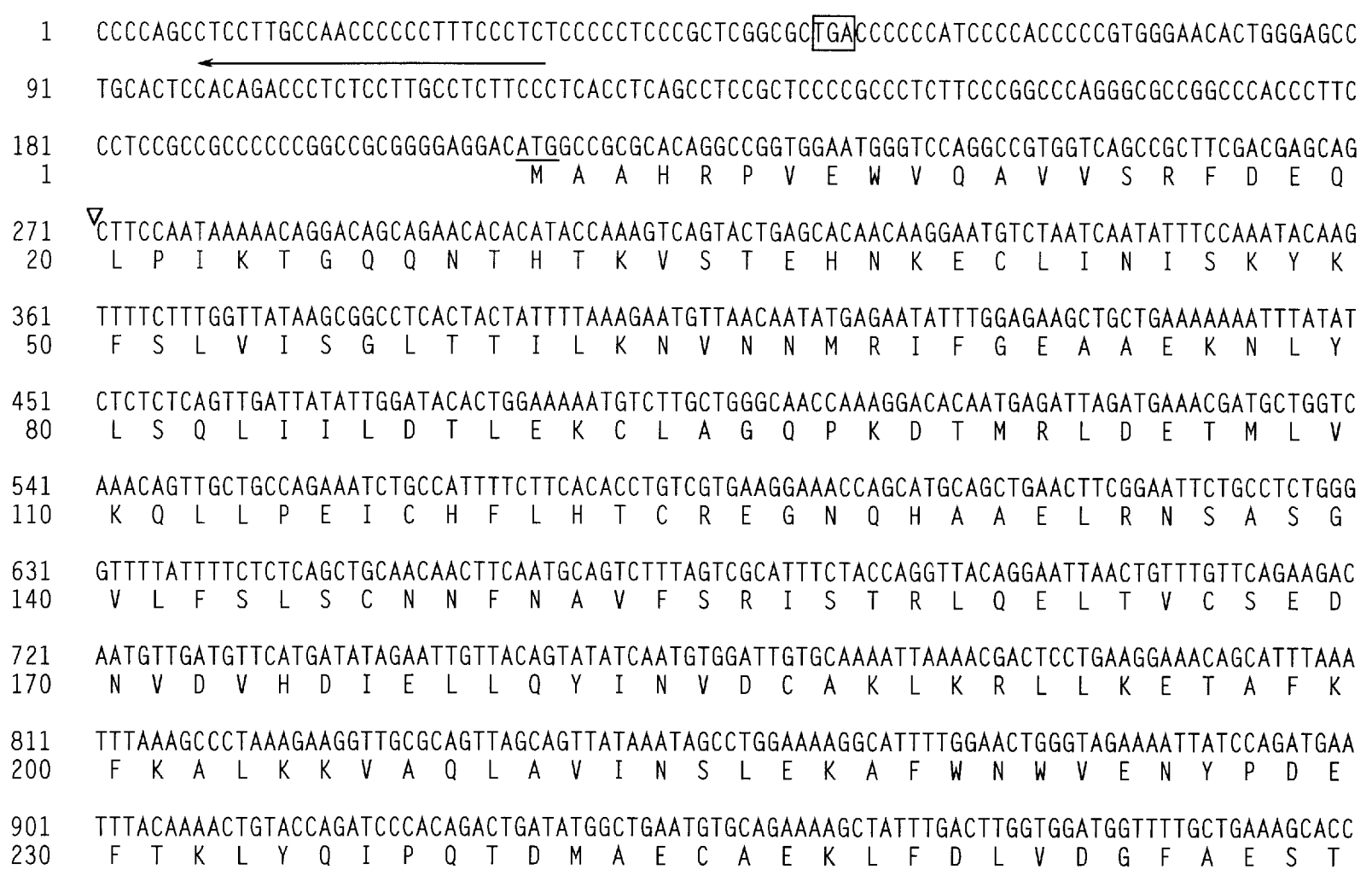

FIG. 9 (SEQ ID NO:5 and SEQ ID NO:6) is the cDNA sequence of the 5 portion of the NF1 transcript.

FIG. 11 (SEQ ID NO:7 through SEQ ID NO:11) presents alternate 5' ends found in cDNA clones.

FIG. 12 (SEQ ID NO:2) is the complete amino acid sequence of the NF1 gene product as deduced from the open reading frame of sequenced clones.

DETAILED DESCRIPTION OF THE INVENTION

Figure 1:
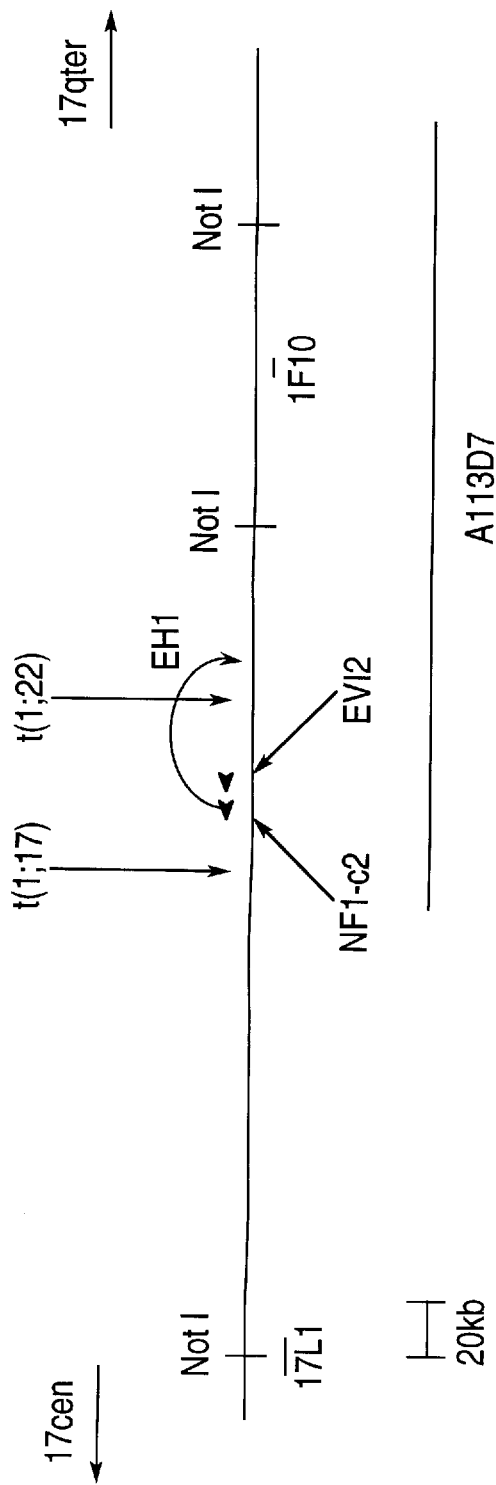
FIG. 1 is a schematic of the NF1 region drawn to scale in kilobases.

The NF1 gene, referred to as NF1LT prior to confirmation in Specific Example 1, has been identified, and its coding region cloned and sequenced. Partial and complete coding sequences of the NF1 gene and their corresponding amino acid sequences are depicted in FIGS. 6, 12 and the Sequence Listing appended hereto. Analysis of the sequences revealed an open reading frame of 2818 amino acids, although alternatively spliced products may code for different sized protein products. The gene extends for a minimum of 270 kb on chromosome 17, with its promoter in a CpG rich island. The NF1 sequence is highly conserved and shows homology to the GTPase activating proteins family (GAP).

The conclusion that the putative gene (NF1LT) is the gene involved in NF1, i.e. the NF1 gene, was based on several lines of evidence which are detailed below. First, this gene was clearly disrupted by the t(17;22) breakpoint, as shown at the DNA and RNA level. RNA analysis of the DCR1 human-mouse hybrid indicated that the NF1LT gene was functionally disrupted by the t(1;17) NF1 translocation as well. Even more compelling evidence was the identification of a 0.5 kb insertion in a new mutation NF1 patient. This insertion was located at least 10 kb away from the previously proposed genes EVI2A (EVI2) and EVI2B (NF1-c2). These candidate genes also failed to show abnormalities in NF1 patients and are apparently located in introns of NF1LT on the antisense strand. The large transcript size of NF1LT was also consistent with the high mutation rate of approximately $10^{-4}$/allele/generation.

To further elucidate the normal function of the NF1 gene product, and to determine the pathophysiologic basis by which alterations in the gene give rise to neurofibromatosis, it was desirable to develop specific antibodies which recognize the NF1 protein product. As a parallel example, the understanding of molecular pathology in Duchenne muscular dystrophy (DMD) was greatly enhanced by the development of antibodies against the DMD gene product, dystrophin. Hoffman, E. P. et al., Cell 63:835–841 (1990). Once these antibodies were generated, it became possible to localize the protein in cells and to correlate abnormalities in DNA with protein alterations. Bonilla, E. et al., Cell 54:447–452 (1988) and Lidov, H. G. W. et al., Nature 348:725–728 (1990). The distinction between Becker and Duchenne muscular dystrophy can now be made on the protein level, providing a reliable diagnostic tool for patient evaluation. Hoffman, E. P. et al., New England J. Med. 318:1363–1368 (1988).

In order to study the NF1 gene product, antibodies were raised against both fusion proteins and synthetic peptides. Initial characterization using two anti-peptide antisera and one fusion protein antiserum demonstrated a unique protein of approximately 250 kDa by both immunoprecipitation and Western blotting. This protein was found in all tissues and cell lines examined and is detected in human, rat and mouse tissues. To demonstrate that these antibodies specifically recognize the NF1 protein, additional fusion proteins were generated which contained the sequence against which the synthetic peptide antisera had been made. Both peptide antisera recognized their respective fusion proteins. Immunoprecipitates using the peptide antisera were shown to recognize the same protein detected by immunoblotting with either the other peptide antiserum or the fusion protein antiserum. Examination of adult tissue homogenates by Western blotting demonstrated the presence of the NF1 protein in all tissues using antisera which recognize spatially distinct epitopes.

SPECIFIC EXAMPLE 1

I. Isolation and Characterization of the NF1LT Transcript

A. Isolation and cloning

Two unique strategies were utilized to derive cDNA clones which define NF1LT. Initial experiments with the end-of-jump of clone EH1 obtained by chromosome jumping showed that a single-copy 1.4 Rb EcoRI-HindIII subfragment, which lies just telomeric to the t(17;22) breakpoint, is conserved across species and is therefore a potentially useful probe in searching for transcripts in the region. This probe was used to screen a human peripheral nerve cDNA library constructed from human cauda equina RNA by Marion Scott and Kurt Fischbeck of the University of Pennsylvania Medical Center. This library is partially oligo-dT-primed and partially random-primed, with the inserts cloned into the EcoRI site of λZAP (Stratagene, La Jolla, Calif.). 700,000 clones were plated on XL1-Blue cells and screened using the methodology described by Maniatis, T. et al., *Molecular Cloning*: A Laboratory Manual. Cold Spring Harbor: Cold Spring Harbor Laboratories (1982). The screening of this cDNA library resulted in the isolation of clone P5, which has an insert of 1.7 kb as shown in the Southern blot of FIG. 2A described below.

In an alternative approach, transcripts were sought using the YAC clone A113D7, part of an overlapping contig of clones from this region. As this YAC contains the entire breakpoint region, direct screening of cDNA libraries with this probe, although technically difficult, would be expected to yield an entire set of expressed transcripts. Field-inversion gel electrophoresis of YAC genomic DNA was performed in a 1.0% low melt agarose gel under conditions that separated the 270 kb YAC from the yeast chromosomes (160 volts, 65 hour run at 4° C. with a forward ramp of 6–48 seconds and a reverse ramp of 2–16 seconds). The YAC was cut out of the gel, equilibrated in digestion buffer, and digested with HincII. After re-equilibration in TE, the agarose was diluted in three volumes of water and melted at 68° C. Radiolabeling of the YAC was done in the diluted low melt agarose according to Feinberg, A. P. et al., *Anal. Biochem.* 137:266 (1984), except that 0.5 mCi was used in a final volume of 500 $\mu$l. After removing unincorporated counts using a spin column, probe was preannealed with human placental DNA at a final concentration 1 mg/ml in 0.1M NaCl for 15 minutes at 65° C. Phage lifts on nitrocellulose filters were prehybridized overnight in 6× SSC, 2× Denhardt's, 1 mM EDTA, 0.5% SDS. Hybridization was in the same solution for 48 hours. Filters were washed to a final stringency of 0.2× SSC, 0.1% SDS at 65° C. Clone B3A was isolated using the procedure described above from a B-lymphoblast cDNA library described by Bonthron, D. J. et al., *J. Clin. Invest.* 76:894 (1985) and contained a 0.8 kb insert. Subsequent analysis revealed that P5 and B3A overlap as shown in the Southern blot of FIG. 2A described below.

Referring now to FIG. 1, a schematic of the NF1 region drawn to scale in kilobases is shown. The orientation on chromosome 17 is shown and the translocation breakpoints are indicated by arrows. The two anonymous probes shown are 17L1 and 1F10 described by Fountain, J. W. et al., *Science* 244:1085 (1989) and O'Connell, P. et al., *Science* 244:1087 (1989). The previously described candidate genes EVI2A (EVI2) and EVI2B (NF1-c2) are shown above the map line, with the arrow heads indicating the direction of transcription. The jump clone EH1 is indicated by the arc. The 270 kb YAC A 113D7 is part of a contig covering this region and was obtained from the Center for Genetics in Medicine at Washington University by screening their YAC library with a probe derived from cosmid 1F10.

Figure 2A:
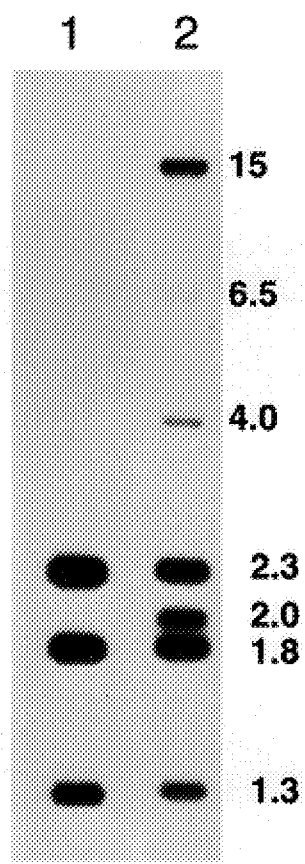
FIG. 2A is a Southern blot map of cDNA clones B3A and P5.

Referring now to FIG. 2, FIG. 2A shows Southern blot mapping of cDNA clones P5 and B3A. Genomic DNA from YAC clone A113D7 was digested with EcoRI, separated by gel electrophoresis and transferred to GeneScreen. Hybridization and wash conditions have been previously described by Drumm, M. L. et al., *Genomics* 2:346 (1988). The filter was probed sequentially with clone B3A (lane 1) and P5 (lane 2), with the filter being stripped between hybridizations. Each clone maps to specific EcoRI fragments in the YAC, the sizes of which are shown in kilobases. As shown in FIG. 2A, clone P5 contains a 1.7 kb insert and overlaps clone B3A.

Figure 2B:
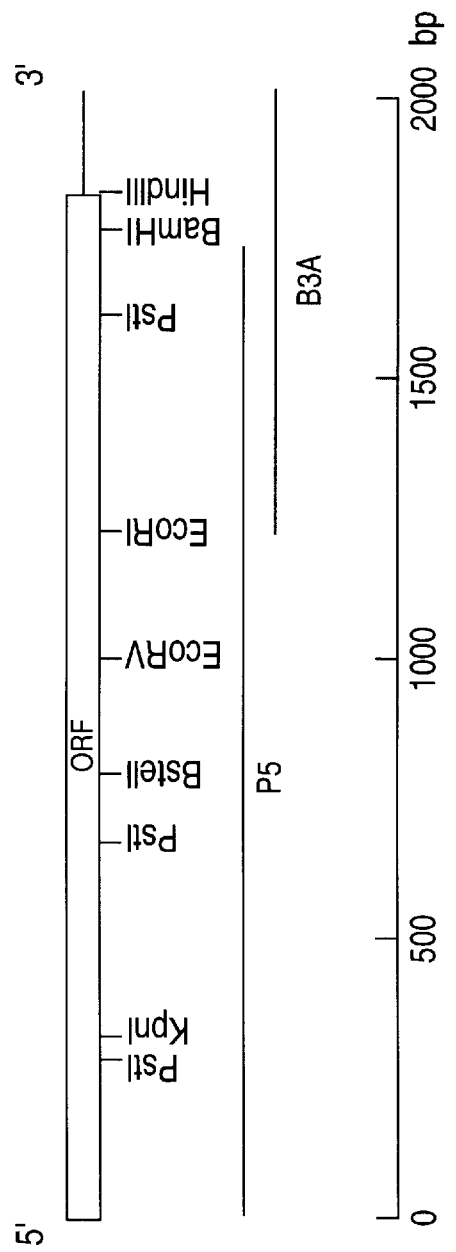
FIG. 2B is a schematic map of part of the NF1LT cDNA including cDNA clones P5 and B3A.

Referring now to FIG. 2B, a schematic map of part of the NF1LT cDNA shows the extent of the open reading frame and 3' untranslated regions, as well as cDNA clones P5 and B3A.

B. NF1LT crosses the t(17;22) breakpoint

To determine whether the NF1LT locus was interrupted by one or both translocation breakpoints, the 5' end of P5 was used as a probe against a Southern blot of the translocation hybrids. See Schmidt, M. A. et al., *J. Med. Genet.* 28:771 (1987); Ledbetter, D. C. et al., *Am. J. Hum. Genet.* 44:20 (1989); Menon, A. G. et al., *Genomics* 5:245 (1989); Collins, F. S. et al., *Trends in Genetics* 5:217 (1989). These hybrids contain chromosome 17 sequences telomeric to the breakpoints, with the t(1;17) break (hybrid DCR1) occurring 60 kb centromeric to the t(17;22) break (hybrid NF13).

Figure 3:
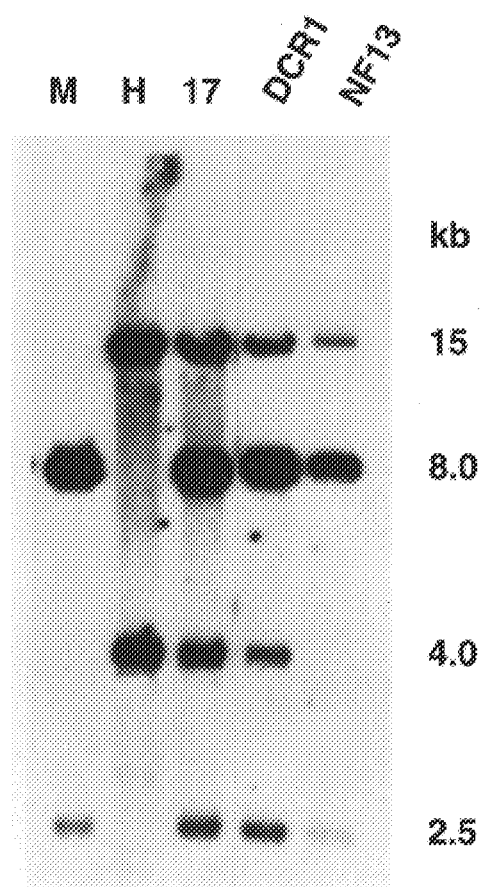
FIG. 3 is a Southern blot of human, mouse and hybrid DNA using the 5' end of the P5 probe, illustrating that NF1LT spans the t(17;22) breakpoint.

Referring now to FIG. 3, for this Southern blot, mouse, normal human and hybrid DNAs were digested with EcoRI, transferred to Hybond N, and hybridized as previously described by Wallace, M. R. et al., *Nucleic Acid Res.* 17:1665 (1989). The final wash was 1XSSC/0.1% SDS at 65° C. for 20 minutes. The probe was a 0.8 kb 5' end fragment from the P5 Bluescript subclone, extending from the vector polylinker to the BstEII site shown in FIG. 2B. In FIG. 3, M represents mouse DNA; H, normal human DNA; 17, DNA from hybrid MH22–6, a mouse cell line containing human chromosome 17 as its only human material described by Tuinen, et al., *Genomics* 1:374 (1987); DCR1, the mouse hybrid containing the der(1) of t(1;17); and NF13, the hybrid containing der(22) of t(17;22).

The results in FIG. 3 show that the P5 5' end probe detects two human EcoRI fragments of 15 and 4.0 kb. Two bands of 8.0 and 2.5 kb are seen in mouse DNA, indicating that this transcript is strongly conserved. In the translocation hybrids, DCR1 contains both human bands, but NF13 lacks the 4.0 kb band, indicating that part of NF1LT lies between these breakpoints.

Although the Southern blot presented in FIG. 3 appears to indicate that the P5 partial cDNA clone extends across the t(17;22) translocation breakpoint in an NF1 patient, subsequent experiments have shown this to be incorrect; the entire P5 clone actually lies telomeric to this breakpoint. The apparent absence of the 4.0 kb Eco RI genomic fragment from the der(22) chromosome in FIG. 3 is due to the fact that the translocation falls within this 4.0-kb interval, and the resulting breakpoint fragment happens to be precisely the same size (15 kb) as the other human genomic band in this lane of the blot.

Our subsequent additional cDNA cloning efforts indicate that the t(17;22) break interrupts the NF1LT cDNA 681 bp 5' to the end of P5 (between exons 4 and 5 in the numbering system of Cawthon, R. M. et al., Cell 62:193 (1990)). The evidence for this is illustrated in FIG. 1 of Wallace, M. R. et al., Science 250:1749 (1990) which shows a Southern blot performed with genomic DNA amplified with PCR primers for exon 4 and exon 5. The PCR primer sequences were located in the introns adjacent to the exons and are given in Cawthon, R. M. et al., Cell 62:193 (1990). The source of DNA was normal human; NF13 mouse human hybrid containing the der(22) chromosome from the t(17;22) NF1 translocation; mouse; and water as a negative control.

C. RNA analysis

Figure 4A:
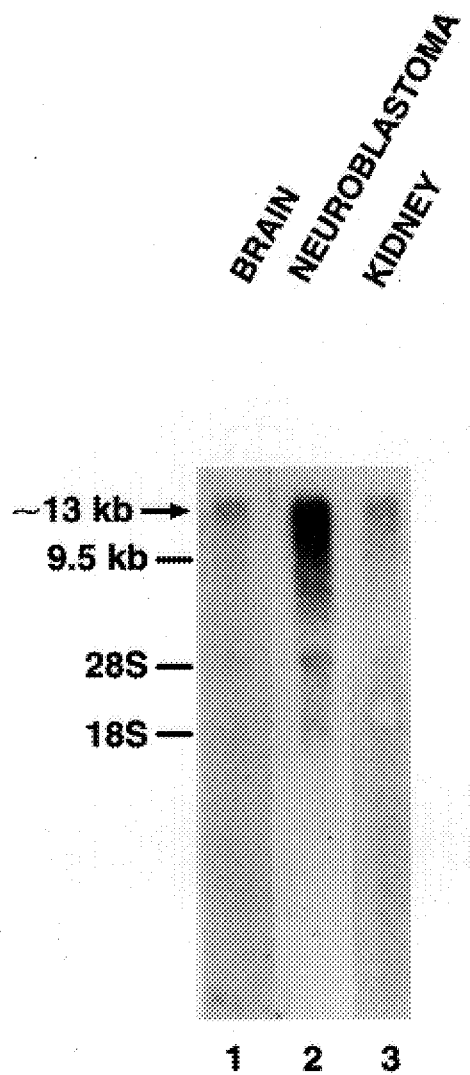
FIG. 4A is a Northern blot of various human tissues using the P5 probe.
Figure 4B:
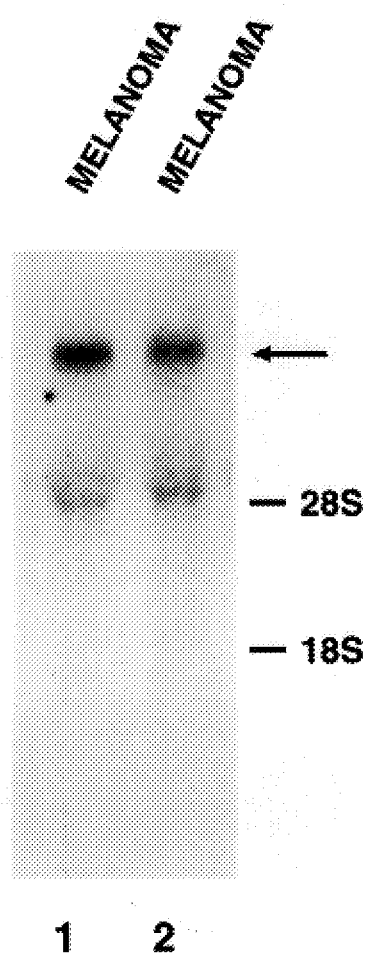
FIG. 4B is a Northern blot of two independent melanoma cell lines using the P5 probe.

To determine the transcript size of NF1LT cDNA, clone P5 was used to probe Northern blots of RNA from a variety of tissues. As shown in FIGS. 4A and B, an approximately 13 kb transcript was visualized in brain, neuroblastoma and kidney tissue, and two melanoma cell lines. A hybridization signal of similar size was visible in RNA from several other tissues, although the bands were less discrete, probably due to degradation of the large transcript. Because of differences in degradation between RNA samples, it was not possible to judge from the band intensities the relative level of expression in different tissues.

Figure 4C:
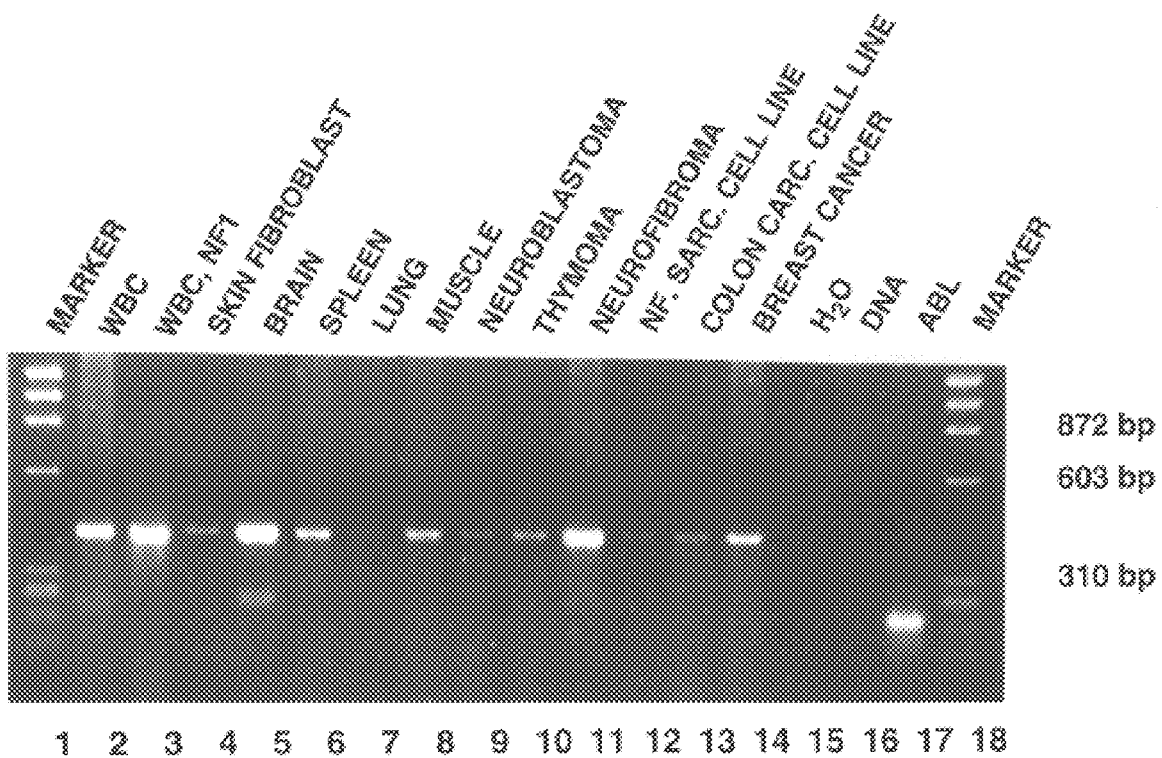
FIG. 4C is a PCR analysis of RNA expression in various human tissues and cell lines using primers A and B.

In order to survey the pattern of expression of NF1LT in different normal and pathologic tissues, RNA Polymerase Chain Reaction (PCR) analysis as described by Gibbs, R. A. et al., PNAS (USA) 86:1919 (1989) was performed of a number of tissues using primers from the translated region. As shown in FIG. 4C, expression of NF1LT was apparent in a wide variety of human tissues, including those giving signals on Northern blots, as well as immortalized B-lymphoblasts (WBC) (both NF1 and non-NF1), NF1 skin fibroblasts, spleen, lung, muscle, thymoma, neuroblastoma, an NF1 neurofibrosarcoma cell line, a colon carcinoma cell line, and breast cancer. In other experiments, expression was also detected in colon, thyroid, parathyroid adenoma, lymphoma, endometrial carcinoma, K562 erythroleukemia cells, and normal skin fibroblasts. Leukocyte contamination of the solid tissue samples could potentially account for the PCR signals, but the fact that RNAs from various cell lines show expression indicates it is likely that NF1LT is widely expressed.

D. Expression of NF1LT Abolished in the t(1;17) Rearrangement

Figure 4D:
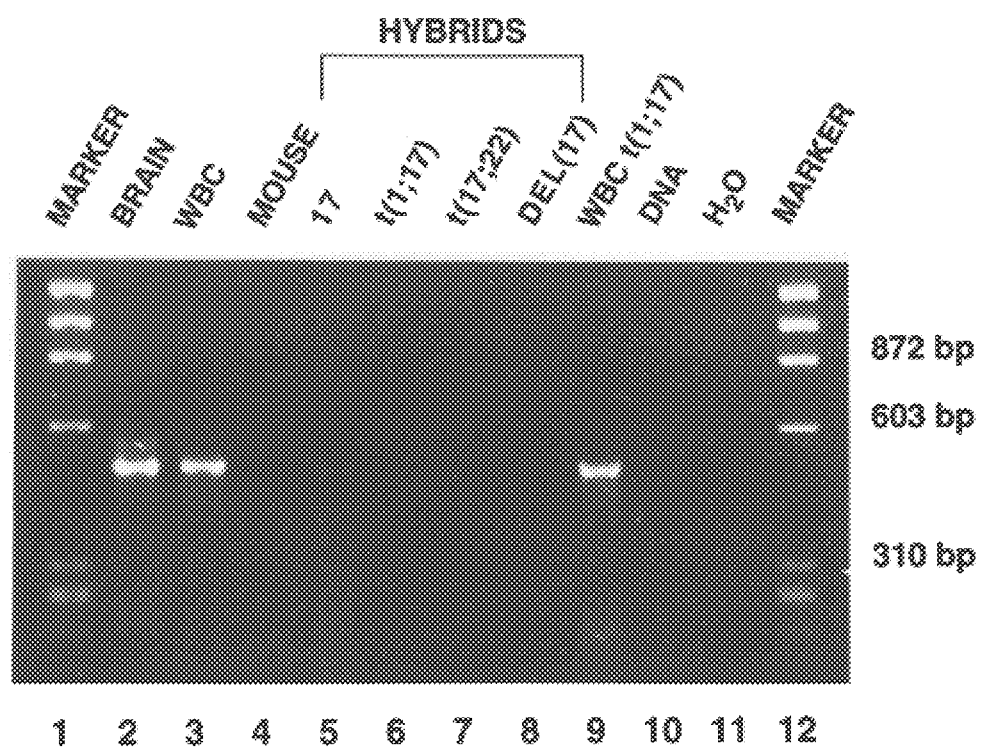
FIG. 4D are PCR results from RNA from mouse-human hybrid and parental cell lines using primers C and D which do not amplify mouse NF1LT RNA.

The primers used in the above experiments amplified a band of similar size in mouse RNA, showing that this translated region is conserved. In order to determine if the NF1LT gene was inactivated in three hybrid cell lines from NF1 patients with cytogenetic rearrangements, one PCR primer from the 3' untranslated region was included, with the expectation that this area would be less conserved across species. The three hybrid cell lines included in this experiment were DCR1 and NF13, described above, and del(17). This last hybrid contains the deleted chromosome 17 from an NF1 patient with a deletion of part of the proximal long arm of chromosome 17. As shown in FIG. 4D, the expected product is seen in B-lymphoblasts (WBC) and human brain, but not in mouse fibroblast RNA. A hybrid containing the normal human chromosome 17 does express human NF1LT, but no product is visible with either NF1 translocation hybrid or with the del(17) hybrid, indicating that these rearrangements abolish expression.

II. DNA Abnormality in a New Mutation NF1 Patient

Identifying mutations in NF1 patients is crucial to correctly identifying the gene from among candidate genes. New mutation NF1 patients are particularly helpful, since comparison of their DNA with that of their parents allows the distinction between causative mutation and polymorphism to be more readily made. Since pulsed-field gel studies by several groups with probes in the NF1 region have failed to reveal large rearrangements (see Fountain, J. W. et al., Science 244:1085 (1989); O'Connell, P. et al., Science 244:1087 (1989)), patient DNA was examined at the Southern blot level with NF1LT. DNA from 35 individuals with NF1 was analyzed with the probe P5, and the autoradiograms were examined for abnormal bands or obvious differences in band intensity.

A single patient showed a difference with this assay. This NF1 new mutation patient is a 31-year-old white male who exhibits no café-au-lait spots or axillary freckling, but has macrocephaly, Lisch nodules, and multiple cervical nerve root tumors (shown histologically to be neurofibromas) requiring surgical debulking. He had a single cutaneous neurofibroma removed several years ago, and has no evidence of acoustic neuroma. His parents were carefully examined and displayed no features of NF1 or NF2. FIGS. 5A–D display Southern blots of DNA from this patient (lane 2) and his parents (lanes 1 and 3) using four enzymes and probe P5.

With EcoRI (FIG. 5A), the patient had a normal pattern except that his 4.0 kb allele was fainter than expected and he also demonstrated an abnormal fragment of 4.5 kb, with approximately the same intensity as the 4.0 kb band. This 4.5 kb band was not present in the parents. Similarly, with three other enzymes, an abnormal fragment approximately 0.5 kb larger than expected was seen. For Pst I, the involved 12 kb fragment was the same one previously shown to contain the t(17;22) breakpoint. These abnormal bands were not seen in the 34 other NF1 patients (12 of whom represent new mutations) or 27 unaffected individuals. As a confirmation, the family members were resampled, and the same results were obtained. The family was studied with three highly polymorphic VNTR probes pYNZ22, pYNH24 and pEK-MDA2 as described by Nakamura, Y. et al., Science 235:1616 (1987), and there was no indication of incorrect paternity.

Collectively, this data indicates that this patient possesses a novel mutation which appears to be an insertion of approximately 0.5 kb close to or within an exon of NF1LT. This new mutation, along with the evidence showing that the t(17;22) breakpoint interrupts the gene, and the PCR data showing that NF1LT expression is absent in the t(1;17) hybrid DCR1, indicates that NF1LT is the NF1 gene.

III. Partial Nucleotide Sequence and Analysis of NF1LT

Complete sequencing of P5 and B3A revealed an overlap of 507 bp, with the combined sequence being 2012 bp as shown in FIG. 6. A single open reading frame was identified extending from the beginning of P5 across nearly the entire sequence, which shows that B3A is located at the 3' end and that transcription occurs toward the telomere. At the 3' end of B3A, a stop codon occurs 181 bp from the end. However, no polyadenylation signal or poly(A) tail was evident, which implied that part of the 3' untranslated region was missing. Comparisons of this DNA and protein sequence with the entries in Genbank (see Burks, C. et al., Meth. Enzymol. 183:3 (1990)), and the NBRF and SWISS-PROT databases (see Barker, W. C. et al., Meth. Enzymol. 183:31 (1990) and Kahn, P. et al., Meth. Enzymol. 183:23 (1990)), failed to show significant similarity with any known sequence. A hydropathy plot of the amino acid sequence revealed a primarily hydrophilic polypeptide. See Kyle, J. et al., *J. Mol. Biol.* 157:105 (1982). Other analyses failed to reveal any other recognizable motifs except for two potential N-glycosylation sites and three possible nuclear localization signals depicted in FIG. 6.

Figure 7:
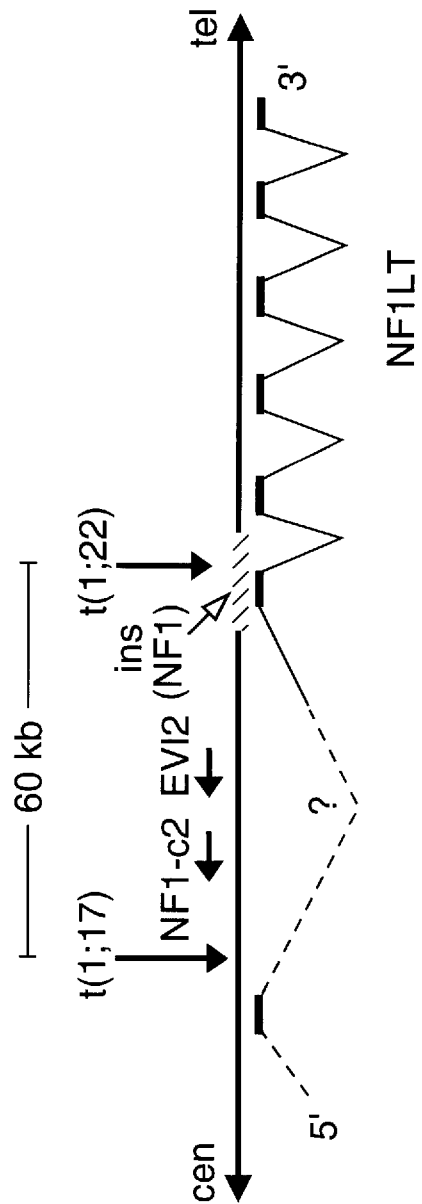
FIG. 7 is a schematic partial exon map of NF1LT.

Referring now to FIG. 7, the postulated genomic structure of NF1 is schematically represented. The 2.0 kb cloned portion of the NF1LT cDNA contains at least 6 exons. The 5' exon of the cloned transcript lies between the NF1 translocation breakpoints, within 12 kb of t(17;22). The size and number of genomic fragments detected by NF1LT probes P5 and B3A on Southern blots indicated that the 2.0 kb of cloned CDNA spaned at least 33 kb of genomic DNA. Thus it was unlikely that the remaining 5' exons could lie entirely between the translocation breakpoints.

Based on the observation that CpG islands often lie at the 5' ends of genes, especially housekeeping genes, the next 5' CpG island was a potential site for the promoter of NF1. This island has been previously cloned in the NotI linking clone 17L1 shown in FIG. 1 and described by Wallace, M. R. et al., *Nucleic Acids Res.* 17:1665 (1989). It lies approximately 150 kb centromeric to the t(1;17) breakpoint and shows strong conservation across species, and subsequent investigation detailed in Specific Example 2 demonstrates that it does contain the promoter of the NF1 gene. The remainder of the NF1 gene was cloned by cDNA walking, YAC technology, and examination of genomic upstream sequences as described in Specific Example 2.

SPECIFIC EXAMPLE 2

I. Isolation of NF1 cDNA Clones

Five different cDNA libraries were used in the cDNA walk. Libraries included fetal muscle, fetal brain, adult brain (occipital pole and medulla), and endothelial cells. The human fetal brain cDNA library, oligo(dT) and random primed, was obtained from Stratagene, La Jolla, Calif. (#936206). The human fetal muscle library, oligo (dT) primed, was a gift of F. Boyce and is described in Koenig, M. et al., *Cell* 50:509–517 (1987). The adult human occipital pole cDNA library, random and oligo(dT) primed, was obtained from Clontech, Palo Alto, Calif. (#HL1091a). The adult human medulla library, random and oligo(dT) primed, was obtained from Clontech (#HL1089a). An endothelial cell library, random primed, was a gift of D. Ginsburg. Ginsburg, D. et al., *Science* 228:1401–1406 (1985). Clones P5, isolated from a peripheral nerve CDNA library, and B3A, from a B-lymphocyte library, were isolated as previously described herein and in Wallace M. R. et al., *Science* 249:181–186 (1990). Since the NF1 transcript has been shown to be ubiquitously expressed (see Buchberg, A. et al., *Nature* 347:291–294 (1990); Wallace, M. R. et al., *Science* 249:181–186 (1990)), cDNA walking proceeded in the previously described multiple cDNA libraries in order to maximize chances of finding positives. Walks proceeded by isolation of positive phage clones using the most 5' cDNA insert.

Typically, 500,000 plaques of each library were plated and screened as described in Benton, W. D. et al., *Science* 196:180–182 (1977), using an aqueous hybridization consisting of 6x SSC, 2x Denhardts solution, 1 mM EDTA and 0.5% SDS at 65° C. Washes were in 2x, 1x, and, if needed, 0.2x SSC, 0.1% SDS at 65° C. The positive clones were characterized by restriction mapping using EcoRI and Southern blot analysis using previously isolated inserts. The phage clones were subcloned into Bluescript (Stratagene) or rescued as plasmid per λZAP instructions in the case of the fetal brain library, and the ends were sequenced to anchor the position of the clones to the transcript map. The cycle was repeated for each walk. Underrepresented regions in any given library were overcome by crossing into another library. The entire transcript as represented in the clones was sequenced multiple times and both strands were sequenced at least once for all previously unpublished sequence.

Figure 8:
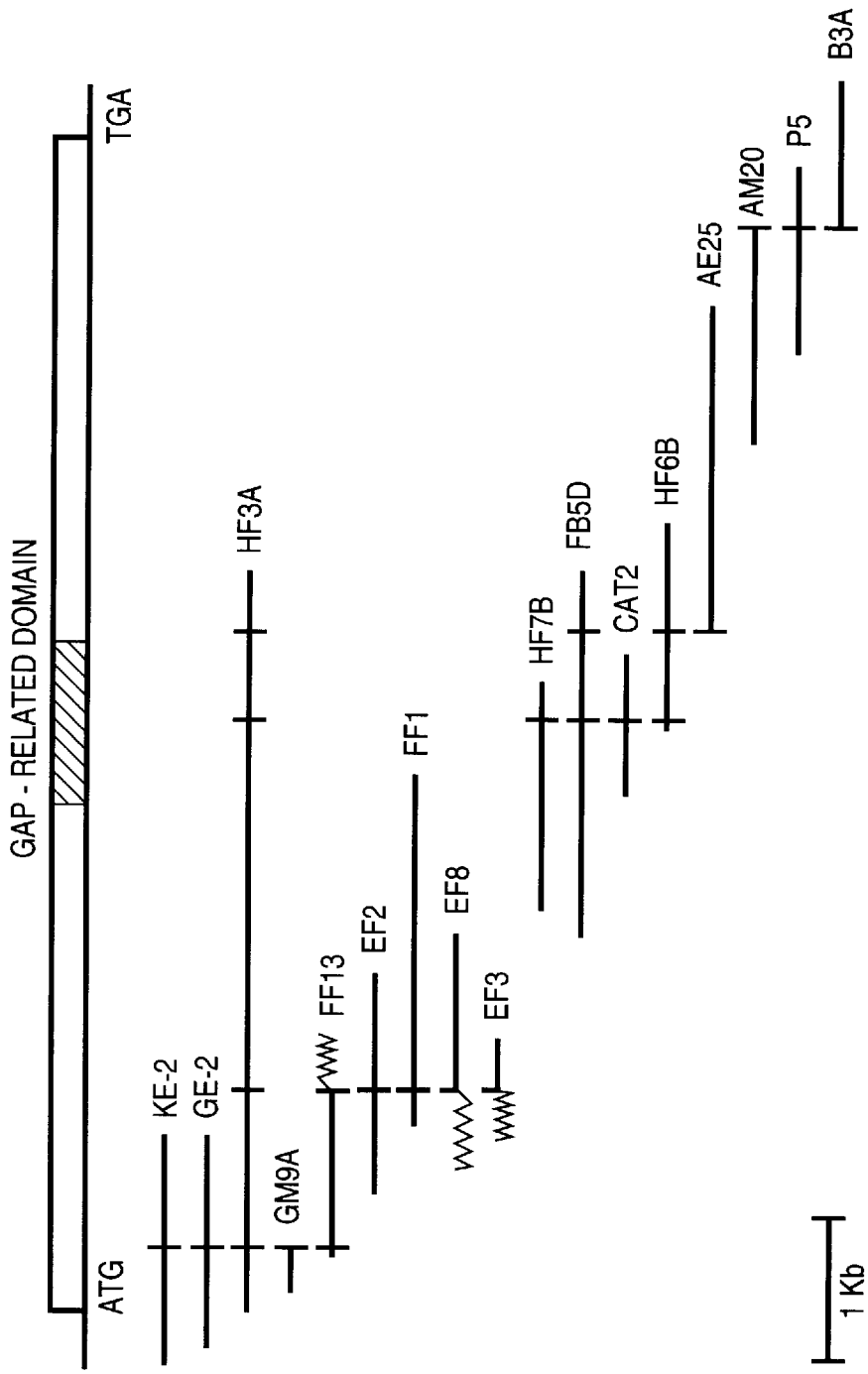
FIG. 8 is a schematic diagram representing the cDNA walk in the NF1 gene.

FIG. 8 is a schematic diagram representing the cDNA walk from the 3' end of the NF1 gene. The open reading frame is represented by the wide region bound by the ATG and TGA codons, and the extent of the GAP related domain used in complementation studies of Ballester, A. et al., *Cell* 63:851–859 (1990) is indicated. Clones are listed below the schematic of the transcript, straight lines represent authentic transcript and jagged lines represent co-cloning events. EcoRI sites are represented by vertical lines. Clones B3A and P5 have been previously described herein and in Wallace, M. R. et al., *Science* 249:181–186 (1990). Clones AE25, KE-2, and GE-2 were isolated from the endothelial cell cDNA library. Ginsburg, D. et al., *Science* 228:1401–1406 (1985). Clones HF6B, FB5D, HF7B, EF3, EF8, FF1, EF2, FF13, and HF3A were isolated from the fetal brain cDNA library (Stratagene, #936206). Clone CAT2 was isolated from the same library by PCR from total phage lysate from the library. See Ballester, R. et al., *Cell* 63:851–859 (1990). Clone AM20 was isolated from a human brain (medulla) cDNA library (Clontech, #HL1091 a), and clone GM9A was isolated from the fetal muscle cDNA library of Koenig, M. et al., *Cell* 50:509–517 (1987).

As the cDNA walk neared completion, a very GC rich region of the transcript was encountered at the 5' end that contained an abnormally high concentration of the dinucleotide CpG, as well as some rare cutting restriction endonuclease sites. Some of these sites had been previously placed on the pulsed field map of this region using the NotI linking clone 17L1. Fountain, J. W. et al., *Amer. J. Hum. Genet.* 44:58–67 (1989). This clone was isolated from a NotI linking library constructed from DNA from flow-sorted chromosome 17 (Wallace, M. R. et al., *Nucleic Acids. Res.* 17:1665–1677 (1989)) and contains the sequences flanking both sides of a genomic NotI site. The telomeric half of the probe was used to detect a translocation breakpoint within the NF1 gene. Fountain, J. W. et al., *Science* 244:1085–1087 (1989). Southern blots using the CpG rich cDNAs as probes against 17L1 demonstrated that the most 5' sequences obtained were indeed located in centromeric half of this clone (17L1B), approximately 300 kb from the 3' stop codon.

The most 5' clone, KE-2, isolated from the endothelial cell cDNA library contained an in frame stop codon as shown in FIG. 9 which depicts the cDNA sequence of the 5' portion of the NF1 transcript. The sequence in FIG. 9 has not been previously published, ending where previously published sequence began.

Wallace, M. R. et al., *Science* 249:181–186 (1990); Cawthon, R. et al., *Cell* 62:193–201 (1990); Xu, G. et al., *Cell* 63:835–841 (1990). Sequence was compiled from clones KE-2, GE-2, GM9A, EF2, FF13, and HF3A. Both strands were sequenced at least once to complete the sequence. The nucleotide and deduced amino acid sequence are numbered along the left column. The start codon is underlined, and the upstream in frame stop codon is boxed. The position of the oligonucleotide used for primer extension (FIG. 10) is shown by an arrow. The position of the first intron, is indicated by a triangle, and is the position where alternate sequences diverge (FIG. 11).

Downstream from the stop codon, the first ATG fits the rules for a proper translational start. See Kozak, M., *Cell*

44:203–292 (1986). Overlapping sequences have been found in cDNA clones from three different tissues (fetal muscle, fetal brain, and endothelial cells). We propose that this ATG codon represents the authentic start codon, giving the protein, a total of 2818 amino acids with a predicted molecular weight of about 327 kilodaltons.

II. Primer Extension

Figure 10:
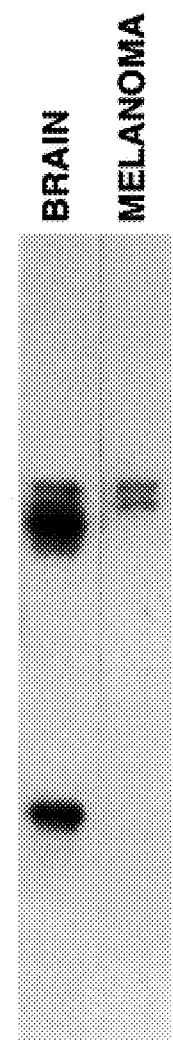
FIG. 10 is a PAGE analysis of the primer extension off of frontal lobe human brain total RNA and melanoma cell mRNA.

In order to determine whether a substantial portion of the 5' end of this transcript remained uncloned, a primer extension was performed using human brain (frontal lobe) and melanoma cell line SK-MEL-23 poly A+ RNA. Total RNA was isolated from fresh human brain (frontal lobe) and a melanoma cell line SK-MEL-23 (Carey, T. E. et al., *PNAS (USA)* 73:3278–3282 (1976)) as described in Sambrook, J. et al., *Molecular Cloning: A Laboratory Manual 2nd ed.*, Cold Spring Harbor: Cold Spring Harbor Laboratory (1989). Polyadenylated RNA was isolated from melanoma total RNA using the FastTrack mRNA isolation kit (Invitrogen Corp., San Diego, Calif.). For primer extension, an oligomer (5' AGAGGCAAGGAGAGGGTCTGTG(SEQ ID NO:12)) was synthesized, kinased with 32P, and extended off of brain (total RNA) melanoma (polyA+ RNA) Boorstein, W. R. et al., *Primer Extension Analysis of RNA; Meth. Enymol.* 180:347–369, Academic Press, San Diego (1989). The reverse transcription primer chosen was 5' of the proposed start codon, within the proposed exon 1 at the position shown in FIG. 9. Products were analyzed on a 6% denaturing polyacrylamide gel. FIG. 10 shows the result of this analysis.

As shown in FIG. 10, a series of four bands ranging in size from 380–410 bp is seen in the extension from brain RNA. A second prominent band of 300 bp is also seen. Primer extension from the melanoma RNA shows the top two bands at 400 and 410 bp, but does not show the lower band at 300 bp. Cloning and sequencing was done 119 bp from the 5' position of this primer, indicating that at most only 291 bp remain uncloned. Within the cloned sequence lies the proposed ATG start and upstream in frame stop codon. These results indicate that the entire coding region of the transcript has been cloned and sequenced.

III. Sequence Analysis of Clones

Double stranded sequencing of plasmid clones was performed using Sequenase Version 2.0 (U.S. Biochemicals, Cleveland, Ohio) per instructions. Sequence analysis was performed using the Pustell and Cyborg sequence analysis programs. Analysis of the amino acid sequence was performed with the GCG protein analysis package.

Sequencing of the proximal half of the NotI linking clone 17L1 (17L1B) demonstrated that the 5' cDNA sequences from nucleotide 1 to 270 exist in this region of the genome in a single continuous exon. This indicates that exon 1 of this transcript has been cloned and contains a majority of sequence that is 5' untranslated. If another exon exists upstream, it would contain entirely non-coding sequence. The transcriptional start site and the promoter region probably exist in the half linking clone 17L1B.

A. 5' End alternate sequences

In the course of screening for cDNA clones that extended beyond our most 5' clone, two alternate sequences were discovered and are shown in FIG. 11. Sequences numbered 1 and 3 are derived from clones isolated from a fetal brain cDNA library and were each represented by single isolates, not shown in FIG. 8. Sequence number 2 matches clones from cDNA libraries from three different tissues, and contains the 5' end shown in FIG. 9. The position of the first splice junction is shown by a thick line separating exon 2 to the right and the three different exon 1 sequences to the left.

Sequence number 1 has been shown by PCR to be unspliced message, and the consensus AG and lariat sequences are underlined. Sequence number 2 represent the most prominent species of mRNA, and has a proper consensus start codon. Kozak, M., *Cell* 44:283–292 (1986). Sequence number 3 has an in frame stop codon which is boxed.

Both alternate sequences begin at position 270, the position of the first intron-exon border, and are represented by single cDNA clones from a fetal brain cDNA library. Sequence 1 is an unspliced message, as it contains a perfect splice junction acceptor consensus sequence, a pyrimidine stretch of 20 bases, and a lariat formation consensus sequence. Sharp, P. A., *Science* 235:766–771 (1987). This was confirmed by designing primers that extend across the splice junction and showing that these primers will amplify the correct sized fragment using genomic DNA. If this sequence does represent an authentic mRNA, it contains an in frame stop codon just ten triplets upstream from the splice junction.

A second unusual clone diverges at the exact same position, yet has a different sequence, sequence 3, and thus must be an alternative splice product at the 5' end. It contains an in frame stop codon only 15 triplets upstream from the point of divergence, without a methionine codon in the new sequence. This clone is also unusual in that in contains an Alu repeat at one end, and may be only partially spliced. However, if it does represent an authentic 5' end sequence, it would code for a smaller protein product, possibly beginning translation at the next ATG 58 codons downstream from the splice junction.

B. 3' End of sequence

Characterization of the 3' end of the NF1 transcript has not been completed, as a poly A tail has not been found in any cDNA clone. Previous sequence analysis has shown the proper position of the stop codon. See Wallace, M. R. et al., *Science* 249:181–186 (1990); Xu, G. et al., *Cell* 62:599–608 (1990). Downstream from this the sequence is very A rich, with some regions that may be capable of priming with oligo dT during construction of the cDNA libraries. The NF1 transcript has been estimated to be 13 kb by its migration on a Northern blot. Wallace, M. R. et al., *Science* 249:181–186 (1990). To date we have cloned and sequenced over 9 kb of this message. The primer extension results (FIG. 10) indicate that the majority of uncloned sequence from this transcript arise from a very long (approximately 4 kb) 3' untranslated region. Alternatively, our estimates of transcript size may be incorrect, as size estimates in this range of Northern blotting are difficult.

At least two other alternate processed forms of this primary transcript have been discovered. A 54 bp insertion coding for an additional 18 amino acids (ASLPCSNSAVFMQLFPHQ(SEQ ID NO:13)) near the 3' end of the transcript has been previously described Cawthon, R. et al., *Cell* 62:193–201 (1990); Xu, G. et al., *Cell* 62:599–608 (1990); Cawthon, R. et al., *Genomics* 7:555–565 (1990). A 63 bp insertion coding for an additional 21 amino acids (ATCHSLLNKATVKEKKENKKS) within one of the most conserved regions of the GAP related domain has been discovered.

C. Complete sequence

FIG. 12 shows the complete amino acid sequence of the primary NF1 transcript deduced from the open reading frame of sequenced clones from the cDNA walk. Boxed areas indicate the 4 blocks of homology most conserved between the GAP family of proteins. Wang, Y. et al., *Cell Regulation* 2:453–465 (1991). The positions of the alternatively spliced exons and their sequence is shown. There are no SH2 or SH3 domains (src homology domains), which are present in GAP. The protein shows no apparent membrane spanning region, and is predicted to be cytosolic by discriminant analysis. Klein, P. et al., *Biochim. Biophys. Acta* 815:468–476 (1985). A potential leucine zipper is present beginning at amino acid residue 1834, but this region is not predicted to be in an alpha-helical conformation due to the presence of a proline in the middle of the repeat. Six potential cAMP-dependent protein kinase phosphorylation sites and one potential tyrosine phosphorylation site are present. The sequence shows no significant homology to the recently described Bcr related GAP family which includes n-chimaerin, and GAPrho (Diekmann, D. et al., *Nature* 351:400–402 (1991)) and possibly the p85 of bovine brain phosphatidylinositol 3-kinase. Otsu, M. et al., *Cell* 65:91–104 (1991).

Referring again to FIG. 12, the boxed regions in FIG. 12 correspond to the most statistically significant regions of similarity among the GAP family of proteins with the invariant residues marked with stars. Residues underlined with a thin line are the potential cAMP-dependent protein kinase recognition sites. Residues that are double underlined represent the potential tyrosine phosphorylation recognition sequence. The position of a 21 amino acid insertion representing an alternatively spliced product is shown with a dark triangle. The position of an 18 amino acid insertion (ASLPCSNSAVFMQLFPHQ) representing an alternatively spliced product is shown by an open triangle. Xu, G. et al., *Cell* 62:599–608 (1990).

We found three regions of our nucleotide sequence that were at variance with previously published sequence (Xu, G. et al., *Cell* 62:599–608 (1990)), two resulting in changes in the amino acid sequence. Residue number 496 in our clones shows an ATG methionine codon rather than an ATA isoleucine codon. Another sequence variation at residue 1183 shows an CTG leucine codon rather than the previously published CTC. Our clones also lacked an extra CAT histidine codon after residue number 1555. The latter two changes that we have noted agree with those of Martin, G. A. et al., *Cell* 63:843–849 (1990), from their sequence of a PCR clone of the GAP-related domain region.

D. YAC mapping

The size of the NF1 gene has been determined by mapping cDNA clones back to a yeast artificial chromosome (YAC) contig that spans over 600 kb surrounding the gene. The 5' end is just centromeric to the NotI site within the linking clone 17L1B, (Fountain, J. W. et al., *Amer. J. Hum. Genet.* 44:58–67 (1989); Fountain, J. W. et al., *Science* 244:1085–1087 (1989); Wallace, M. R. et al., *Nuclei Acids Res.* 17:1665–1667 (1989)), the first intron beginning only 81 basepairs from the NotI site. It extends through the position of a t(1;17) translocation breakpoint and beyond the position of a t(17:22) translocation breakpoint. Fountain, J. W. et al., *Science* 244:1085–1087 (1989); O'Connell, P. et al., *Science* 244:1087–1088 (1989). The transcript extends toward the telomere a minimum of 270 kb, beyond the NruI site. This site is seen only in the YAC clones, which are unmethylated, and thus must be methylated in genomic DNA. The most 3' clone isolated does not extend beyond the MluI site (also present only in the YAC clones), and defines a maximum gene size of 310 kb. The gene therefore extends between 270 and 310 kb. This assumes that the remainder of the 3' untranslated region yet uncloned exists in a single exon. All of the intron-exon borders of the gene have not yet been characterized, but by the number of bands on a genomic Southern blot it is estimated that it would contain in excess of 30 exons. The three previously described embedded genes (EVI2A, EVI2B, and OMgp) are transcribed from the opposite strand and are contained within a single intron. See Cawthon, R. et al., *Cell* 62:193–201, (1990); Cawthon, R. et al, *Genomics* 7:555–565 (1990); O'Connell, P. et al., *Science* 244:1087–1088 (1990); Mikol, D. D. et al., *J. Cell. Biol.* 110:471–479 (1990); Xu, G. et al., *Cell* 62:599–608 (1990); Xu, G. et al., *Cell* 63:835–841 (1990); Viskochil, D. et al., *Mol. Cell Biol.* 11, in press (1991).

Figure 13:
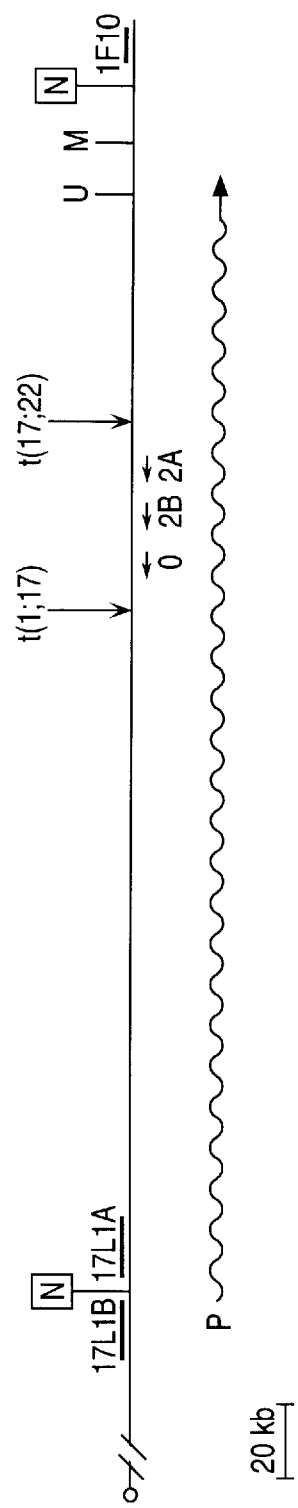
FIG. 13 shows the extent of the NF1 transcript on the genomic map of chromosome 17.

FIG. 13 details the data generated by mapping the cDNA clones against the YAC contig. The code for restriction sites is N for NotI, U for NruI and M for MluI. The boxed sites represent the positions of undermethylated CpG islands in genomic DNA.

E. Discussion of NF1 gene product: Tumor suppressor model

Initial partial sequences of the 3' end of the NF1 gene revealed little in the way of sequence homologies that could provide a clue to the function of the gene product. Cawthon, R. et al., *Cell* 62:193–201 (1990); Cawthon, R. et al., *Genomics* 7:555–565 (1990); Wallace, M. R. et al., *Science* 249:181–186 (1990). Further cloning and sequence analysis revealed homology to the mammalian GAP protein and yeast IRA1 and IRA2 gene products, which modulate the activity of the p21 ras protein in their respective hosts by accelerating the rate at which ras hydrolyzes GTP to become inactive ras-GDP. Ballester, R. et al., *Cell* 63:851–859 (1990); Buchberg, A. et al., *Nature* 347:291–294 (1990); Xu, G. et al., *Cell* 62:599–608 (1990); Xu, G. et al., *Cell* 63:835–841 (1990). This provided the first glimpse of the function of NF1; like GAP, it may be an upstream regulatory protein for ras (or a ras-related protein) with its normal function being to down-regulate a member of the ras family involved in mitogenic signal transduction. This model received further support when it was shown that the proposed GAP related domain of NF1 could complement loss of IRA function in yeast, and that it could stimulate ras-GTPase activity in vivo and in vitro. Ballester, R. M. et al., *Cell* 63:851–859 (1990); Martin, G. A. et al., *Cell* 63:835–841 (1990); Xu, G. et al., *Cell* 63:835–841 (1990).

An alternate model of ras-NF1 interaction postulates that NF1 may instead be a downstream effector for ras; a downstream model has also been proposed for the related GAP. Adari, H. et al., *Science* 240:518–521 (1988); Cales, C. et al., *Nature* 332:548–551 (1988); Hall, A., *Cell* 61:921–923 (1990); Yatani, A. et al., *Cell* 61:769–776 (1990). In this model the NF1 protein would be a target of activated ras, as a downstream member in the signal transduction cascade. Support for this model relies on the following observation. Both GAP and NF1 are thought to interact with ras p21 through its effector domain. Mutations in the putative ras effector domain inactivate the transforming ability of ras and prevent the GAP related domain of NF1 from GTPase activation (Martin, G. A. et al., *Cell* 63:843–849 (1990); Xu, G. et al., *Cell*, 835–841 (1990)), however, these studies require repetition with the full length protein. It also should be cautioned that recent work using a temperature sensitive effector domain mutant of ras has shown dissociation between stimulation of GTPase activity by GAP and the NF1 GAP domain and their role as ras effectors. DeClue, J. E. et al., *Mol. Cell. Biol* 11:3132–3128 (1991). This result is consistent with a ras effector molecule distinct from NF1 or GAP.

Nonetheless, the downstream effector model is attractive for its ability to account for the role of ras in certain cells of neuroectodermal origin. In the rat pheochromocytoma cell line PC12, activated ras induces differentiation and blocks proliferation. Bar-Sagi, D. et al., *Cell* 42:841–848 (1985); Noda, M. et al., *Nature* 318:73–75 (1985). Inhibition of ras in these cells blocks neural differentiation normally induced by nerve growth factor. Hagag, N. et al., *Nature* 319:680–682 (1986); Szeberenyi, J. et al., *Mol. Cell. Biol.* 10:5324–5332 (1990). Activated ras has also been shown to induce cell cycle arrest when introduced into rat Schwann cells Ridley, A. J. et al., *EMBO J.* 7:1635–1645 (1988). This is significant because Schwann cells may be the original cells that recruit other cell types in the formation of neurofibromas and neurofibrosarcomas. Ratner, N. et al., *Ann. Neurol.* 27:496–501 (1990); Sheela, S. et al., *J. Cell. Biol.* 111:645–653 (1990). Therefore, if NF1 is the the target (effector) of ras, then loss of NF1 function in Schwann cells could lead to a block of normal differentiation resulting in uncontrolled proliferation.

Either of these two models, the upstream regulatory protein or downstream effector model, are consistent with the NF1 being a tumor suppressor gene, with the phenotype being the result of loss of both alleles of the gene. Knudson, A. G., *Cancer Res.* 45:1437–1443 (1985). Previous studies of NF tumors did not always show a consistent loss of heterozygosity for NF1 in 17q11.2. Skuse. G. R. et al., *Genes Chrom. Cancer* 1:36–41 (1989); Menon, A. G. et al., *PNAS (USA)* 87:5435–5439 (1990); Glover, T. W. et al., *Genes. Chrom Cancer* 3:62–70 (1991). However, these interpretations were made difficult by frequent losses on 17p, apparently reflecting the major role that loss of the p53 gene plays in tumor progression in this disorder. Nigro, J. M. et al., *Nature* 342:705–708 (1989). More recent analyses have indicated that loss of heterozygosity involving only 17q can be demonstrated at least for some tumors. Skuse, G. R., *Science* 250:1749 (1990); Legius and Glover, personal communication; Ponder, personal communication. In those tumors not showing loss of heterozygosity, it is likely that the mutation in the second allele could be an independently acquired mutation.

The evidence that the NF1 gene is a tumor suppressor gene is strengthened by the unusual chromosomal aberration found in a sporadic case of NF1 described by Andersen, L. B. et al., *Cytogenet. Cell Genet.* 53:206–210 (1990). This patient shows the formation of a minichromosome by excision of the proximal region of 17q, which is lost in about 6% of somatic cells grown in culture. With one allele lost, this fraction of the somatic cells effectively become hemizygous for the NF1 gene. Subsequent somatic mutations can account for the second mutation and development of neurofibromas.

It is also possible that the second hit mutation may not be within the NF1 gene. Mutations within some other gene involved in the pathway toward development of benign neurofibromas may be in another as yet undefined locus. This would require that a gene dosage of one half be sufficient to cause the formation of neurofibromas. In this scenario the malignant neurofibrosarcomas may require both NF1 alleles to be mutated.

The complete sequencing of the NF1 protein product illustrates the lack of SH2 and SH3 domains in contrast to GAP. Homologous to non-catalytic regions of the oncogene src, these domains are thought to direct interactions with phosphotyrosine proteins involved in signal transduction. Koch, C. A. et al., *Science* 252:668–674 (1991). Their absence in NF1 implies that NF1 and GAP are not interchangeable in the cell, and that NF1 is probably not directly modulated through tyrosine phosphorylation by activated growth factor receptors. The potential sites for tyrosine and serine/threonine phosphorylation imply that intermediates activated receptors and NF1 may be involved in modulation of NF1 activity, since there is evidence that the NF1 protein is phosphorylated on serine and threonine (Downward, personal communication).

A potential candidate for this intermediate could be one of the members of the ERK family, which are activated by tyrosine phosphorylation by nerve growth factor and are themselves serine/threonine protein kinases. Boulton, T. G. et al., *Cell* 65:663–675 (1991). Certainly, the large size of the product in relation to the small portion conferring GAP activity indicates that other domains may be involved in modulating the ras-GTPase activity of this protein, or carrying out entirely different functions. The fact that sequence homology with yeast IRA1 and IRA2 extends beyond the GAP catalytic domain toward both termini indicates that there may be more extensive functional homology with these members of the GAP family. Statistical analysis has also shown NF1 to be more closer related to IRA2 than IRA1. It may be useful to think of the NF1 product as consisting of three domains: an amino-terminus of unknown function, a GAP-related middle domain, and a carboxy-terminus related to the IRA1 and IRA2 gene products. Unfortunately, the functions of these domains of the IRA gene products are not known even in this simple eukaryote. For NF1, interaction with other factors in the pathway leading to differentiation, such as the low-affinity nerve growth factor receptor and the trk oncogene product, or factors that mediate between these and NF1, may be localized to these yet undefined regions. Interactions at these other domains may also ultimately provide a clue as to the reasons why a mutation in a ubiquitously expressed gene reveals its character predominantly in cells derived from the embryonic neural crest.

Although it is presently unclear how the alternatively spliced transcripts play their unique role in NF1 function, in some tissues their expression is not mutually exclusive. These alternative forms may play a role in the diverse clinical manifestations of the disorder. Germline mutations in some of the alternatively spliced exons may give rise to some of the more unusual NF1 phenotypes.

The large NF1 transcript and 300 kb gene size represent a large target for mutations. Assuming that the NF1 phenotype results from loss of function mutations, causative mutations may be dispersed throughout the coding and regulatory region. In the patients surveyed thus far, this seems to be the case. Cawthon, R. et al. *Cell* 62:193–201 (1990); Viskochil, et al., personal communication; The size of the gene alone however, cannot fully account for the high mutation rate. At best, the possible target size is only a factor of 10 larger than other genes, whereas the mutation rate is about 100 fold higher than what is usual for a single locus, with the majority of new mutations of paternal origin. Jadayel, D. et al., *Nature* 343:558–559 (1990). It remains to be determined whether paternal germline DNA is more mutable due to methylation patterns associated with genomic imprinting.

SPECIFIC EXAMPLE 3

I. Materials and Methods

A. Peptides and fusion proteins

Peptides D (SQVQKQRSAGSFKRNSIKKIV; residues 2798–2818 of SEQ ID NO:2) and H (CNPRKQGPETQGSTAELIT; residues 509–528 of SEQ ID NO:2) were synthesized and conjugated to keyhole limpet hemocyanin at a coupling ratio of 13:1. Each peptide synthesized was verified by analysis of the amino acid composition. Fusion proteins were produced by subcloning the appropriate cDNA fragment into the pMAL(c) vector (New England BioLabs) so that the reading frame was maintained. pMAL.B3A is a 219 nt PstI-HindIII fragment (residues 2746–2819) of the NF1 cDNA containing a 73 amino acid open reading frame and the natural termination codon (Marchuk, D. A. et al, manuscript submitted). pMAL.HF3A.P is a 918 nt HpaI-PstI fragment (residues 65–371) while pMAL.HF3A.X is a 3523 nt HpaI-XhoI fragment (residues 65–1240) of the NF1 cDNA. The fusion protein constructs were verified by restriction enzyme analysis before transformation into host BL21(DE3) cells. These cells were grown to an $OD_{600}$ of 0.6 in Luria broth and induced in 0.4 mM isopropyl-b-D-thiogalactoside (IPTG) for 3 hours. Cells were solubilized in Laemmli buffer by boiling for 10 minutes and analyzed on SDS polyacrylamide gels. Studier, F. W. et al., *Meth. Enzymol.* 185:60–69 (1990).

B. Antisera

Female rabbits (4 kg) were initially injected with either 500 micrograms of purified peptide or 250 micrograms of fusion protein embedded in emulsified polyacrylamide gel slices in complete Freund's adjuvant and boosted every four to six weeks with the same amount of antigen in incomplete Freund's adjuvant. Preimmune and immune sera were collected by ear venupuncture, allowed to clot and centrifuged at 2500 rpm for 15 minutes. Thimerisol was added as a preservative at a final concentration of 0.01% and the antisera was stored at −20° C.

C. Radiolabeling and cell Lysis $2 \times 10^6$ cells were incubated overnight in growth media and then labeled with $^{35}$S-methionine by incubating cells in 2 ml methionine-free media containing 0.25 mCuries of labeling-grade $^{35}$S-methionine (Amersham) per milliliter media overnight. Cells were washed once in phosphate-buffered saline, pH 8 and lysed in modified RIPA buffer (150 mM NaCl, 50 mM Tris-HCl, pH7.5, 1% Nonidet P-40, 0.25% sodium deoxycholate, 2 mM EGTA, 1 mM phenylmethanesulfonyl fluoride, 1 mM leupeptin and 0.1 mM apronitin) for 20–30 minutes at 4° C. Lysates were then clarified by centrifugation at 14,000 rpm for 10–15 minutes. Harlow, E. et al., *Antibodies: A Laboratory Manual*, Cold Spring Harbor, N.Y. pp. 421–470 (1988).

Whole cell lysates were prepared in a similar fashion. Cells were lysed in modified RIPA buffer at a density of $10^7$ cells/ml lysis buffer at 4° C. for 20 minutes and then clarified. Mouse tissue homogenates were prepared from freshly harvested organs by extensive homogenization using a Dounce tissue grinder and repeated passage through a 20 gauge needle prior to lysis in modified RIPA buffer at 4° C. for 20 minutes. Lysates were then clarified by centrifugation at 14,000 rpm for 10–15 minutes. The amount of protein was determined by Biorad Protein Assay according to the protocol specified by the manufacturer.

D. ELISA and immunoprecipitation

Enzyme-linked immunosorbent assays (ELISA) were performed using horseradish peroxidase-conjugated goat anti-rabbit antibodies (Bethesda Research Laboratories, Bethesda, Md.) as per the manufacturer's specifications. All rabbit sera were tested by ELISA against the immunizing antigen, KLH and an irrelevant antigen. ELISA plates were coated overnight with antigens, KLH, and IgG positive controls prior to blocking with 2% bovine serum albumin (Sigma) in PBS for 2 hours. Antisera was added over a dilution range of 1:50 to 1:80,000 for 90 minutes. Goat anti-rabbit horseradish peroxidase (HRP) conjugate (IgG heavy and light; Bethesda Research Laboratories) was added for 1 hour after washing in PBS. The ELISA was developed with o-phenylene-diamine (Zymed) in citrate buffer (0.05M citric acid, 0.1M $NaH_2PO_4$, pH 5.0) and 0.03% hydrogen peroxide. Results were analyzed on a Dynatech MR650 96 well plate reader at an optical density of 490 nm.

Cells were lysed as described in the previous section, cleared by centrifugation in a microfuge at 14,000 g for 15 minutes and then incubated with rabbit antisera for 2 hours at 4 degrees Centigrade. Sepharose protein A beads (Pharmacia CL4B) were added and incubated for an additional 2 hours with regular agitation. Immunoprecipitates were washed twice in buffer 1 (10 mM $NaPO_4$, pH 7.6; 100 mM NaCl; 1 mM EDTA, 1% Triton X-100; 0.5% sodium deoxycholate; 0.1% SDS), twice in buffer 2 (20 mM Tris-HCl, pH 8.3; 250 mM NaCl; 1% Nonidet P-40; 0.1% SDS) and then twice more in buffer 1 before Laemmli buffer was added. The samples were then boiled for 5 minutes and loaded onto SDS polyacrylamide gels for analysis. Harlow, E. et al., *Antibodies: A Laboratory Manual*, Cold Spring Harbor, N.Y., pp. 421–470 (1988).

E. SDS-PAGE and Western blot analysis

Samples were separated by standard SDS-polyacrylamide gel electrophoresis (Loemmli, U. K., *Nature* 227:680–685 (1970)) and transferred overnight in modified Towbin transfer buffer (50 mM Tris-HCl, 380 mM glycine; 18) with 10% methanol at 250–750 milliamps. Nitrocellulose (Gelman, Ann Arbor, Minn.) or polyvinylene fluoride (PVDF) Immobilon (Millipore) membranes were used for Western transfer as per the manufacturer's specifications. Filters were washed in PBS and stained with Ponceau-S.

Western blot analysis was performed using either alkaline phosphatase (AP) or horseradish peroxidase (HRP) conjugated secondary antibodies as per the manufacturer's recommendations. Filters were blocked overnight in 5% ovalbumin-TBST prior to Western blot analysis. All antibodies were diluted in 2% ovalbumin (Sigma, St. Louis, Mo.), grade IV) with TBST (20 mM Tris-HCl, pH 7.5, 150 mM NaCl, 0.05% Tween). Membranes were incubated with anti-peptide sera for 1–2 hours at room temperature, washed four times in TBST, incubated with the appropriate secondary AP or HRP conjugated antibodies for 1 hour at room temperature and then washed four times in TBST. Development was performed using 5-bromo-4- chloro-3-indolyl phosphate with nitroblue tetrazolium (AP method: Sigma) or 4-chloro-1-naphthol (Sigma) and 0.03% hydrogen peroxide (HRP method).

F. Purification of antibodies

Three techniques have been used in our laboratory to purify mouse or rabbit antibodies from whole sera and can be applied to purify the antisera described above. The first method involves the use of a Protein A-Sepharose column. This column will bind immunoglobulins of predominantly the IgG class which can then be eluted from the column using 0.1M glycine pH 2–3. After Protein A column purification antibodies are predominantly of the IgG class and may be further purified by affinity purification. The second technique involves affinity purification of antibodies through the use of a peptide-Sepharose column. The peptide originally used as an immunogen in rabbits or mice is coupled to activated Sepharose beads and extensively washed. Sera from rabbits or mice is applied to these columns and eluted as before. The resulting eluate should contain only antibodies which react to the peptide used as an immunogen. Alternatively, when fusion proteins are used as immunogen, the immunizing fusion protein is separated from total *E. coli* cell proteins by SDS-polyacrylamide gel electrophoresis prior to transfer to nitrocellulose membranes. The fusion protein is visualized on the nitrocellulose membrane by Ponceau-3 staining and then cut out for immunoadsorption. Antibodies directed against the fusion protein are eluted in glycine buffer after adsorption to these nitrocellulose strips. The resulting eluate should contain only antibodies which recognize the fusion protein immunogen.

II. Results

A. Fusion proteins

Figure 15:
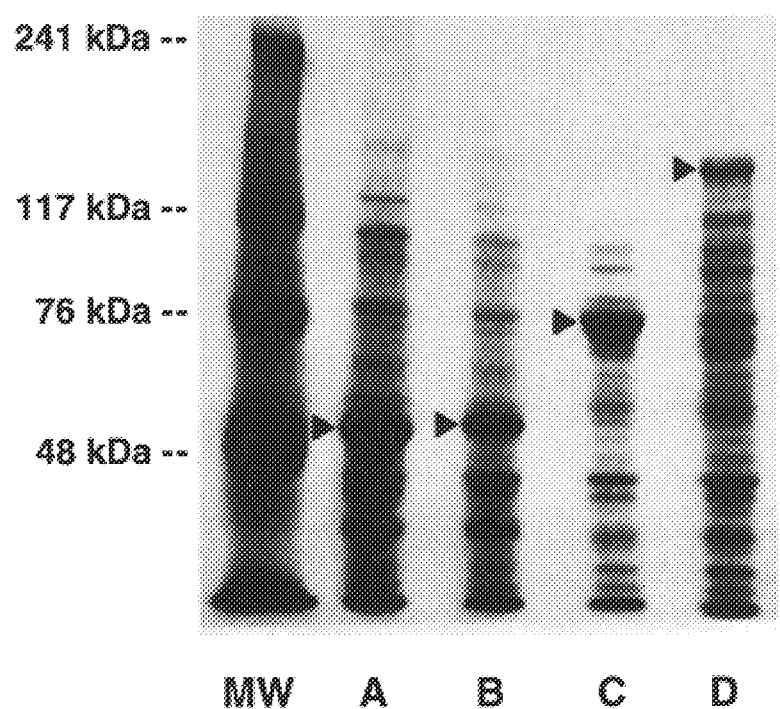
FIG. 15 are SDS-PAGE results showing the expression of pMAL(c) fusion proteins.

Fusion proteins generated using the pMAL(c) expression vector were analyzed by SDS-PAGE to determine whether the desired fusion protein was expressed. Cell extracts were prepared as described in the Materials and Methods section and separated by 7.5% SDS-PAGE. Fusion proteins were detected by Coomassie Blue staining. Overexpression of pMAL.HF3A.X, pMAL.HF3A.P, and pMAL.B3A is shown in FIG. 15: (A) 25 microliters of pMAL vector alone expressing the maltose-binding protein (B) 25 microliters of pMAL.B3A, (C) 50 microliters of pMAL.HF3A.P, and (D) 50 microliters of pMAL.HF3A.X fusion proteins are over-expressed with yields ranging between 0.25 to 2.0 mg/ml. Molecular weight size standards were run in the first lane. Fusion proteins are denoted by the arrows. The yield of fusion protein per microliter of bacterial cell lysate varied depending on the size of the fusion protein. pMAL(c) vector alone and pMAL.B3A typically yielded 1–2 mg/ml fusion protein whereas the pMAL.HF3A series yielded 0.25–0.5 mg/ml fusion protein.

B. Antisera recognize a 250 kDa protein

The antisera raised in rabbits against peptides D and H as well as the pMAL.B3A fusion protein identified a unique protein which migrates as a 250 kDa species. Immunoprecipitation, with the results depicted in FIG. 16(A), was conducted as follows: HeLa cells were radiolabeled with $^{35}$S-methionine overnight and lysates were immunoprecipitated with H and D peptide antisera. 500 microliters of lysate was incubated with 8 microliters of sera prior to the addition of 35–40 microliters of 50% Protein-A Sepharose CL-4B beads. Precipitates were separated by 7.5% SDS-PAGE, fixed in 25% isopropanol-10% acetic acid, dried down and exposed on Kodak film at −70° C. for 3 days. The lanes in FIG. 16(A) contained the following: lane 1, preimmune D peptide serum; lane 2, immune D peptide serum; lane 3, preimmune H peptide serum; lane 4, immune H peptide serum. Molecular size standards are indicated on the left margin.

The Western blot shown in FIG. 16(B) was prepared as follows: HeLa cells were lysed, separated by 7.5% SDS-PAGE and transferred to PVDF membranes prior to Western blot analysis using H peptide and pMAL.B3A fusion protein sera at a 1:1000 dilution. Alkaline phosphatase conjugated goat anti-rabbit antibodies (Cappell) were used at a 1:3000 dilution. The lanes in FIG. 16(B) contained the following: lane 1, preimmune H peptide serum; lane 2, immune H peptide serum; lane 3, preimmune pMAL.B3A fusion protein serum; lane 4, immune pMAL.B3A fusion protein serum. The arrows point to the 250 kDa NF1GRP. Molecular size standards are indicated on the left margin.

Figure 16A:
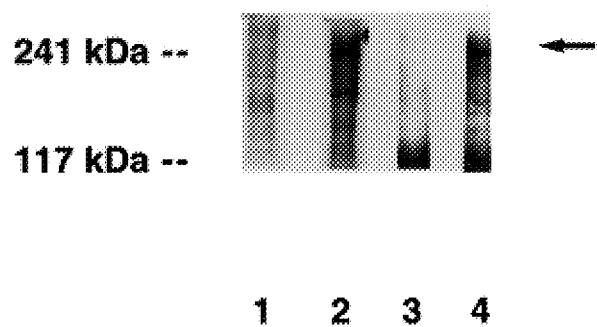
FIG. 16 are (A) SDS-PAGE results after immunoprecipitation and (B) a Western blot analysis illustrating that H and D peptide antisera recognize a 250 kDa protein.
Figure 16B:
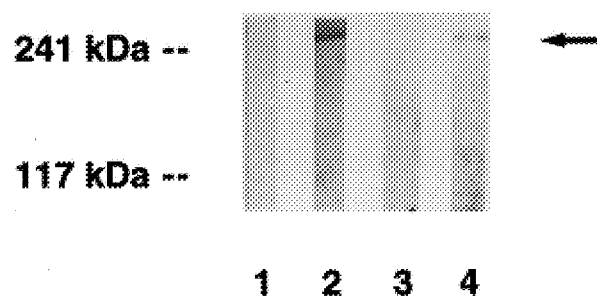
Figure 17:
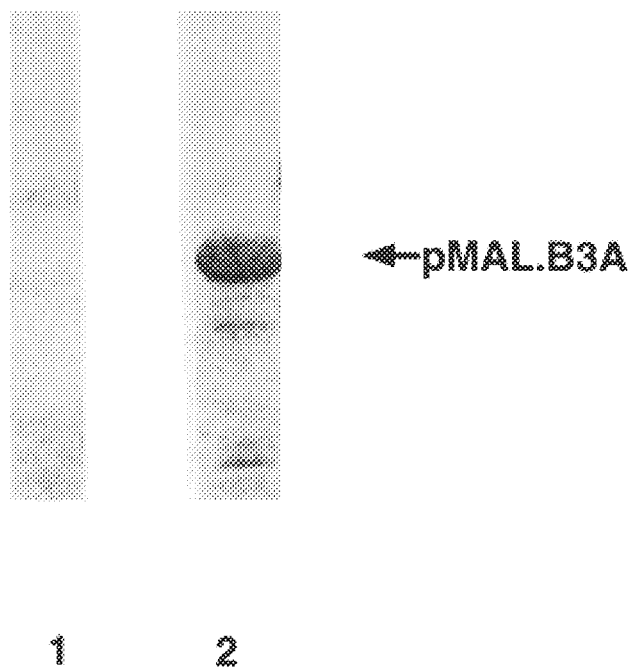
FIG. 17 is a Western blot illustrating that D peptide antiserum recognizes an independently generated fusion protein.

As shown in FIG. 16, immune H peptide antisera detects a 250 kDa protein by immunoprecipitation of the $^{35}$S-methionine radiolabeled tissue culture cells (FIG. 16A, lane 4) as well as by Western immunoblotting against the whole cell lysates transferred onto Immobilon or nitrocellulose filters (FIG. 16B, lane 2). There also appear to be other protein bands which are not consistently seen. At this time, we cannot exclude the possibility that these other proteins represent degradation products of the protein, alternative forms of the protein, or co-migrating species. The fact that incubation of the H and D peptide antisera with their respective peptides eliminates immunoprecipitation and Western blot detection of the 250 kDa protein but not the other protein bands support the conclusion that these additional proteins are not related to the NF1 gene product.

Antisera raised against the D peptide likewise detect a unique protein migrating at 250 kDa by immunoprecipitation of radiolabeled cells (FIG. 16A, lane2). However, Western immunoblotting using this antisera does not reproducibly identify unique proteins. Antisera raised against the pMAL.B3A fusion protein detects a unique protein migrating at 250 kDa by Western blotting (FIG. 16B, lane 4). This 250 kDa protein has been identified in all tissues examined, including brain, Schwann cells, fibroblasts, lymphocytes, hepatocytes, erythroleukemia cell lines, and melanoma cell lines. It has also been identified in human, mouse and rat cells. No cell line tested to date has failed to express this protein. There also does not appear to be major quantitative variation between the various cell lines examined.

C. Antisera recognize independently generated fusion proteins

In order to demonstrate that the protein identified actually represents the NF1 gene product, we tested the antisera described above against fusion proteins which contain the amino acid sequence used to synthesize the peptides. Three fusion proteins were generated by ligating a portion of the NF1 cDNA into the fusion protein vector, pMAL(c). As shown in the fusion protein and synthetic peptide map in FIG. 14, two of these fusions (pMAL.HF3A) represent a discriminatory set, one which contains the H peptide epitope (pMAL.HF3A.X) and another which does not (pMAL.HF3A.P) the catalytic domain is defined as the 412 amino acids between residues 1125 and 1537. The other fusion protein, pMAL.B3A, contains the D peptide epitope.

Figure 14:
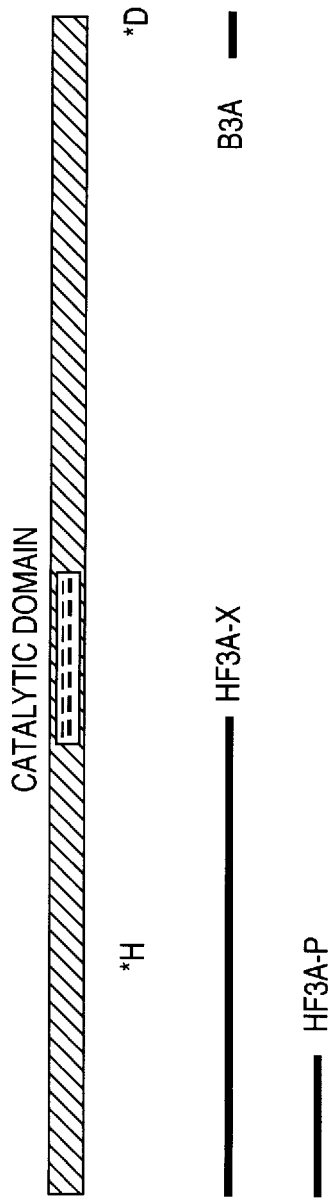
FIG. 14 is a map of the NF1 gene product with the positions of the fusion proteins and synthetic peptides.

As can be seen in FIG. 14, the D peptide sera recognizes the pMAL.B3A fusion protein. BL21(DE3) cells containing the pMAL.B3A plasmid were induced in IPTG for 3 hours and lysates prepared. 50 microliters of whole cell lysate were added in each lane and separated by 7.5% SDS-PAGE prior to transfer to PVDF membranes. Western blot analysis was performed using 1:5000 dilutions of the D antisera and developed using alkaline phosphatase method. Immune (lane 2) but not preimmune (lane 1) D peptide serum recognizes the pMAL.B3A fusion protein. Migration of the fusion protein is indicated on the right panel as detected by Ponceau-S staining (arrow).

Likewise, H peptide antisera recognizes the pMAL.HF3A.X fusion protein, but not the pMAL.HF3A.P fusion protein which lacks the H peptide epitope by Western blotting (data not shown).

D. Antisera recognize the same 250 kDa protein

Figure 18:
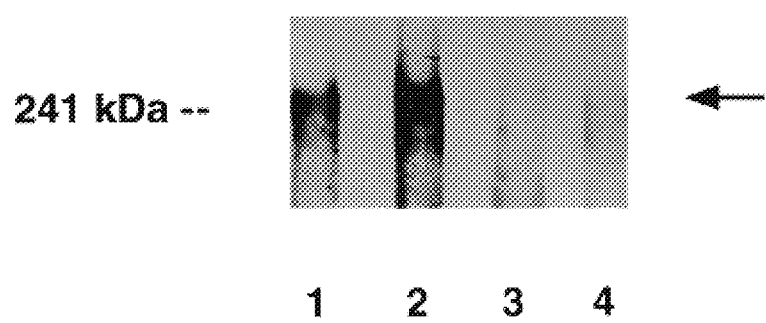
FIG. 18 are SDS-PAGE results illustrating that pMAL.B3A fusion protein and H peptide antisera recognize the same proteins precipitated by D peptide antiserum.

In order to confirm that the protein recognized by the D peptide, H peptide and pMAL.B3A fusion protein antisera represented the same protein, mouse brain lysates were immunoprecipitated using H peptide antisera and transferred to Immobilon for Western blot analysis using the pMAL.B3A fusion protein antisera. As can be seen in FIG. 18, the immune pMAL.B3A fusion protein antiserum recognized the same protein species precipitated by the H peptide antisera and both H peptide and pMAL.B3A fusion protein antisera recognize the same protein precipitated with the D peptide antiserum. Mouse brain lysates were immunoprecipitated with immune D peptide sera (1:60 dilution of antisera), separated by 7.5% SDS-PAGE and visualized by Ponceau-S staining after transfer to PVDF membranes. The immune H peptide (lane 1) and pMAL.B3A fusion protein (lane 2) sera (1:1000 dilution) detected the 250 kDa protein seen in precipitates by Western blot analysis using the alkaline phosphatase detection method. The preimmune serum did not recognize the 250 kDa protein (lane 3).

Preincubation of H peptide antiserum with 10 micrograms of purified H peptide for 2 hours at 4° C. inhibited the recognition of the immunoprecipitated protein (lane 4). Molecular size standards are indicated on the left margin.

E. NF1 protein expressed in adult mouse tissues

Figure 19:
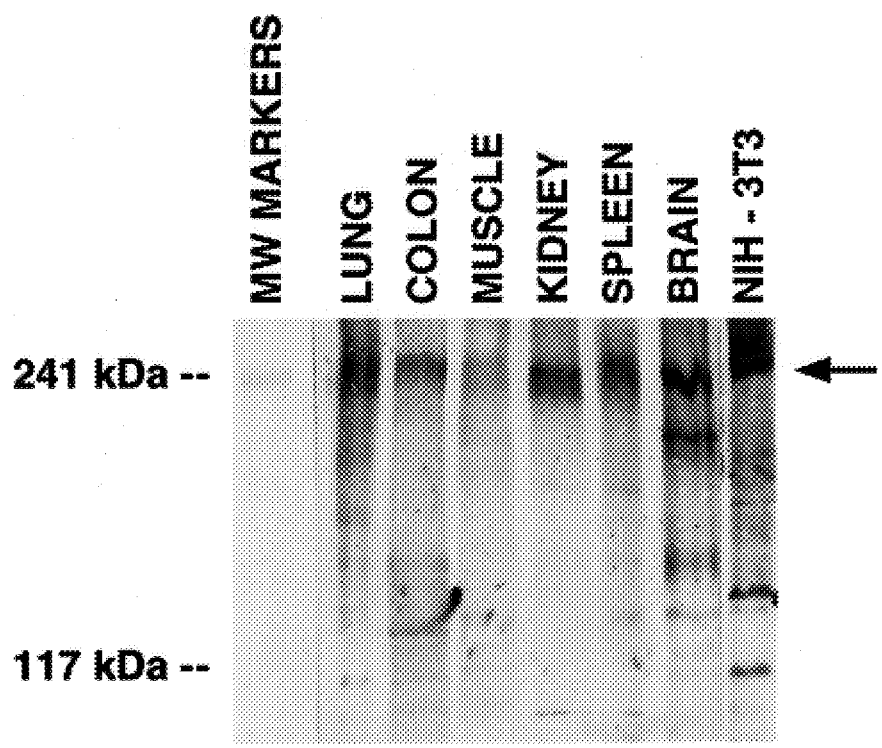
FIG. 19 are SDS-PAGE results illustrating that pMAL.B3A fusion protein antiserum detects the NF1 protein in a variety of adult mouse tissues.

The expression of the NF1 protein in adult mouse tissues was investigated by homogenizing a survey of tissues from freshly euthanized adult female mice. Equivalent amounts (100 micrograms) of total tissue extract were separated by electrophoresis on 7.5% SDS-polyacrylamide gels, transferred to PVDF membranes and stained with Ponceau-S to verify equivalent loading of total protein prior to Western blotting. Using the pMAL.B3A fusion protein antiserum (1:100 dilution), the 250 kDA NF1 protein was detected in brain, lung, spleen, kidney, muscle, and colon as indicated at the arrows in FIG. 19. Molecular size is indicated on the left margin. Similar results were obtained using the H peptide antiserum. Although differences between the various tissues examined by Western blotting are evident, there are minor variations in quantities detected from experiment to experiment which preclude quantitative comparisons.

F. Discussion of NF1 gene product

Although von Recklinghausen neurofibromatosis (NF1) is a disorder involving neural crest-derived tissues, NF1 mRNA appears to be ubiquitously expressed. Wallace, M. R. et al., *Science* 249:181–186 (1990). The level of tissue specificity might reflect either tissue-specific expression or tissue-specific interactions of the NF1 gene product with other signal transduction proteins. It is possible that the levels of the NF1 protein are significantly greater in neural crest-derived tissues or that it is post-translationally modified (phosphorylation, myristylation, etc.) in a tissue-specific manner. Conversely, the tissue specificity may reflect the association of the NF1 protein with other signal transduction molecules which are expressed predominantly in the neural crest. Possible candidates include nerve growth factor receptor (Klein, R. et al., *Cell* 65:189–197 (1991)), the trk protooncogene protein (Hempstead, B. L. et al., *Nature* 350:378–683 (1991)), ERK1 (Boulton, T. G. et al., *Cell* 65:663–675 (1991)), and AP2 (Mitchell, P. J. et al., *Genes and Development* 5:105–119 (1991)).

The NF1 protein, like the mRNA, appears to be ubiquitously expressed and displays species conservation in mouse and rat. It is detectable by Western blotting using two different antisera in brain, lung, kidney, liver, spleen, muscle and colon. These findings are in complete agreement with Northern blot data demonstrating NF1 mRNA in mouse liver, kidney and brain. Buchberg, A. M. et al., *Nature* 347:291–294 (1990). The protein is very hydrophilic, based on computer analysis of its predicted amino acid sequence and most likely resides in the cytoplasm. The protein also has a relatively slow turnover rate, in that metabolic labeling for 4–8 hours has failed to detect appreciable quantities of radiolabeled protein by immunoprecipitation, whereas labeling for 12–18 hours detects the protein.

The open reading frame of the NF1 cDNA predicts a protein of 2818 amino acids and a molecular weight of 327 kDa. Marchuk, D. A. et al., manuscript submitted. The size discrepancy observed may be the result of anomalous migration as seen in the cystic fibrosis transmembrane conductance regulator protein which migrates as a 140 kDa protein despite the predicted 185 kDa size. Alternatively, the difference could reflect post-translational modifications, such as processing of a pro-protein species. This would necessarily involve cleavage of amino terminal sequences, as the D peptide and pMAL.B3A fusion protein antisera which recognize carboxy terminal residues identify the same 250 kDa protein as the more amino terminal H peptide antiserum. Although evidence exists for alternative splicing in the amino terminal portion of the NF1 mRNA, the demonstration that these alternative forms are actually translated into unique protein species awaits more directed experiments. The fact that the H and D peptide antisera recognize independently generated fusion proteins with overlapping epitopes and recognize the same protein by immunoprecipitation and Western blotting is strong evidence that the protein identified is the authentic NF1 gene product. Furthermore, using antisera directed against catalytic domain epitopes, it has been demonstrated that the NF1 protein identified by our antisera is identical to the protein product later identified by others.

As previously discussed, the homology between a small portion of the NF1 gene product and the catalytic domain of a family of proteins with GTPase activity suggests that the NF1 gene product may also interact with ras. Tanaka, K. et al., *Cell* 60:803–807 (1990); Hall, A., *Cell* 61:921–923 (1990). Previous experiments have demonstrated that the NF1 catalytic domain (residues 1125–1537 of the full length cDNA predicted amino acid sequence) is able to replace yeast IRA1 and IRA2 in restoring the wild type phenotype in ira1$^-$, ira2$^-$ yeast strains as well as catalyze the conversion of wild-type, but not mutant, ras-GTP to ras-GDP. Ballester, R. M. et al., *Cell* 63: 851–859 (1990); Xu, G. et al., *Cell* 63:835–841 (1990).

It is proposed that future reference to the NF1 protein be to NF1-GAP-related protein (NF1GRP) to underscore what is known about the protein and to avoid confusion with the NF1 transcriptional factor, the neurofilament proteins and the neurofibrillary tangles of Alzheimers disease. It will also be appreciated that, within the scope of the invention claimed herein, the term gene product is meant to include both unmodified translated forms and any post-translationally modified forms (e.g., glycosylated, phosphonylated, cleaved, etc.) of the NF1GRP protein.

APPLICATIONS

As previously discussed, NF1 is a disease of high frequency and high mutation rate. Screening for NF1, particularly in neonates and young children who are often asymptomatic, is thus one of the major applications of the present invention. Since the NF1 gene is ubiquitously expressed, test samples of the subject can be obtained from a variety of tissues or blood. An NF1 test can also be included in panels of prenatal tests since NF1 DNA, RNA or protein can also be assed in amniotic fluid. It will be appreciated that, since NF1 is a dominant disorder, individuals which are heterozygous for NF1 may still express NF1 at 50% or reduced levels. Quantitative testing for NF1 transcript and gene product is thus also contemplated within the scope of the present invention.

Nucleic acid and protein-based methods for screening and diagnosing NF1 are all contemplated to be within the scope of the present invention. For example, knowing the sequence of the NF1 gene, DNA or RNA probes can be constructed and used to detect NF1 mutations through hybridization with genomic DNA in tissue or blood using conventional techniques. RNA or cDNA probes can be similarly probed to screen for NF1 mutations or for quantitative changes in expression. A mixture of different probes, i.e. "probe cocktail", can also be employed to test for more than one mutation.

With respect to nucleic acid-based testing, genomic DNA may be used directly for detection of specific sequence or may be amplified enzymatically in vitro by using PCR (Saiki, et al., *Science* 230:1350–1353 (1985); Saiki, et al., *Nature* 324:163–166 (1986)) prior to analysis. Recent reviews of this subject have been presented by Caskey, *Science* 236:1223–1228 (1989) and by Landergren, et al., *Science* 242:229–237 (1989). The detection of specific DNA sequence may be achieved by methods such as hybridization using specific oligonucleotides (Wallace, et al., *Cold Spring Harbour Symp. Quant. Biol.* 51:257–261 (1986)), direct DNA sequencing (Church, et al., *PNAS (USA)* 81:1991–1995 (1988)), the use of restriction enzymes (Flavell, et al., *Cell* 15:25 (1978); Geever, et al., *PNAS (USA)* 78:501 (1981)) discrimination on the basis of electrophoretic mobility in gels with denaturing reagent (Myers, et al., *Cold Spring Harbour Sym. Quant. Biol.* 51:275–284 (1986)), RNase protection (Myers, R. M. et al., *Science* 230:1242 (1985)), chemical cleavage (Cotton, et al., *PNAS (USA)* 85:4397–4401 (1985)), and the ligase-mediated detection procedure (Landergren, et al., *Science* 241:1077 (1988)).

With respect to protein-based testing, antibodies can be generated to the NF1 gene product using standard immunological techniques, fusion proteins or synthetic peptides as described herein. Monoclonal antibodies can also be produced using now conventional techniques such as those described in Waldmann, T. A., *Monoclonal Antibodies in Diagnosis and Therapy, Science* 252:1657–1661 (1991) and Harlow, E. et al., *Antibodies:A Laboratory Manual:*Cold Spring Harbor, N.Y. (1988). It will also be appreciated that antibody fragments, i.e. Fab' fragments, can be similarly employed. Immunoassays, for example ELISAs, in which the test sample is contacted with antibody and binding to the gene product detected, can provide a quick and efficient method of determining the presence and quantity of NF1 gene product.

With the characterization of the NF1 gene product and its function, functional assays can also be used for NF1 diagnosis and screening and to monitor treatment. For example, enzymatic testing to determine levels of gene function, rather than direct screening of the NF1 gene or product, can be employed. Testing of this nature has been utilized in other diseases and conditions, such as in Tay-Sachs. In the case of NF1, the NF1 protein can be assessed, for example, for its ability to catalyze the conversion of ras protein from its GTP to its GDP form. See Ballester, R. M. et al., *Cell* 63:851–859 (199); Martin, G. A. et al., *Cell* 63:835–849 (1990).

Identification of the NF1 gene and its gene product also has therapeutic implications. In conventional replacement therapy, gene product or its functional equivalent is provided to the patient in therapeutically effective amounts. NF1 protein can be purified using conventional techniques such as those described in Deutcher, M. (editor), *Guide to Protein Purification. Meth. in Enzymol.* Vol. 182 (1990). Sufficient amounts of gene product or protein for treatment can be obtained, for example, through cultured cell systems or synthetic manufacture. Drug therapies which stimulate or replace the gene product can also be employed. Delivery vehicles and schemes can be specifically tailored to the particular protein or drug being administered.

Treatment can also take the form of modulation of the function of a defective protein or by modification of another protein or step in the pathway in which NF1 participates in order to correct the physiological abnormality. For example, since NF1 appears to act as a brake on the effects of activated ras protein, in the absence of NF1 (as would be expected to occur in a tumor in an NF1 patient) a useful approach would be to down-regulate ras. One method by which this could be accomplished would be through the use of an inhibitor of pharnesyl transferase. See Gibbs, J. B., *Cell* 65:1–4 (1991).

Modulation of NF1 function can be accomplished by the use of therapeutic agents or drugs which can be designed to interact with different aspects of NF1 protein structure or function. For example, a drug or antibody can bind to a structural fold of the protein to correct a defective structure. Alternatively, a drug might bind to a specific functional residue and increase its affinity for a substrate or cofactor. Efficacy of a drug or agent can be identified by a screening program in which modulation is monitored in vitro in cell systems in which a defective NF1 protein is expressed. Alternatively, drugs can be designed to modulate NF1 activity from knowledge of the structure and function correlations of NF1 protein and from knowledge of the specific defect in the various NF1 mutant proteins. See Capsey, et al., *Genetically Engineered Human Therapeutic Drugs*, Stockton Press, New York (1988).

Gene therapy using recombinant technology to deliver the gene into the patient's cells or vectors which will supply the patient with gene product in vivo is also contemplated as within the scope of the present invention. Retroviruses have been considered a preferred vector for experiments in somatic gene therapy, with a high efficiency of infection and stable integration and expression (Orkin, et al., *Prog. Med. Genet.* 7:130 (1988)). For example, NF1 gene cDNA can be cloned into a retroviral vector and driven from either its endogenous promoter of from the retroviral LTR (long terminal repeat). Other delivery systems which can be utilized include adeno-associated virus (AAV) (McLaughlin, et al., *J. Virol.* 62:1963 (1988), vaccinia virus (Moss, et al., *Annu. Rev. Immunol.* 5:305 (1987)), bovine papilloma virus (rasmussen, et al., *Meth. Enzymol.* 139:642 (1987)), or member of the herpesvirus group such as Epstein-Barr virus (Margolskee, et al., *Mol. Cell. Biol.* 8:2937 (1988)). Finally, since a defect in the NF1 gene results in the unbridled proliferation of nervous tissue, identification of the gene and gene product may be useful in developing treatments for non-NF1 tumors of the nervous system. Since the NF1 gene product appears to function as a tumor suppressor, increasing the supply of the product may have a beneficial effect on such tumors. Conversely where increased proliferation of nervous tissue would be advantageous, strategies to decrease production of the NF1 product might prove beneficial.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. An isolated amino acid sequence comprising SEQ ID NO.4.

2. An isolated amino acid sequence translated from a purified NF1 transcript.

3. An isolated amino acid sequence comprising SEQ NO.2.

4. An isolated NF1 protein.

5. The protein of claim 4 having a length of about 2818 amino acids.

6. The protein of claim 4 having a molecular weight of about 250 kDa as determined by immunoprecipitation or Western blotting with H peptide, D peptide or pMAL(c) fusion protein antiserum.

7. The protein of claim 4 wherein the product is not of in vivo origin.

8. An isolated NF1 protein exhibiting the following characteristics:
 a. immunorecognition by H peptide-specific antiserum, D peptide-specific antiserum and pMAL(c) fusion protein-specific antiserum;
 b. a molecular weight of approximately 250 kDa as determined by immunoprecipitation or Western blotting with H peptide, D peptide or pMAL(c) fusion protein antiserum; and
 c. hydrophilic.

9. An isolated NF1 polypeptide comprising amino acid 1 to amino acid 610 of the sequence shown in SEQ ID NO. 4.

10. An isolated NF1 polypeptide comprising amino acid 524 to amino acid 610 of the sequence shown in SEQ ID NO. 4.

11. An isolated NF1 polypeptide comprising amino acid 1125 to amino acid 1537 of the sequence shown in SEQ ID NO. 2.

12. An isolated NF1 polypeptide comprising amino acid 2746 to amino acid 2818 of the sequence shown in SEQ ID NO. 2.

13. An isolated NF1 polypeptide comprising amino acid 65 to amino acid 371 of the sequence shown in SEQ ID NO. 2.

14. An isolated NF1 polypeptide comprising amino acid 65 to amino acid 1240 of the sequence shown in SEQ ID NO. 2.

15. An isolated NF1 polypeptide comprising amino acid 2798 to amino acid 2818 of the sequence shown in SEQ ID NO. 2.

16. An isolated NF1 polypeptide comprising amino acid 509 to amino acid 528 of the sequence shown in SEQ ID NO. 2.

17. An isolated NF1 polypeptide comprising the sequence shown in SEQ ID NO. 9.

18. An isolated NF1 polypeptide comprising the sequence shown in SEQ ID NO. 11.

* * * * *

UNITED STATES PATENT AND TRADEMARK OFFICE
CERTIFICATE OF CORRECTION

PATENT NO : 5,859,195           Page 1 of 2

DATED : January 12, 1999

INVENTOR(S) : Francis S. Collins et al.

Figure 5A:
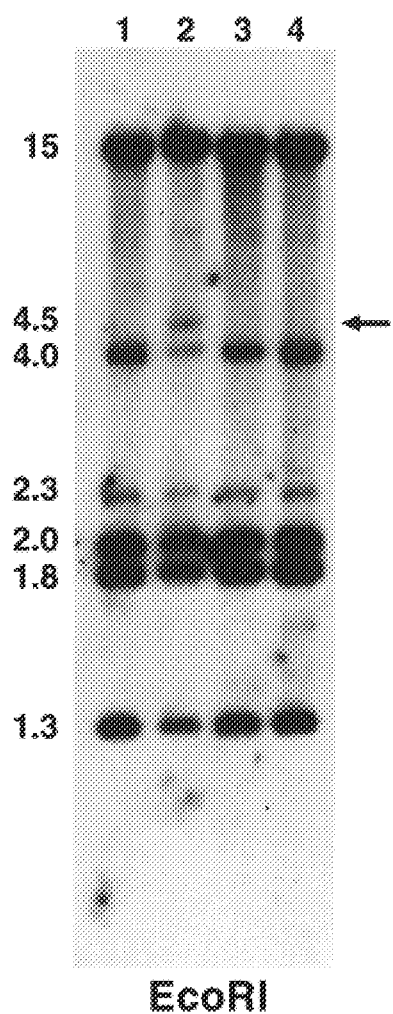
FIG. 5A–D are Southern blots of the DNA of a new mutation NF1 patient, his parents and normal human DNA, using probe P5, which show a 0.5 kb insertion in the patient.

It is certified that error appears in the above-identified patent and that said Letters Patent is hereby corrected as shown below:

Column 3, line 22, delete "map of cDNA clones B3A and P5" and insert --mapping of cDNA clones B3A (lane 1) and P5 (lane 2) using EcoRI digest of YAC clone A113D7 genomic DNA--;

line 26, delete "human, mouse and hybrid DNA using the 5' end of the P5 probe, illustrating that NF1LT spans the t(17;22) breakpoint" and insert --EcoRI digests using 5' end of probe P5, wherein M=mouse DNA, H=normal human DNA, 17=DNA from hybrid MH22-6 containing chromosome 17 as only human material, DCR-1=DNA from hybrid containing the der(1) of t(1;17) and NF13=DNA from hybrid containing der(22) of t(17;22)--;

line 29, delete "various human tissue" and insert --human brain, neuroblastoma and kidney tissue--;

line 35, after "B" insert --from the coding region of NF1LT.--;

delete lines 39-41 in their entirety and insert:

--FIG. 5A is a Southern blot of EcoRI digest of new mutation patient (lane 2), his father (lane 1), his mother (lane 3) and an unaffected individual (lane 4).

Figure 5B:
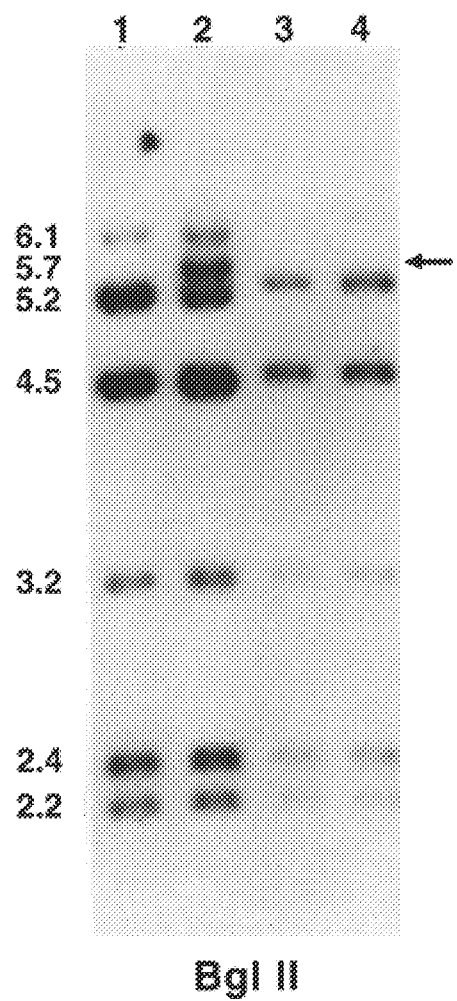

FIG. 5B is a Southern blot of Bgl II digest of new mutation patient (lane 2), his father (lane 1), his mother (lane 3) and an unaffected individual (lane 4).

Figure 5C:
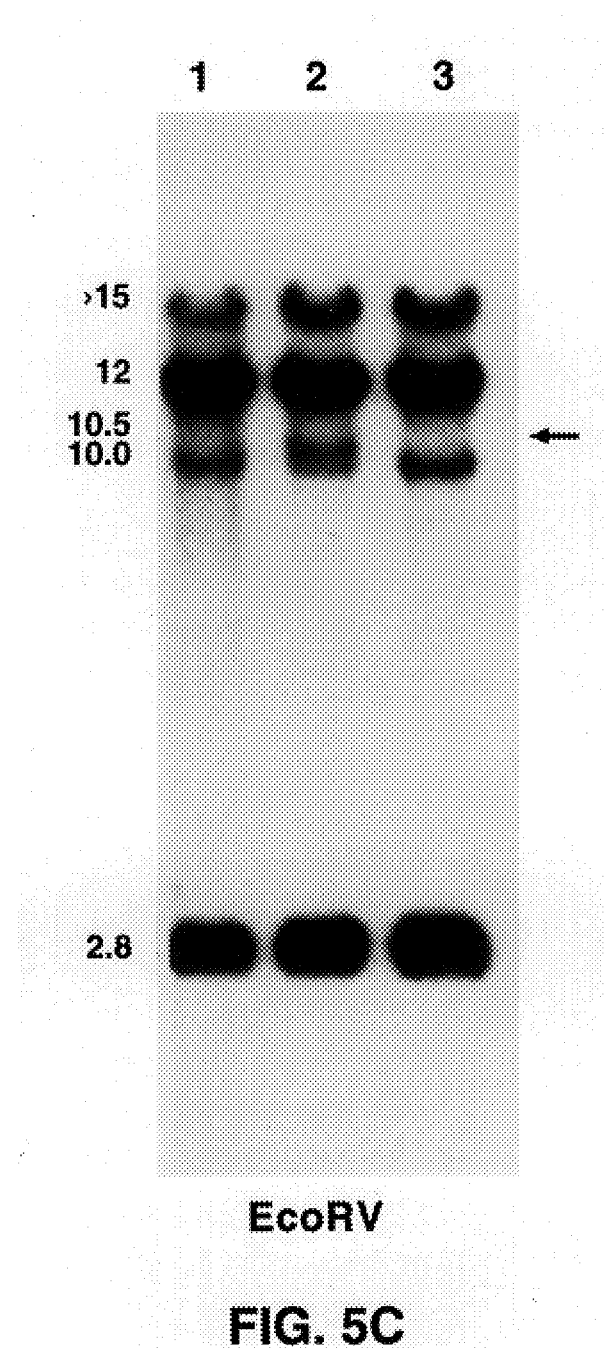

FIG. 5C is a Southern blot of EcoRV digest of new mutation patient (lane 2), his father (lane 1), his mother (lane 3).

Figure 5D:
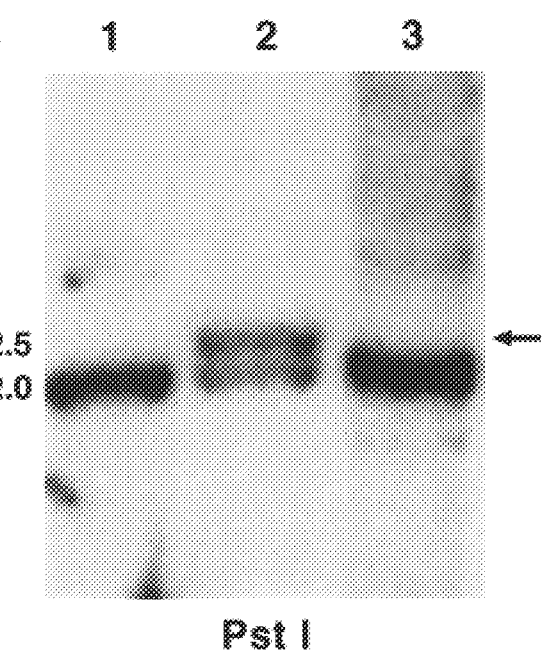

FIG. 5D is a Southern blot of Pst I digest of new mutation patient (lane 2), his father (lane 1), his mother (lane 3). --;

line 42, delete "FIG. 6 (SEQ ID NO:3) and (SEQ ID NO:4) is" and insert --FIGS. 6A and 6B (SEQ ID NO:3 and SEQ ID NO:4) are--;

UNITED STATES PATENT AND TRADEMARK OFFICE
CERTIFICATE OF CORRECTION

PATENT NO : 5,859,195

DATED : January 12, 1999

INVENTOR(S) : Francis S. Collins et al.

It is certified that error appears in the above-identified patent and that said Letters Patent is hereby corrected as shown below:

Column 3, line 44, after "sequence" insert --PCR primers A, B, C and D are indicated; potential N-glycosylation sites are boxed; three possible nuclear localization signals are underlined.--;

line 45, after "NF1LT" insert --(not to scale). Exons are represented by black boxes; connecting lines indicate splicing events; 0.5 kb insertion in new mutation patient lies within the hatched region.--;

line 48, delete "FIG. 9 (SEQ ID NO:5 and SEQ ID NO: 6) is" and insert --FIGS. 9A and 9B (SEQ ID NO:5 and SEQ ID NO:6) are--;

line 48, delete "FIG. 12 (SEQ ID NO:2) is" and insert --FIGS. 12A and 12B (SEQ ID NO:2) are--;

line 65, delete "FIG. 16 are (A)" and insert --FIG. 16A is--;

line 66, delete "and (B)" and insert --FIG. 16B is--.

Signed and Sealed this

Twenty-first Day of December, 1999

*Attest:*

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 8937 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo Sapiens ( v i i i ) POSITION IN GENOME:
        ( A ) CHROMOSOME/SEGMENT: 17q11.2

( i x ) FEATURE:
        ( A ) NAME/KEY: misc_feature
        ( B ) LOCATION: 6814..8937
        ( D ) OTHER INFORMATION: /note= "Entire length of sequence
            clone P5"

( i x ) FEATURE:
        ( A ) NAME/KEY: CDS
        ( B ) LOCATION: 190..8646

( i x ) FEATURE:
        ( A ) NAME/KEY: misc_feature
        ( B ) LOCATION: 8425..8646
        ( D ) OTHER INFORMATION: /note= "219 nt PstI-HindIII
            fragment designated pMAL.B3A"

( i x ) FEATURE:
        ( A ) NAME/KEY: misc_feature
        ( B ) LOCATION: 382..1302
        ( D ) OTHER INFORMATION: /note= "918 nt HpaI-PstI fragment
            designated pMAL.HF3A.P"

( i x ) FEATURE:
        ( A ) NAME/KEY: misc_feature
        ( B ) LOCATION: 382..3909
        ( D ) OTHER INFORMATION: /note= "3523 nt HpaI-XhoI fragment
            designated pMAL.HF3A.X"

( i x ) FEATURE:
        ( A ) NAME/KEY: misc_feature
        ( B ) LOCATION: 8383..8937
        ( D ) OTHER INFORMATION: /note= "Clone B3A"

( x ) PUBLICATION INFORMATION:
        ( A ) AUTHORS: Wallace, M.R. et al.
        ( B ) TITLE: Type 1 Neurofibromatosis Gene: Correction
        ( C ) JOURNAL: Science
        ( D ) VOLUME: 250
        ( E ) ISSUE: 12/21/90
        ( F ) PAGES: 1749-
        ( G ) DATE: 12/21-1990
        ( K ) RELEVANT RESIDUES IN SEQ ID NO:1: FROM 1 TO 8937

( x ) PUBLICATION INFORMATION:
        ( A ) AUTHORS: Wallace, M.R. et al.
        ( B ) TITLE: Type 1 Neurofibromatosis Gene: Identification
            of a Large Transcript in Three NF1 Patients
        ( C ) JOURNAL: Science
        ( D ) VOLUME: 249
        ( E ) ISSUE: 07/13/90
        ( F ) PAGES: 181-186
        ( G ) DATE: 07/13-1990

(K) RELEVANT RESIDUES IN SEQ ID NO:1: FROM 1 TO 8937

(xi) SEQUENCE DESCRIPTION: SEQ ID NO:1:

| | | | | | |
|---|---|---|---|---|---|
| CCCTTTCCCT | CTCCCCTCC | CGCTCGGCGC | TGACCCCCCA | TCCCCACCCC | CGTGGGAACA | 60 |
| CTGGGAGCCT | GCACTCCACA | GACCCTCTCC | TTGCCTCTTC | CCTCACCTCA | GCCTCCGCTC | 120 |
| CCCGCCCTCT | TCCCGGCCCA | GGGCGCCGGC | CCACCCTTCC | CTCCGCCGCC | CCCCGGCCGC | 180 |
| GGGGAGGACA | TGGCCGCGCA | CAGGCCGGTG | GAATGGGTCC | AGGCCGTGGT | CAGCCGCTTC | 240 |
| GACGAGCAGC | TTCCAATAAA | AACAGGACAG | CAGAACACAC | ATACCAAAGT | CAGTACTGAG | 300 |
| CACAACAAGG | AATGTCTAAT | CAATATTTCC | AAATACAAGT | TTTCTTTGGT | TATAAGCGGC | 360 |
| CTCACTACTA | TTTTAAAGAA | TGTTAACAAT | ATGAGAATAT | TTGGAGAAGC | TGCTGAAAAA | 420 |
| AATTTATATC | TCTCTCAGTT | GATTATATTG | GATACACTGG | AAAAATGTCT | TGCTGGGCAA | 480 |
| CCAAAGGACA | CAATGAGATT | AGATGAAACG | ATGCTGGTCA | AACAGTTGCT | GCCAGAAATC | 540 |
| TGCCATTTTC | TTCACACCTG | TCGTGAAGGA | AACCAGCATG | CAGCTGAACT | TCGGAATTCT | 600 |
| GCCTCTGGGG | TTTTATTTTC | TCTCAGCTGC | AACAACTTCA | ATGCAGTCTT | TAGTCGCATT | 660 |
| TCTACCAGGT | TACAGGAATT | AACTGTTTGT | TCAGAAGACA | ATGTTGATGT | TCATGATATA | 720 |
| GAATTGTTAC | AGTATATCAA | TGTGGATTGT | GCAAAATTAA | AACGACTCCT | GAAGGAAACA | 780 |
| GCATTTAAAT | TTAAAGCCCT | AAAGAAGGTT | GCGCAGTTAG | CAGTTATAAA | TAGCCTGGAA | 840 |
| AAGGCATTTT | GGAACTGGGT | AGAAAATTAT | CCAGATGAAT | TTACAAAACT | GTACCAGATC | 900 |
| CCACAGACTG | ATATGGCTGA | ATGTGCAGAA | AAGCTATTTG | ACTTGGTGGA | TGGTTTTGCT | 960 |
| GAAAGCACCA | AACGTAAAGC | AGCAGTTTGG | CCACTACAAA | TCATTCTCCT | TATCTTGTGT | 1020 |
| CCAGAAATAA | TCCAGGATAT | ATCCAAAGAC | GTGGTTGATG | AAAACAACAT | GAATAAGAAG | 1080 |
| TTATTTCTGG | ACAGTCTACG | AAAAGCTCTT | GCTGGCCATG | GAGGAAGTAG | GCAGCTGACA | 1140 |
| GAAAGTGCTG | CAATTGCCTG | TGTCAAACTG | TGTAAAGCAA | GTACTTACAT | CAATTGGGAA | 1200 |
| GATAACTCTG | TCATTTTCCT | ACTTGTTCAG | TCCATGGTGG | TTGATCTTAA | GAACCTGCTT | 1260 |
| TTTAATCCAA | GTAAGCCATT | CTCAAGAGGC | AGTCAGCCTG | CAGATGTGGA | TCTAATGATT | 1320 |
| GACTGCCTTG | TTTCTTGCTT | TCGTATAAGC | CCTCACAACA | ACCAACACTT | TAAGATCTGC | 1380 |
| CTGGCTCAGA | ATTCACCTTC | TACATTTCAC | TATGTGCTGG | TAAATTCACT | CCATCGAATC | 1440 |
| ATCACCAATT | CCGCATTGGA | TTGGTGGCCT | AAGATTGATG | CTGTGTATTG | TCACTCGGTT | 1500 |
| GAACTTCGAA | ATATGTTTGG | TGAAACACTT | CATAAAGCAG | TGCAAGGTTG | TGGAGCACAC | 1560 |
| CCAGCAATAC | GAATGGCCCC | GAGTCTTACA | TTTAAAGAAA | AAGTAACAAG | CCTTAAATTT | 1620 |
| AAAGAAAAAC | CTACAGACCT | GGAGACAAGA | AGCTATAAGT | ATCTTCTCTT | GTCCATAGTG | 1680 |
| AAACTAATTC | ATGCAGATCC | AAAGCTCTTG | CTTTGTAATC | CAAGAAAACA | GGGGCCCGAA | 1740 |
| ACCCAAGGCA | GTACAGCAGA | ATTAATTACA | GGGCTCGTCC | AACTGGTCCC | TCAGTCACAC | 1800 |
| ATGCCAGAGA | TTGCTCAGGA | AGCAATGGAG | GCTCTGCTGG | TTCTTCATCA | GTTAGATAGC | 1860 |
| ATTGATTTGT | GGAATCCTGA | TGCTCCTGTA | GAAACATTTT | GGGAGATTAG | CTCACAAATG | 1920 |
| CTTTTTTACA | TCTGCAAGAA | ATTAACTAGT | CATCAAATGC | TTAGTAGCAC | AGAAATTCTC | 1980 |
| AAGTGGTTGC | GGGAAATATT | GATCTGCAGG | AATAAATTTC | TTCTTAAAAA | TAAGCAGGCA | 2040 |
| GATAGAAGTT | CCTGTCACTT | TCTCCTTTTT | TACGGGGTAG | GATGTGATAT | TCCTTCTAGT | 2100 |
| GGAAATACCA | GTCAAATGTC | CATGGATCAT | GAAGAATTAC | TACGTACTCC | TGGAGCCTCT | 2160 |
| CTCCGGAAGG | GAAAAGGGAA | CTCCTCTATG | GATAGTGCAG | CAGGATGCAG | CGGAACCCCC | 2220 |
| CCAATTTGCC | GACAAGCCCA | GACCAAACTA | GAAGTGGCCC | TGTACATGTT | TCTGTGGAAC | 2280 |

| | | | | | |
|---|---|---|---|---|---|
| CCTGACACTG | AAGCTGTTCT | GGTTGCCATG | TCCTGTTTCC | GCCACCTCTG | TGAGGAAGCA | 2340 |
| GATATCCGGT | GTGCGGTGGA | TGAAGTGTCA | GTGCATAACC | TCTTGCCCAA | CTATAACACA | 2400 |
| TTCATGGAGT | TTGCCTCTGT | CAGCAATATG | ATGTCAACAG | GAAGAGCAGC | ACTTCAGAAA | 2460 |
| AGAGTGATGG | CACTGCTGAG | GCGCATTGAG | CATCCCACTG | CAGGAAACAC | TGAGGCTTGG | 2520 |
| GAAGATACAC | ATGCAAAATG | GGAACAAGCA | ACAAAGCTAA | TCCTTAACTA | TCCAAAAGCC | 2580 |
| AAAATGGAAG | ATGGCCAGGC | TGCTGAAAGC | CTTCACAAGA | CCATTGTTAA | GAGGCGAATG | 2640 |
| TCCCATGTGA | GTGGAGGAGG | ATCCATAGAT | TTGTCTGACA | CAGACTCCCT | ACAGGAATGG | 2700 |
| ATCAACATGA | CTGGCTTCCT | TTGTGCCCTT | GGAGGAGTGT | GCCTCCAGCA | GAGAAGCAAT | 2760 |
| TCTGGCCTGG | CAACCTATAG | CCCACCCATG | GGTCCAGTCA | GTGAACGTAA | GGGTTCTATG | 2820 |
| ATTTCAGTGA | TGTCTTCAGA | GGGAAACGCA | GATACACCTG | TCAGCAAATT | TATGGATCGG | 2880 |
| CTGTTGTCCT | TAATGGTGTG | TAACCATGAG | AAAGTGGGAC | TTCAAATACG | GACCAATGTT | 2940 |
| AAGGATCTGG | TGGGTCTAGA | ATTGAGTCCT | GCTCTGTATC | CAATGCTATT | TAACAAATTG | 3000 |
| AAGAATACCA | TCAGCAAGTT | TTTTGACTCC | CAAGGACAGG | TTTTATTGAC | TGATACCAAT | 3060 |
| ACTCAATTTG | TAGAACAAAC | CATAGCTATA | ATGAATAACT | GCTAGATAA | TCATACTGAA | 3120 |
| GGCAGCTCTG | AACATCTAGG | GCAAGCTAGC | ATTGAAACAA | TGATGTTAAA | TCTGGTCAGG | 3180 |
| TATGTTCGTG | TGCTTGGGAA | TATGGTCCAT | GCAATTCAAA | TAAAACGAA | ACTGTGTCAA | 3240 |
| TTAGTTGAAG | TAATGATGGC | AAGGAGAGAT | GACCTCTCAT | TTTGCCAAGA | GATGAAATTT | 3300 |
| AGGAATAAGA | TGGTAGAATA | CCTGACAGAC | TGGGTTATGG | GAACATCAAA | CCAAGCAGCA | 3360 |
| GATGATGATG | TAAAATGTCT | TACAAGAGAT | TTGGACCAGG | CAAGCATGGA | AGCAGTAGTT | 3420 |
| TCACTTCTAG | CTGGTCTCCC | TCTGCAGCCT | GAAGAAGGAG | ATGGTGTGGA | ATTGATGGAA | 3480 |
| GCCAAATCAC | AGTTATTTCT | TAAATACTTC | ACATTATTTA | TGAACCTTTT | GAATGACTGC | 3540 |
| AGTGAAGTTG | AAGATGAAAG | TGCGCAAACA | GGTGGCAGGA | AACGTGGCAT | GTCTCGGAGG | 3600 |
| CTGGCATCAC | TGAGGCACTG | TACGGTCCTT | GCAATGTCAA | ACTTACTCAA | TGCCAACGTA | 3660 |
| GACAGTGGTC | TCATGCACTC | CATAGGCTTA | GGTTACCACA | AGGATCTCCA | GACAAGAGCT | 3720 |
| ACATTTATGG | AAGTTCTGAC | AAAAATCCTT | CAACAAGGCA | CAGAATTTGA | CACACTTGCA | 3780 |
| GAAACAGTAT | TGGCTGATCG | GTTTGAGAGA | TTGGTGGAAC | TGGTCACAAT | GATGGGTGAT | 3840 |
| CAAGGAGAAC | TCCCTATAGC | GATGGCTCTG | GCCAATGTGG | TTCCTTGTTC | TCAGTGGGAT | 3900 |
| GAACTAGCTC | GAGTTCTGGT | TACTCTGTTT | GATTCTCGGC | ATTACTCTA | CCAACTGCTC | 3960 |
| TGGAACATGT | TTTCTAAAGA | AGTAGAATTG | GCAGACTCCA | TGCAGACTCT | CTTCCGAGGC | 4020 |
| AACAGCTTGG | CCAGTAAAAT | AATGACATTC | TGTTTCAAGG | TATATGGTGC | TACCTATCTA | 4080 |
| CAAAAACTCC | TGGATCCTTT | ATTACGAATT | GTGATCACAT | CCTCTGATTG | GCAACATGTT | 4140 |
| AGCTTTGAAG | TGGATCCTAC | CAGGTTAGAA | CCATCAGAGA | GCCTTGAGGA | AAACCAGCGG | 4200 |
| AACCTCCTTC | AGATGACTGA | AAAGTTCTTC | CATGCCATCA | TCAGTTCCTC | CTCAGAATTC | 4260 |
| CCCCCTCAAC | TTCGAAGTGT | GTGCCACTGT | TTATACCAGG | TGGTTAGCCA | GCGTTTCCCT | 4320 |
| CAGAACAGCA | TCGGTGCAGT | AGGAAGTGCC | ATGTTCCTCA | GATTTATCAA | TCCTGCCATT | 4380 |
| GTCTCACCGT | ATGAAGCAGG | GATTTAGAT | AAAAGCCAC | CACCTAGAAT | CGAAAGGGGC | 4440 |
| TTGAAGTTAA | TGTCAAAGAT | ACTTCAGAGT | ATTGCCAATC | ATGTTCTCTT | CACAAAAGAA | 4500 |
| GAACATATGC | GGCCTTTCAA | TGATTTTGTG | AAAAGCAACT | TGATGCAGC | ACGCAGGTTT | 4560 |
| TTCCTTGATA | TAGCATCTGA | TTGTCCTACA | AGTGATGCAG | TAAATCATAG | TCTTTCCTTC | 4620 |
| ATAAGTGACG | GCAATGTGCT | TGCTTTACAT | CGTCTACTCT | GGAACAATCA | GGAGAAAATT | 4680 |

| | | | | | | |
|---|---|---|---|---|---|---|
| GGGCAGTATC | TTTCCAGCAA | CAGGGATCAT | AAAGCTGTTG | GAAGACGACC | TTTTGATAAG | 4740 |
| ATGGCAACAC | TTCTTGCATA | CCTGGGTCCT | CCAGAGCACA | AACCTGTGGC | AGATACACAC | 4800 |
| TGGTCCAGCC | TTAACCTTAC | CAGTTCAAAG | TTTGAGGAAT | TTATGACTAG | GCATCAGGTA | 4860 |
| CATGAAAAAG | AAGAATTCAA | GGCTTTGAAA | ACGTTAAGTA | TTTTCTACCA | AGCTGGGACT | 4920 |
| TCCAAAGCTG | GGAATCCTAT | TTTTTATTAT | GTTGCACGGA | GGTTCAAAAC | TGGTCAAATC | 4980 |
| AATGGTGATT | TGCTGATATA | CCATGTCTTA | CTGACTTTAA | AGCCATATTA | TGCAAAGCCA | 5040 |
| TATGAAATTG | TAGTGGACCT | TACCCATACC | GGGCCTAGCA | ATCGCTTTAA | AACAGACTTT | 5100 |
| CTCTCTAAGT | GGTTTGTTGT | TTTTCCTGGC | TTTGCTTACG | ACAACGTCTC | CGCAGTCTAT | 5160 |
| ATCTATAACT | GTAACTCCTG | GGTCAGGGAG | TACACCAAGT | ATCATGAGCG | CTGCTGACT | 5220 |
| GGCCTCAAAG | GTAGCAAAAG | GCTTGTTTTC | ATAGACTGTC | CTGGGAAACT | GGCTGAGCAC | 5280 |
| ATAGAGCATG | AACAACAGAA | ACTACCTGCT | GCCACCTTGG | CTTTAGAAGA | GGACCTGAAG | 5340 |
| GTATTCCACA | ATGCTCTCAA | GCTAGCTCAC | AAAGACACCA | AAGTTTCTAT | TAAAGTTGGT | 5400 |
| TCTACTGCTG | TCCAAGTAAC | TTCAGCAGAG | CGAACAAAAG | TCCTAGGGCA | ATCAGTCTTT | 5460 |
| CTAAATGACA | TTTATTATGC | TTCGGAAATT | GAAGAAATCT | GCCTAGTAGA | TGAGAACCAG | 5520 |
| TTCACCTTAA | CCATTGCAAA | CCAGGGCACG | CCGCTCACCT | TCATGCACCA | GGAGTGTGAA | 5580 |
| GCCATTGTCC | AGTCTATCAT | TCATATCCGG | ACCCGCTGGG | AACTGTCACA | GCCCGACTCT | 5640 |
| ATCCCCCAAC | ACACCAAGAT | TCGGCCAAAA | GATGTCCCTG | GACACTGCT | CAATATCGCA | 5700 |
| TTACTTAATT | TAGGCAGTTC | TGACCCGAGT | TTACGGTCAG | CTGCCTATAA | TCTTCTGTGT | 5760 |
| GCCTTAACTT | GTACCTTTAA | TTTAAAAATC | GAGGGCCAGT | TACTAGAGAC | ATCAGGTTTA | 5820 |
| TGTATCCCTG | CCAACAACAC | CCTCTTTATT | GTCTCTATTA | GTAAGCACT | GGCAGCCAAT | 5880 |
| GAGCCACACC | TCACGTTAGA | ATTTTTGGAA | GAGTGTATTT | CTGGATTTAG | CAAATCTAGT | 5940 |
| ATTGAATTGA | AACACCTTTG | TTTGGAATAC | ATGACTCCAT | GGCTGTCAAA | TCTAGTTCGT | 6000 |
| TTTTGCAAGC | ATAATGATGA | TGCCAAACGA | CAAAGAGTTA | CTGCTATTCT | TGACAAGCTG | 6060 |
| ATAACAATGA | CCATCAATGA | AAAACAGATG | TACCCATCTA | TTCAAGCAAA | AATATGGGGA | 6120 |
| AGCCTTGGGC | AGATTACAGA | TCTGCTTGAT | GTTGTACTAG | ACAGTTTCAT | CAAAACCAGT | 6180 |
| GCAACAGGTG | GCTTGGGATC | AATAAAAGCT | GAGGTGATGG | CAGATACTGC | TGTAGCTTTG | 6240 |
| GCTTCTGGAA | ATGTGAAATT | GGTTTCAAGC | AAGGTTATTG | GAAGGATGTG | CAAAATAATT | 6300 |
| GACAAGACAT | GCTTATCTCC | AACTCCTACT | TTAGAACAAC | ATCTTATGTG | GGATGATATT | 6360 |
| GCTATTTTAG | CACGCTACAT | GCTGATGCTG | TCCTTCAACA | ATTCCCTTGA | TGTGGCAGCT | 6420 |
| CATCTTCCCT | ACCTCTTCCA | CGTTGTTACT | TTCTTAGTAG | CCACAGGTCC | GCTCTCCCTT | 6480 |
| AGAGCTTCCA | CACATGGACT | GGTCATTAAT | ATCATTCACT | CTCTGTGTAC | TTGTTCACAG | 6540 |
| CTTCATTTTA | GTGAAGAGAC | CAAGCAAGTT | TTGAGACTCA | GTCTGACAGA | GTTCTCATTA | 6600 |
| CCCAAATTTT | ACTTGCTGTT | TGGCATTAGC | AAAGTCAAGT | CAGCTGCTGT | CATTGCCTTC | 6660 |
| CGTTCCAGTT | ACCGGGACAG | GTCATTCTCT | CCTGGCTCCT | ATGAGAGAGA | GACTTTTGCT | 6720 |
| TTGACATCCT | TGGAAACAGT | CACAGAAGCT | TTGTTGGAGA | TCATGGAGGC | ATGCATGAGA | 6780 |
| GATATTCCAA | CGTGCAAGTG | GCTGGACCAG | TGGACAGAAC | TAGCTCAAAG | ATTTGCATTC | 6840 |
| CAATATAATC | CATCCCTGCA | ACCAAGAGCT | CTTGTTGTCT | TTGGGTGTAT | TAGCAAACGA | 6900 |
| GTGTCTCATG | GGCAGATAAA | GCAGATAATC | CGTATTCTTA | GCAAGGCACT | TGAGAGTTGC | 6960 |
| TTAAAAGGAC | CTGACACTTA | CAACAGTCAA | GTTCTGATAG | AAGCTACAGT | AATAGCACTA | 7020 |
| ACCAAATTAC | AGCCACTTCT | TAATAAGGAC | TCGCCTCTGC | ACAAAGCCCT | CTTTTGGGTA | 7080 |

| | | | | | | |
|---|---|---|---|---|---|---|
| GCTGTGGCTG | TGCTGCAGCT | TGATGAGGTC | AACTTGTATT | CAGCAGGTAC | CGCACTTCTT | 7140 |
| GAACAAAACC | TGCATACTTT | AGATAGTCTC | CGTATATTCA | ATGACAAGAG | TCCAGAGGAA | 7200 |
| GTATTTATGG | CAATCCGGAA | TCCTCTGGAG | TGGCACTGCA | AGCAAATGGA | TCATTTTGTT | 7260 |
| GGACTCAATT | TCAACTCTAA | CTTTAACTTT | GCATTGGTTG | GACACCTTTT | AAAAGGGTAC | 7320 |
| AGGCATCCTT | CACCTGCTAT | TGTTGCAAGA | ACAGTCAGAA | TTTTACATAC | ACTACTAACT | 7380 |
| CTGGTTAACA | AACACAGAAA | TTGTGACAAA | TTTGAAGTGA | ATACACAGAG | CGTGGCCTAC | 7440 |
| TTAGCAGCTT | TACTTACAGT | GTCTGAAGAA | GTTCGAAGTC | GCTGCAGCCT | AAAACATAGA | 7500 |
| AAGTCACTTC | TTCTTACTGA | TATTTCAATG | GAAAATGTTC | CTATGGATAC | ATATCCCATT | 7560 |
| CATCATGGTG | ACCCTTCCTA | TAGGACACTA | AAGGAGACTC | AGCCATGGTC | CTCTCCCAAA | 7620 |
| GGTTCTGAAG | GATACCTTGC | AGCCACCTAT | CCAACTGTCG | GCCAGACCAG | TCCCCGAGCC | 7680 |
| AGGAAATCCA | TGAGCCTGGA | CATGGGGCAA | CCTTCTCAGG | CCAACACTAA | GAAGTTGCTT | 7740 |
| GGAACAAGGA | AAAGTTTTGA | TCACTTGATA | TCAGACACAA | AGGCTCCTAA | AAGGCAAGAA | 7800 |
| ATGGAATCAG | GGATCACAAC | ACCCCCCAAA | ATGAGGAGAG | TAGCAGAAAC | TGATTATGAA | 7860 |
| ATGGAAACTC | AGAGGATTTC | CTCATCACAA | CAGCACCCAC | ATTACGTAA | AGTTCAGTG | 7920 |
| TCTGAATCAA | ATGTTCTCTT | GGATGAAGAA | GTACTTACTG | ATCCGAAGAT | CCAGGCGCTG | 7980 |
| CTTCTTACTG | TTCTAGCTAC | ACTGGTAAAA | TATACCACAG | ATGAGTTTGA | TCAACGAATT | 8040 |
| CTTTATGAAT | ACTTAGCAGA | GGCCAGTGTT | GTGTTTCCCA | AAGTCTTTCC | TGTTGTGCAT | 8100 |
| AATTTGTTGG | ACTCTAAGAT | CAACACCCTG | TTATCATTGT | GCCAAGATCC | AAATTTGTTA | 8160 |
| AATCCAATCC | ATGGAATTGT | GCAGAGTGTG | GTGTACCATG | AAGAATCCCC | ACCACAATAC | 8220 |
| CAAACATCTT | ACCTGCAAAG | TTTTGGTTTT | AATGGCTTGT | GGCGGTTTGC | AGGACCGTTT | 8280 |
| TCAAAGCAAA | CACAAATTCC | AGACTATGCT | GAGCTTATTG | TTAAGTTTCT | TGATGCCTTG | 8340 |
| ATTGACACGT | ACCTGCCTGG | AATTGATGAA | GAAACCAGTG | AAGAATCCCT | CCTGACTCCC | 8400 |
| ACATCTCCTT | ACCCTCCTGC | ACTGCAGAGC | CAGCTTAGTA | TCACTGCCAA | CCTTAACCTT | 8460 |
| TCTAATTCCA | TGACCTCACT | TGCAACTTCC | CAGCATTCCC | CAGGAATCGA | CAAGGAGAAC | 8520 |
| GTTGAACTCT | CCCCTACCAC | TGGCCACTGT | AACAGTGGAC | GAACTCGCCA | CGGATCCGCA | 8580 |
| AGCCAAGTGC | AGAAGCAAAG | AAGCGCTGGC | AGTTTCAAAC | GTAATAGCAT | TAAGAAGATC | 8640 |
| GTGTGAAGCT | TGCTTGCTTT | CTTTTTTAAA | ATCAACTTAA | CATGGGCTCT | TCACTAGTGA | 8700 |
| CCCCTTCCCT | GTCCTTGCCC | TTTCCCCCCA | TGTTGTAATG | CTGCACTTCC | TGTTTTATAA | 8760 |
| TGAACCCATC | CGGTTTGCCA | TGTTGCCAGA | TGATCAACTC | TTCGAAGCCT | TGCCTAAATT | 8820 |
| TAATGCTGCC | TTTTCTTTAA | CTTTTTTTCT | TCTACTTTTG | GCGTGTATCT | GGTATATGTA | 8880 |
| AGTGTTCAGA | ACAACTGCAA | AGAAAGTGGG | AGGTCAGGAA | ACTTTTAACT | GAGAAAT | 8937 |

( 2 ) INFORMATION FOR SEQ ID NO:2:

( i ) SEQUENCE CHARACTERISTICS:
        ( A ) LENGTH: 2818 amino acids
        ( B ) TYPE: amino acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens ( v i i i ) POSITION IN GENOME:
    ( A ) CHROMOSOME/SEGMENT: 17q11.2

( i x ) FEATURE:
    ( A ) NAME/KEY: Cleavage-site
    ( B ) LOCATION: group(583..586, 815..818, 2573..2576,
        2810..2813)
    ( D ) OTHER INFORMATION: /note= "Potential cAMP-dependent
        protein kinase recognition sites"

( i x ) FEATURE:
    ( A ) NAME/KEY: Modified-site
    ( B ) LOCATION: 2549..2556
    ( D ) OTHER INFORMATION: /note= "Potential tyrosine
        phosphorylation site"

( i x ) FEATURE:
    ( A ) NAME/KEY: Modified-site
    ( B ) LOCATION: group(1264, 1276, 1358, 1377, 1389, 1390, 1391,
        1395, 1396, 1400, 1423, 1426, 1429, 1430)
    ( D ) OTHER INFORMATION: /note= "Invariant residues within
        most statistically significant regions of similarity
        among the GAP family of proteins"

( i x ) FEATURE:
    ( A ) NAME/KEY: Modified-site
    ( B ) LOCATION: group(1264..1290, 1345..1407, 1415..1430)
    ( D ) OTHER INFORMATION: /note= "Most statistically
        significant regions of similarity among the GAP family
        of proteins"

( i x ) FEATURE:
    ( A ) NAME/KEY: Modified-site
    ( B ) LOCATION: 496
    ( D ) OTHER INFORMATION: /note= "At variance with previously
        published sequence which shows an ATG methionine codon
        rather than an ATA isoleucine codon"

( i x ) FEATURE:
    ( A ) NAME/KEY: Modified-site
    ( B ) LOCATION: 1183
    ( D ) OTHER INFORMATION: /note= "At variance with previously
        published sequence. Shows an CTG leucine codon rather
        than the previously published CTC"

( i x ) FEATURE:
    ( A ) NAME/KEY: Modified-site
    ( B ) LOCATION: 1555
    ( D ) OTHER INFORMATION: /note= "At variance with previously
        published sequence. Lacks an extra CAT histidine condon
        after this residue"

( i x ) FEATURE:
    ( A ) NAME/KEY: Modified-site
    ( B ) LOCATION: (2771 2772)
    ( D ) OTHER INFORMATION: /note= "Position of an 18 amino
        acid insertion(SEQ ID NO:10) representing an
        alternatively spliced product"

( i x ) FEATURE:
    ( A ) NAME/KEY: Modified-site
    ( B ) LOCATION: (1370 1371)
    ( D ) OTHER INFORMATION: /note= "Position of a 21 amino acid
        insertion representing an alternatively spliced product"

( i x ) FEATURE:
    ( A ) NAME/KEY: Domain
    ( B ) LOCATION: 1125..1537
    ( D ) OTHER INFORMATION: /note= "NF1 catalytic domain"

( i x ) FEATURE:
    ( A ) NAME/KEY: Modified-site
    ( B ) LOCATION: 2746..2818
    ( D ) OTHER INFORMATION: /note= "Corresponding amino acids
        for the PstI- HindIII fragment designated pMAL.B3A"

( i x ) FEATURE:
    ( A ) NAME/KEY: Modified-site
    ( B ) LOCATION: 65..371
    ( D ) OTHER INFORMATION: /note= "Corresponding amino acids for the HpaI- PstI fragment designated pMAL.HF3A.P"

(ix) FEATURE:
    (A) NAME/KEY: Modified-site
    (B) LOCATION: 65..1240
    (D) OTHER INFORMATION: /note= "Corresponding amino acids
        for the HpaI- XhoI fragment designated pMAL.HF3A.X"

(x) PUBLICATION INFORMATION:
    (A) AUTHORS: Wallace, M.R. et al.
    (B) TITLE: Type 1 Neurofibromatosis Gene: Correction
    (C) JOURNAL: Science
    (D) VOLUME: 250
    (E) ISSUE: 12/21/90
    (F) PAGES: 1749-
    (G) DATE: 12/21-1990
    (K) RELEVANT RESIDUES IN SEQ ID NO:2: FROM 1 TO 2818

(x) PUBLICATION INFORMATION:
    (A) AUTHORS: Wallace, M.R. et al.
    (B) TITLE: Type 1 Neurofibromatosis Gene: Identification
        of a Large Transcript in Three NF1 Patients
    (C) JOURNAL: Science
    (D) VOLUME: 249
    (E) ISSUE: 07/13/90
    (F) PAGES: 181-186
    (G) DATE: 07/13-1990
    (K) RELEVANT RESIDUES IN SEQ ID NO:2: FROM 1 TO 2818

(xi) SEQUENCE DESCRIPTION: SEQ ID NO:2:

```
Met Ala Ala His Arg Pro Val Glu Trp Val Gln Ala Val Val Ser Arg
 1               5                  10                  15

Phe Asp Glu Gln Leu Pro Ile Lys Thr Gly Gln Gln Asn Thr His Thr
            20                  25                  30

Lys Val Ser Thr Glu His Asn Lys Glu Cys Leu Ile Asn Ile Ser Lys
        35                  40                  45

Tyr Lys Phe Ser Leu Val Ile Ser Gly Leu Thr Thr Ile Leu Lys Asn
    50                  55                  60

Val Asn Asn Met Arg Ile Phe Gly Glu Ala Ala Glu Lys Asn Leu Tyr
65                  70                  75                  80

Leu Ser Gln Leu Ile Ile Leu Asp Thr Leu Glu Lys Cys Leu Ala Gly
                85                  90                  95

Gln Pro Lys Asp Thr Met Arg Leu Asp Glu Thr Met Leu Val Lys Gln
            100                 105                 110

Leu Leu Pro Glu Ile Cys His Phe Leu His Thr Cys Arg Glu Gly Asn
            115                 120                 125

Gln His Ala Ala Glu Leu Arg Asn Ser Ala Ser Gly Val Leu Phe Ser
    130                 135                 140

Leu Ser Cys Asn Asn Phe Asn Ala Val Phe Ser Arg Ile Ser Thr Arg
145                 150                 155                 160

Leu Gln Glu Leu Thr Val Cys Ser Glu Asp Asn Val Asp Val His Asp
                165                 170                 175

Ile Glu Leu Leu Gln Tyr Ile Asn Val Asp Cys Ala Lys Leu Lys Arg
            180                 185                 190

Leu Leu Lys Glu Thr Ala Phe Lys Phe Lys Ala Leu Lys Lys Val Ala
        195                 200                 205

Gln Leu Ala Val Ile Asn Ser Leu Glu Lys Ala Phe Trp Asn Trp Val
    210                 215                 220

Glu Asn Tyr Pro Asp Glu Phe Thr Lys Leu Tyr Gln Ile Pro Gln Thr
225                 230                 235                 240

Asp Met Ala Glu Cys Ala Glu Lys Leu Phe Asp Leu Val Asp Gly Phe
                245                 250                 255

Ala Glu Ser Thr Lys Arg Lys Ala Ala Val Trp Pro Leu Gln Ile Ile
```

|     |     |     |     |     | 260 |     |     |     |     | 265 |     |     |     |     | 270 |     |
| --- | --- | --- | --- | --- | --- | --- | --- | --- | --- | --- | --- | --- | --- | --- | --- | --- |
| Leu | Leu | Ile | Leu | Cys | Pro | Glu | Ile | Ile | Gln | Asp | Ile | Ser | Lys | Asp | Val |
|     |     |     | 275 |     |     |     | 280 |     |     |     |     | 285 |     |     |     |
| Val | Asp | Glu | Asn | Asn | Met | Asn | Lys | Lys | Leu | Phe | Leu | Asp | Ser | Leu | Arg |
|     |     | 290 |     |     |     | 295 |     |     |     |     | 300 |     |     |     |     |
| Lys | Ala | Leu | Ala | Gly | His | Gly | Gly | Ser | Arg | Gln | Leu | Thr | Glu | Ser | Ala |
| 305 |     |     |     |     | 310 |     |     |     |     | 315 |     |     |     |     | 320 |
| Ala | Ile | Ala | Cys | Val | Lys | Leu | Cys | Lys | Ala | Ser | Thr | Tyr | Ile | Asn | Trp |
|     |     |     |     | 325 |     |     |     |     | 330 |     |     |     |     | 335 |     |
| Glu | Asp | Asn | Ser | Val | Ile | Phe | Leu | Leu | Val | Gln | Ser | Met | Val | Val | Asp |
|     |     |     |     | 340 |     |     |     | 345 |     |     |     |     | 350 |     |     |
| Leu | Lys | Asn | Leu | Leu | Phe | Asn | Pro | Ser | Lys | Pro | Phe | Ser | Arg | Gly | Ser |
|     |     | 355 |     |     |     |     | 360 |     |     |     |     | 365 |     |     |     |
| Gln | Pro | Ala | Asp | Val | Asp | Leu | Met | Ile | Asp | Cys | Leu | Val | Ser | Cys | Phe |
|     | 370 |     |     |     |     | 375 |     |     |     |     | 380 |     |     |     |     |
| Arg | Ile | Ser | Pro | His | Asn | Asn | Gln | His | Phe | Lys | Ile | Cys | Leu | Ala | Gln |
| 385 |     |     |     |     | 390 |     |     |     |     | 395 |     |     |     |     | 400 |
| Asn | Ser | Pro | Ser | Thr | Phe | His | Tyr | Val | Leu | Val | Asn | Ser | Leu | His | Arg |
|     |     |     |     | 405 |     |     |     |     | 410 |     |     |     |     | 415 |     |
| Ile | Ile | Thr | Asn | Ser | Ala | Leu | Asp | Trp | Trp | Pro | Lys | Ile | Asp | Ala | Val |
|     |     |     | 420 |     |     |     |     | 425 |     |     |     |     | 430 |     |     |
| Tyr | Cys | His | Ser | Val | Glu | Leu | Arg | Asn | Met | Phe | Gly | Glu | Thr | Leu | His |
|     |     |     | 435 |     |     |     |     | 440 |     |     |     |     | 445 |     |     |
| Lys | Ala | Val | Gln | Gly | Cys | Gly | Ala | His | Pro | Ala | Ile | Arg | Met | Ala | Pro |
|     | 450 |     |     |     |     | 455 |     |     |     |     | 460 |     |     |     |     |
| Ser | Leu | Thr | Phe | Lys | Glu | Lys | Val | Thr | Ser | Leu | Lys | Phe | Lys | Glu | Lys |
| 465 |     |     |     |     | 470 |     |     |     |     | 475 |     |     |     |     | 480 |
| Pro | Thr | Asp | Leu | Glu | Thr | Arg | Ser | Tyr | Lys | Tyr | Leu | Leu | Leu | Ser | Ile |
|     |     |     |     | 485 |     |     |     |     | 490 |     |     |     |     | 495 |     |
| Val | Lys | Leu | Ile | His | Ala | Asp | Pro | Lys | Leu | Leu | Leu | Cys | Asn | Pro | Arg |
|     |     |     |     | 500 |     |     |     | 505 |     |     |     |     | 510 |     |     |
| Lys | Gln | Gly | Pro | Glu | Thr | Gln | Gly | Ser | Thr | Ala | Glu | Leu | Ile | Thr | Gly |
|     |     | 515 |     |     |     |     | 520 |     |     |     |     | 525 |     |     |     |
| Leu | Val | Gln | Leu | Val | Pro | Gln | Ser | His | Met | Pro | Glu | Ile | Ala | Gln | Glu |
|     | 530 |     |     |     |     | 535 |     |     |     |     | 540 |     |     |     |     |
| Ala | Met | Glu | Ala | Leu | Leu | Val | Leu | His | Gln | Leu | Asp | Ser | Ile | Asp | Leu |
| 545 |     |     |     |     | 550 |     |     |     |     | 555 |     |     |     |     | 560 |
| Trp | Asn | Pro | Asp | Ala | Pro | Val | Glu | Thr | Phe | Trp | Glu | Ile | Ser | Ser | Gln |
|     |     |     |     | 565 |     |     |     |     | 570 |     |     |     |     | 575 |     |
| Met | Leu | Phe | Tyr | Ile | Cys | Lys | Lys | Leu | Thr | Ser | His | Gln | Met | Leu | Ser |
|     |     |     | 580 |     |     |     |     | 585 |     |     |     |     | 590 |     |     |
| Ser | Thr | Glu | Ile | Leu | Lys | Trp | Leu | Arg | Glu | Ile | Leu | Ile | Cys | Arg | Asn |
|     |     | 595 |     |     |     |     | 600 |     |     |     |     | 605 |     |     |     |
| Lys | Phe | Leu | Leu | Lys | Asn | Lys | Gln | Ala | Asp | Arg | Ser | Ser | Cys | His | Phe |
|     | 610 |     |     |     |     | 615 |     |     |     |     | 620 |     |     |     |     |
| Leu | Leu | Phe | Tyr | Gly | Val | Gly | Cys | Asp | Ile | Pro | Ser | Ser | Gly | Asn | Thr |
| 625 |     |     |     |     | 630 |     |     |     |     | 635 |     |     |     |     | 640 |
| Ser | Gln | Met | Ser | Met | Asp | His | Glu | Glu | Leu | Leu | Arg | Thr | Pro | Gly | Ala |
|     |     |     |     | 645 |     |     |     |     | 650 |     |     |     |     | 655 |     |
| Ser | Leu | Arg | Lys | Gly | Lys | Gly | Asn | Ser | Ser | Met | Asp | Ser | Ala | Ala | Gly |
|     |     |     |     | 660 |     |     |     |     | 665 |     |     |     |     | 670 |     |
| Cys | Ser | Gly | Thr | Pro | Pro | Ile | Cys | Arg | Gln | Ala | Gln | Thr | Lys | Leu | Glu |
|     |     | 675 |     |     |     |     | 680 |     |     |     |     | 685 |     |     |     |

```
Val  Ala  Leu  Tyr  Met  Phe  Leu  Trp  Asn  Pro  Asp  Thr  Glu  Ala  Val  Leu
690            695                 700
Val  Ala  Met  Ser  Cys  Phe  Arg  His  Leu  Cys  Glu  Glu  Ala  Asp  Ile  Arg
705            710                 715                           720
Cys  Ala  Val  Asp  Glu  Val  Ser  Val  His  Asn  Leu  Leu  Pro  Asn  Tyr  Asn
               725                 730                           735
Thr  Phe  Met  Glu  Phe  Ala  Ser  Val  Ser  Asn  Met  Met  Ser  Thr  Gly  Arg
               740                 745                 750
Ala  Ala  Leu  Gln  Lys  Arg  Val  Met  Ala  Leu  Leu  Arg  Arg  Ile  Glu  His
          755                 760                      765
Pro  Thr  Ala  Gly  Asn  Thr  Glu  Ala  Trp  Glu  Asp  Thr  His  Ala  Lys  Trp
770                      775                 780
Glu  Gln  Ala  Thr  Lys  Leu  Ile  Leu  Asn  Tyr  Pro  Lys  Ala  Lys  Met  Glu
785                      790                 795                           800
Asp  Gly  Gln  Ala  Ala  Glu  Ser  Leu  His  Lys  Thr  Ile  Val  Lys  Arg  Arg
               805                 810                           815
Met  Ser  His  Val  Ser  Gly  Gly  Gly  Ser  Ile  Asp  Leu  Ser  Asp  Thr  Asp
               820            825                      830
Ser  Leu  Gln  Glu  Trp  Ile  Asn  Met  Thr  Gly  Phe  Leu  Cys  Ala  Leu  Gly
          835                 840                      845
Gly  Val  Cys  Leu  Gln  Gln  Arg  Ser  Asn  Ser  Gly  Leu  Ala  Thr  Tyr  Ser
850                      855                      860
Pro  Pro  Met  Gly  Pro  Val  Ser  Glu  Arg  Lys  Gly  Ser  Met  Ile  Ser  Val
865                 870                 875                           880
Met  Ser  Ser  Glu  Gly  Asn  Ala  Asp  Thr  Pro  Val  Ser  Lys  Phe  Met  Asp
               885                 890                      895
Arg  Leu  Leu  Ser  Leu  Met  Val  Cys  Asn  His  Glu  Lys  Val  Gly  Leu  Gln
               900                 905                      910
Ile  Arg  Thr  Asn  Val  Lys  Asp  Leu  Val  Gly  Leu  Glu  Leu  Ser  Pro  Ala
          915                 920                 925
Leu  Tyr  Pro  Met  Leu  Phe  Asn  Lys  Leu  Lys  Asn  Thr  Ile  Ser  Lys  Phe
          930                 935                 940
Phe  Asp  Ser  Gln  Gly  Gln  Val  Leu  Leu  Thr  Asp  Thr  Asn  Thr  Gln  Phe
945                      950                 955                           960
Val  Glu  Gln  Thr  Ile  Ala  Ile  Met  Asn  Asn  Leu  Leu  Asp  Asn  His  Thr
               965                 970                           975
Glu  Gly  Ser  Ser  Glu  His  Leu  Gly  Gln  Ala  Ser  Ile  Glu  Thr  Met  Met
               980                 985                      990
Leu  Asn  Leu  Val  Arg  Tyr  Val  Arg  Val  Leu  Gly  Asn  Met  Val  His  Ala
          995                 1000                1005
Ile  Gln  Ile  Lys  Thr  Lys  Leu  Cys  Gln  Leu  Val  Glu  Val  Met  Met  Ala
          1010                1015                1020
Arg  Arg  Asp  Asp  Leu  Ser  Phe  Cys  Gln  Glu  Met  Lys  Phe  Arg  Asn  Lys
1025                     1030                1035                          1040
Met  Val  Glu  Tyr  Leu  Thr  Asp  Trp  Val  Met  Gly  Thr  Ser  Asn  Gln  Ala
               1045                1050                          1055
Ala  Asp  Asp  Asp  Val  Lys  Cys  Leu  Thr  Arg  Asp  Leu  Asp  Gln  Ala  Ser
               1060                1065                1070
Met  Glu  Ala  Val  Val  Ser  Leu  Leu  Ala  Gly  Leu  Pro  Leu  Gln  Pro  Glu
               1075                1080                1085
Glu  Gly  Asp  Gly  Val  Glu  Leu  Met  Glu  Ala  Lys  Ser  Gln  Leu  Phe  Leu
          1090                1095                1100
Lys  Tyr  Phe  Thr  Leu  Phe  Met  Asn  Leu  Leu  Asn  Asp  Cys  Ser  Glu  Val
1105                     1110                1115                          1120
```

```
Glu  Asp  Glu  Ser  Ala  Gln  Thr  Gly  Gly  Arg  Lys  Arg  Gly  Met  Ser  Arg
                    1125                1130                     1135

Arg  Leu  Ala  Ser  Leu  Arg  His  Cys  Thr  Val  Leu  Ala  Met  Ser  Asn  Leu
     1140                1145                     1150

Leu  Asn  Ala  Asn  Val  Asp  Ser  Gly  Leu  Met  His  Ser  Ile  Gly  Leu  Gly
          1155                1160                     1165

Tyr  His  Lys  Asp  Leu  Gln  Thr  Arg  Ala  Thr  Phe  Met  Glu  Val  Leu  Thr
               1170                1175                     1180

Lys  Ile  Leu  Gln  Gln  Gly  Thr  Glu  Phe  Asp  Thr  Leu  Ala  Glu  Thr  Val
1185                1190                     1195                          1200

Leu  Ala  Asp  Arg  Phe  Glu  Arg  Leu  Val  Glu  Leu  Val  Thr  Met  Met  Gly
                    1205                1210                     1215

Asp  Gln  Gly  Glu  Leu  Pro  Ile  Ala  Met  Ala  Leu  Ala  Asn  Val  Val  Pro
               1220                1225                     1230

Cys  Ser  Gln  Trp  Asp  Glu  Leu  Ala  Arg  Val  Leu  Val  Thr  Leu  Phe  Asp
          1235                1240                     1245

Ser  Arg  His  Leu  Leu  Tyr  Gln  Leu  Leu  Trp  Asn  Met  Phe  Ser  Lys  Glu
               1250                1255                     1260

Val  Glu  Leu  Ala  Asp  Ser  Met  Gln  Thr  Leu  Phe  Arg  Gly  Asn  Ser  Leu
1265                1270                     1275                          1280

Ala  Ser  Lys  Ile  Met  Thr  Phe  Cys  Phe  Lys  Val  Tyr  Gly  Ala  Thr  Tyr
                    1285                1290                     1295

Leu  Gln  Lys  Leu  Leu  Asp  Pro  Leu  Leu  Arg  Ile  Val  Ile  Thr  Ser  Ser
               1300                1305                     1310

Asp  Trp  Gln  His  Val  Ser  Phe  Glu  Val  Asp  Pro  Thr  Arg  Leu  Glu  Pro
          1315                1320                     1325

Ser  Glu  Ser  Leu  Glu  Glu  Asn  Gln  Arg  Asn  Leu  Leu  Gln  Met  Thr  Glu
               1330                1335                     1340

Lys  Phe  Phe  His  Ala  Ile  Ile  Ser  Ser  Ser  Glu  Phe  Pro  Pro  Gln
1345                1350                     1355                          1360

Leu  Arg  Ser  Val  Cys  His  Cys  Leu  Tyr  Gln  Val  Val  Ser  Gln  Arg  Phe
                    1365                1370                     1375

Pro  Gln  Asn  Ser  Ile  Gly  Ala  Val  Gly  Ser  Ala  Met  Phe  Leu  Arg  Phe
               1380                1385                     1390

Ile  Asn  Pro  Ala  Ile  Val  Ser  Pro  Tyr  Glu  Ala  Gly  Ile  Leu  Asp  Lys
          1395                1400                     1405

Lys  Pro  Pro  Pro  Arg  Ile  Glu  Arg  Gly  Leu  Lys  Leu  Met  Ser  Lys  Ile
     1410                1415                     1420

Leu  Gln  Ser  Ile  Ala  Asn  His  Val  Leu  Phe  Thr  Lys  Glu  Glu  His  Met
1425                1430                     1435                          1440

Arg  Pro  Phe  Asn  Asp  Phe  Val  Lys  Ser  Asn  Phe  Asp  Ala  Ala  Arg  Arg
                    1445                1450                     1455

Phe  Phe  Leu  Asp  Ile  Ala  Ser  Asp  Cys  Pro  Thr  Ser  Asp  Ala  Val  Asn
               1460                1465                     1470

His  Ser  Leu  Ser  Phe  Ile  Ser  Asp  Gly  Asn  Val  Leu  Ala  Leu  His  Arg
          1475                1480                     1485

Leu  Leu  Trp  Asn  Asn  Gln  Glu  Lys  Ile  Gly  Gln  Tyr  Leu  Ser  Ser  Asn
     1490                1495                     1500

Arg  Asp  His  Lys  Ala  Val  Gly  Arg  Arg  Pro  Phe  Asp  Lys  Met  Ala  Thr
1505                1510                     1515                          1520

Leu  Leu  Ala  Tyr  Leu  Gly  Pro  Pro  Glu  His  Lys  Pro  Val  Ala  Asp  Thr
                    1525                1530                     1535

His  Trp  Ser  Ser  Leu  Asn  Leu  Thr  Ser  Ser  Lys  Phe  Glu  Glu  Phe  Met
```

-continued

```
                        1540                    1545                    1550
     Thr  Arg  His  Gln  Val  His  Glu  Lys  Glu  Glu  Phe  Lys  Ala  Leu  Lys  Thr
                   1555                    1560                    1565
     Leu  Ser  Ile  Phe  Tyr  Gln  Ala  Gly  Thr  Ser  Lys  Ala  Gly  Asn  Pro  Ile
               1570                    1575                    1580
     Phe  Tyr  Tyr  Val  Ala  Arg  Arg  Phe  Lys  Thr  Gly  Gln  Ile  Asn  Gly  Asp
1585                    1590                    1595                    1600
     Leu  Leu  Ile  Tyr  His  Val  Leu  Leu  Thr  Leu  Lys  Pro  Tyr  Tyr  Ala  Lys
                    1605                    1610                    1615
     Pro  Tyr  Glu  Ile  Val  Val  Asp  Leu  Thr  His  Thr  Gly  Pro  Ser  Asn  Arg
                    1620                    1625                    1630
     Phe  Lys  Thr  Asp  Phe  Leu  Ser  Lys  Trp  Phe  Val  Val  Phe  Pro  Gly  Phe
                    1635                    1640                    1645
     Ala  Tyr  Asp  Asn  Val  Ser  Ala  Val  Tyr  Ile  Tyr  Asn  Cys  Asn  Ser  Trp
               1650                    1655                    1660
     Val  Arg  Glu  Tyr  Thr  Lys  Tyr  His  Glu  Arg  Leu  Leu  Thr  Gly  Leu  Lys
1665                    1670                    1675                    1680
     Gly  Ser  Lys  Arg  Leu  Val  Phe  Ile  Asp  Cys  Pro  Gly  Lys  Leu  Ala  Glu
                    1685                    1690                    1695
     His  Ile  Glu  His  Glu  Gln  Gln  Lys  Leu  Pro  Ala  Ala  Thr  Leu  Ala  Leu
                    1700                    1705                    1710
     Glu  Glu  Asp  Leu  Lys  Val  Phe  His  Asn  Ala  Leu  Lys  Leu  Ala  His  Lys
                    1715                    1720                    1725
     Asp  Thr  Lys  Val  Ser  Ile  Lys  Val  Gly  Ser  Thr  Ala  Val  Gln  Val  Thr
                    1730                    1735                    1740
     Ser  Ala  Glu  Arg  Thr  Lys  Val  Leu  Gly  Gln  Ser  Val  Phe  Leu  Asn  Asp
1745                    1750                    1755                    1760
     Ile  Tyr  Tyr  Ala  Ser  Glu  Ile  Glu  Glu  Ile  Cys  Leu  Val  Asp  Glu  Asn
                    1765                    1770                    1775
     Gln  Phe  Thr  Leu  Thr  Ile  Ala  Asn  Gln  Gly  Thr  Pro  Leu  Thr  Phe  Met
                    1780                    1785                    1790
     His  Gln  Glu  Cys  Glu  Ala  Ile  Val  Gln  Ser  Ile  Ile  His  Ile  Arg  Thr
                    1795                    1800                    1805
     Arg  Trp  Glu  Leu  Ser  Gln  Pro  Asp  Ser  Ile  Pro  Gln  His  Thr  Lys  Ile
                    1810                    1815                    1820
     Arg  Pro  Lys  Asp  Val  Pro  Gly  Thr  Leu  Leu  Asn  Ile  Ala  Leu  Leu  Asn
1825                    1830                    1835                    1840
     Leu  Gly  Ser  Ser  Asp  Pro  Ser  Leu  Arg  Ser  Ala  Ala  Tyr  Asn  Leu  Leu
                    1845                    1850                    1855
     Cys  Ala  Leu  Thr  Cys  Thr  Phe  Asn  Leu  Lys  Ile  Glu  Gly  Gln  Leu  Leu
                    1860                    1865                    1870
     Glu  Thr  Ser  Gly  Leu  Cys  Ile  Pro  Ala  Asn  Asn  Thr  Leu  Phe  Ile  Val
                    1875                    1880                    1885
     Ser  Ile  Ser  Lys  Thr  Leu  Ala  Ala  Asn  Glu  Pro  His  Leu  Thr  Leu  Glu
                    1890                    1895                    1900
     Phe  Leu  Glu  Glu  Cys  Ile  Ser  Gly  Phe  Ser  Lys  Ser  Ser  Ile  Glu  Leu
1905                    1910                    1915                    1920
     Lys  His  Leu  Cys  Leu  Glu  Tyr  Met  Thr  Pro  Trp  Leu  Ser  Asn  Leu  Val
                    1925                    1930                    1935
     Arg  Phe  Cys  Lys  His  Asn  Asp  Asp  Ala  Lys  Arg  Gln  Arg  Val  Thr  Ala
                    1940                    1945                    1950
     Ile  Leu  Asp  Lys  Leu  Ile  Thr  Met  Thr  Ile  Asn  Glu  Lys  Gln  Met  Tyr
                    1955                    1960                    1965
```

```
Pro Ser Ile Gln Ala Lys Ile Trp Gly Ser Leu Gly Gln Ile Thr Asp
    1970                1975                1980
Leu Leu Asp Val Val Leu Asp Ser Phe Ile Lys Thr Ser Ala Thr Gly
1985            1990                1995                    2000
Gly Leu Gly Ser Ile Lys Ala Glu Val Met Ala Asp Thr Ala Val Ala
                2005            2010                2015
Leu Ala Ser Gly Asn Val Lys Leu Val Ser Ser Lys Val Ile Gly Arg
            2020            2025            2030
Met Cys Lys Ile Ile Asp Lys Thr Cys Leu Ser Pro Thr Pro Thr Leu
        2035            2040                2045
Glu Gln His Leu Met Trp Asp Asp Ile Ala Ile Leu Ala Arg Tyr Met
        2050            2055            2060
Leu Met Leu Ser Phe Asn Asn Ser Leu Asp Val Ala Ala His Leu Pro
2065            2070            2075                    2080
Tyr Leu Phe His Val Val Thr Phe Leu Val Ala Thr Gly Pro Leu Ser
                2085            2090                2095
Leu Arg Ala Ser Thr His Gly Leu Val Ile Asn Ile Ile His Ser Leu
            2100        2105                2110
Cys Thr Cys Ser Gln Leu His Phe Ser Glu Glu Thr Lys Gln Val Leu
        2115            2120                2125
Arg Leu Ser Leu Thr Glu Phe Ser Leu Pro Lys Phe Tyr Leu Leu Phe
        2130            2135                2140
Gly Ile Ser Lys Val Lys Ser Ala Ala Val Ile Ala Phe Arg Ser Ser
2145            2150                2155                2160
Tyr Arg Asp Arg Ser Phe Ser Pro Gly Ser Tyr Glu Arg Glu Thr Phe
                2165            2170            2175
Ala Leu Thr Ser Leu Glu Thr Val Thr Glu Ala Leu Leu Glu Ile Met
            2180            2185                2190
Glu Ala Cys Met Arg Asp Ile Pro Thr Cys Lys Trp Leu Asp Gln Trp
        2195            2200            2205
Thr Glu Leu Ala Gln Arg Phe Ala Phe Gln Tyr Asn Pro Ser Leu Gln
        2210            2215            2220
Pro Arg Ala Leu Val Val Phe Gly Cys Ile Ser Lys Arg Val Ser His
2225            2230            2235                    2240
Gly Gln Ile Lys Gln Ile Ile Arg Ile Leu Ser Lys Ala Leu Glu Ser
                2245            2250            2255
Cys Leu Lys Gly Pro Asp Thr Tyr Asn Ser Gln Val Leu Ile Glu Ala
            2260            2265            2270
Thr Val Ile Ala Leu Thr Lys Leu Gln Pro Leu Leu Asn Lys Asp Ser
            2275            2280            2285
Pro Leu His Lys Ala Leu Phe Trp Val Ala Val Ala Val Leu Gln Leu
            2290            2295            2300
Asp Glu Val Asn Leu Tyr Ser Ala Gly Thr Ala Leu Leu Glu Gln Asn
2305            2310            2315                    2320
Leu His Thr Leu Asp Ser Leu Arg Ile Phe Asn Asp Lys Ser Pro Glu
            2325            2330            2335
Glu Val Phe Met Ala Ile Arg Asn Pro Leu Glu Trp His Cys Lys Gln
            2340            2345            2350
Met Asp His Phe Val Gly Leu Asn Phe Asn Ser Asn Phe Asn Phe Ala
        2355            2360            2365
Leu Val Gly His Leu Leu Lys Gly Tyr Arg His Pro Ser Pro Ala Ile
        2370            2375            2380
Val Ala Arg Thr Val Arg Ile Leu His Thr Leu Leu Thr Leu Val Asn
2385            2390            2395                    2400
```

```
Lys His Arg Asn Cys Asp Lys Phe Glu Val Asn Thr Gln Ser Val Ala
                2405                2410                2415

Tyr Leu Ala Ala Leu Leu Thr Val Ser Glu Glu Val Arg Ser Arg Cys
                2420                2425                2430

Ser Leu Lys His Arg Lys Ser Leu Leu Leu Thr Asp Ile Ser Met Glu
                2435                2440                2445

Asn Val Pro Met Asp Thr Tyr Pro Ile His His Gly Asp Pro Ser Tyr
            2450                2455                2460

Arg Thr Leu Lys Glu Thr Gln Pro Trp Ser Pro Lys Gly Ser Glu
2465                2470                2475                2480

Gly Tyr Leu Ala Ala Thr Tyr Pro Thr Val Gly Gln Thr Ser Pro Arg
                            2485                2490                2495

Ala Arg Lys Ser Met Ser Leu Asp Met Gly Gln Pro Ser Gln Ala Asn
                2500                2505                2510

Thr Lys Lys Leu Leu Gly Thr Arg Lys Ser Phe Asp His Leu Ile Ser
                2515                2520                2525

Asp Thr Lys Ala Pro Lys Arg Gln Glu Met Glu Ser Gly Ile Thr Thr
                2530                2535                2540

Pro Pro Lys Met Arg Arg Val Ala Glu Thr Asp Tyr Glu Met Glu Thr
2545                2550                2555                2560

Gln Arg Ile Ser Ser Ser Gln Gln His Pro His Leu Arg Lys Val Ser
                            2565                2570                2575

Val Ser Glu Ser Asn Val Leu Leu Asp Glu Glu Val Leu Thr Asp Pro
                2580                2585                2590

Lys Ile Gln Ala Leu Leu Leu Thr Val Leu Ala Thr Leu Val Lys Tyr
                2595                2600                2605

Thr Thr Asp Glu Phe Asp Gln Arg Ile Leu Tyr Glu Tyr Leu Ala Glu
            2610                2615                2620

Ala Ser Val Val Phe Pro Lys Val Phe Pro Val Val His Asn Leu Leu
2625                2630                2635                2640

Asp Ser Lys Ile Asn Thr Leu Leu Ser Leu Cys Gln Asp Pro Asn Leu
                            2645                2650                2655

Leu Asn Pro Ile His Gly Ile Val Gln Ser Val Val Tyr His Glu Glu
                2660                2665                2670

Ser Pro Pro Gln Tyr Gln Thr Ser Tyr Leu Gln Ser Phe Gly Phe Asn
                2675                2680                2685

Gly Leu Trp Arg Phe Ala Gly Pro Phe Ser Lys Gln Thr Gln Ile Pro
            2690                2695                2700

Asp Tyr Ala Glu Leu Ile Val Lys Phe Leu Asp Ala Leu Ile Asp Thr
2705                2710                2715                2720

Tyr Leu Pro Gly Ile Asp Glu Glu Thr Ser Glu Glu Ser Leu Leu Thr
                            2725                2730                2735

Pro Thr Ser Pro Tyr Pro Pro Ala Leu Gln Ser Gln Leu Ser Ile Thr
                2740                2745                2750

Ala Asn Leu Asn Leu Ser Asn Ser Met Thr Ser Leu Ala Thr Ser Gln
                2755                2760                2765

His Ser Pro Gly Ile Asp Lys Glu Asn Val Glu Leu Ser Pro Thr Thr
            2770                2775                2780

Gly His Cys Asn Ser Gly Arg Thr Arg His Gly Ser Ala Ser Gln Val
2785                2790                2795                2800

Gln Lys Gln Arg Ser Ala Gly Ser Phe Lys Arg Asn Ser Ile Lys Lys
                            2805                2810                2815

Ile Val
```

( 2 ) INFORMATION FOR SEQ ID NO:3:

( i ) SEQUENCE CHARACTERISTICS:
( A ) LENGTH: 2012 base pairs
( B ) TYPE: nucleic acid
( C ) STRANDEDNESS: single
( D ) TOPOLOGY: linear ( i i ) MOLECULE TYPE: cDNA to mRNA ( i i i ) HYPOTHETICAL: NO ( i v ) ANTI-SENSE: NO ( v ) FRAGMENT TYPE: C-terminal ( v i ) ORIGINAL SOURCE:
( A ) ORGANISM: Homo Sapiens ( v i i ) IMMEDIATE SOURCE:
( A ) LIBRARY: several overlapping cDNA's ( v i i i ) POSITION IN GENOME:
( A ) CHROMOSOME/SEGMENT: 17q11.2

( i x ) FEATURE:
( A ) NAME/KEY: CDS
( B ) LOCATION: 1..1833

( i x ) FEATURE:
( A ) NAME/KEY: misc_feature
( B ) LOCATION: group(34..36, 1642..1644)
( D ) OTHER INFORMATION: /note= "Potential N-glycosylation site"

( i x ) FEATURE:
( A ) NAME/KEY: misc_signal
( B ) LOCATION: group(859..873, 967..981, 1012..1026)
( D ) OTHER INFORMATION: /note= "Possible nuclear localization signals"

( i x ) FEATURE:
( A ) NAME/KEY: misc_feature
( B ) LOCATION: 1210..1236
( D ) OTHER INFORMATION: /note= "PCR primer A"

( i x ) FEATURE:
( A ) NAME/KEY: misc_feature
( B ) LOCATION: 1441..1464
( D ) OTHER INFORMATION: /note= "PCR primer C"

( i x ) FEATURE:
( A ) NAME/KEY: misc_feature
( B ) LOCATION: 1594..1620
( D ) OTHER INFORMATION: /note= "PCR primer B"

( i x ) FEATURE:
( A ) NAME/KEY: misc_feature
( B ) LOCATION: 1914..1939
( D ) OTHER INFORMATION: /note= "PCR primer D"

( i x ) FEATURE:
( A ) NAME/KEY: misc_feature
( B ) LOCATION: 1..2012
( D ) OTHER INFORMATION: /note= "Clone P5"

( i x ) FEATURE:
( A ) NAME/KEY: misc_feature
( B ) LOCATION: 1570..2012
( D ) OTHER INFORMATION: /note= "Clone B3A"

( x ) PUBLICATION INFORMATION:
( A ) AUTHORS: Wallace, M.R. et al.
( B ) TITLE: Type 1 Neurofibromatosis Gene
( C ) JOURNAL: Science
( D ) VOLUME: 250
( E ) ISSUE: 12/21/90
( F ) PAGES: 1749-

(G) DATE: 12/21-1990
(K) RELEVANT RESIDUES IN SEQ ID NO:3: FROM 1 TO 2012

(x) PUBLICATION INFORMATION:
(A) AUTHORS: Wallace, M.R. et al.
(B) TITLE: Type 1 Neurofibromatosis Gene: Identification of a Large Transcript in Three NF1 Patients
(C) JOURNAL: Science
(D) VOLUME: 249
(E) ISSUE: 07/13/90
(F) PAGES: 181-186
(G) DATE: 07/13-1990
(K) RELEVANT RESIDUES IN SEQ ID NO:3: FROM 1 TO 2012

(xi) SEQUENCE DESCRIPTION: SEQ ID NO:3:

```
ACA GAA CTA GCT CAA AGA TTT GCA TTC CAA TAT AAT CCA TCC CTG CAA          48
Thr Glu Leu Ala Gln Arg Phe Ala Phe Gln Tyr Asn Pro Ser Leu Gln
 1               5                  10                  15

CCA AGA GCT CTT GTT GTC TTT GGG TGT ATT AGC AAA CGA GTG TCT CAT          96
Pro Arg Ala Leu Val Val Phe Gly Cys Ile Ser Lys Arg Val Ser His
            20                  25                  30

GGG CAG ATA AAG CAG ATA ATC CGT ATT CTT AGC AAG GCA CTT GAG AGT         144
Gly Gln Ile Lys Gln Ile Ile Arg Ile Leu Ser Lys Ala Leu Glu Ser
                35                  40                  45

TGC TTA AAA GGA CCT GAC ACT TAC AAC AGT CAA GTT CTG ATA GAA GCT         192
Cys Leu Lys Gly Pro Asp Thr Tyr Asn Ser Gln Val Leu Ile Glu Ala
    50                  55                  60

ACA GTA ATA GCA CTA ACC AAA TTA CAG CCA CTT CTT AAT AAG GAC TCG         240
Thr Val Ile Ala Leu Thr Lys Leu Gln Pro Leu Leu Asn Lys Asp Ser
65                  70                  75                  80

CCT CTG CAC AAA GCC CTC TTT TGG GTA GCT GTG GCT GTG CTG CAG CTT         288
Pro Leu His Lys Ala Leu Phe Trp Val Ala Val Ala Val Leu Gln Leu
                85                  90                  95

GAT GAG GTC AAC TTG TAT TCA GCA GGT ACC GCA CTT CTT GAA CAA AAC         336
Asp Glu Val Asn Leu Tyr Ser Ala Gly Thr Ala Leu Leu Glu Gln Asn
                100                 105                 110

CTG CAT ACT TTA GAT AGT CTC CGT ATA TTC AAT GAC AAG AGT CCA GAG         384
Leu His Thr Leu Asp Ser Leu Arg Ile Phe Asn Asp Lys Ser Pro Glu
        115                 120                 125

GAA GTA TTT ATG GCA ATC CGG AAT CCT CTG GAG TGG CAC TGC AAG CAA         432
Glu Val Phe Met Ala Ile Arg Asn Pro Leu Glu Trp His Cys Lys Gln
        130                 135                 140

ATG GAT CAT TTT GTT GGA CTC AAT TTC AAC TCT AAC TTT AAC TTT GCA         480
Met Asp His Phe Val Gly Leu Asn Phe Asn Ser Asn Phe Asn Phe Ala
145                 150                 155                 160

TTG GTT GGA CAC CTT TTA AAA GGG TAC AGG CAT CCT TCA CCT GCT ATT         528
Leu Val Gly His Leu Leu Lys Gly Tyr Arg His Pro Ser Pro Ala Ile
                165                 170                 175

GTT GCA AGA ACA GTC AGA ATT TTA CAT ACA CTA CTA ACT CTG GTT AAC         576
Val Ala Arg Thr Val Arg Ile Leu His Thr Leu Leu Thr Leu Val Asn
            180                 185                 190

AAA CAC AGA AAT TGT GAC AAA TTT GAA GTG AAT ACA CAG AGC GTG GCC         624
Lys His Arg Asn Cys Asp Lys Phe Glu Val Asn Thr Gln Ser Val Ala
        195                 200                 205

TAC TTA GCA GCT TTA CTT ACA GTG TCT GAA GAA GTT CGA AGT CGC TGC         672
Tyr Leu Ala Ala Leu Leu Thr Val Ser Glu Glu Val Arg Ser Arg Cys
    210                 215                 220

AGC CTA AAA CAT AGA AAG TCA CTT CTT CTT ACT GAT ATT TCA ATG GAA         720
Ser Leu Lys His Arg Lys Ser Leu Leu Leu Thr Asp Ile Ser Met Glu
225                 230                 235                 240

AAT GTT CCT ATG GAT ACA TAT CCC ATT CAT CAT GGT GAC CCT TCC TAT         768
Asn Val Pro Met Asp Thr Tyr Pro Ile His His Gly Asp Pro Ser Tyr
                245                 250                 255
```

| | | | | | | | | | | | | | | | | |
|---|---|---|---|---|---|---|---|---|---|---|---|---|---|---|---|---|
| AGG | ACA | CTA | AAG | GAG | ACT | CAG | CCA | TGG | TCC | TCT | CCC | AAA | GGT | TCT | GAA | 816 |
| Arg | Thr | Leu | Lys 260 | Glu | Thr | Gln | Pro 265 | Trp | Ser | Ser | Pro | Lys 270 | Gly | Ser | Glu | |
| GGA | TAC | CTT | GCA | GCC | ACC | TAT | CCA | ACT | GTC | GGC | CAG | ACC | AGT | CCC | CGA | 864 |
| Gly | Tyr | Leu 275 | Ala | Ala | Thr | Tyr | Pro 280 | Thr | Val | Gly | Gln | Thr 285 | Ser | Pro | Arg | |
| GCC | AGG | AAA | TCC | ATG | AGC | CTG | GAC | ATG | GGG | CAA | CCT | TCT | CAG | GCC | AAC | 912 |
| Ala | Arg 290 | Lys | Ser | Met | Ser 295 | Leu | Asp | Met | Gly | Gln 300 | Pro | Ser | Gln | Ala | Asn | |
| ACT | AAG | AAG | TTG | CTT | GGA | ACA | AGG | AAA | AGT | TTT | GAT | CAC | TTG | ATA | TCA | 960 |
| Thr 305 | Lys | Lys | Leu | Leu | Gly 310 | Thr | Arg | Lys | Ser | Phe 315 | Asp | His | Leu | Ile | Ser 320 | |
| GAC | ACA | AAG | GCT | CCT | AAA | AGG | CAA | GAA | ATG | GAA | TCA | GGG | ATC | ACA | ACA | 1008 |
| Asp | Thr | Lys | Ala | Pro 325 | Lys | Arg | Gln | Glu | Met 330 | Glu | Ser | Gly | Ile | Thr 335 | Thr | |
| CCC | CCC | AAA | ATG | AGG | AGA | GTA | GCA | GAA | ACT | GAT | TAT | GAA | ATG | GAA | ACT | 1056 |
| Pro | Pro | Lys | Met 340 | Arg | Arg | Val | Ala | Glu 345 | Thr | Asp | Tyr | Glu | Met 350 | Glu | Thr | |
| CAG | AGG | ATT | TCC | TCA | TCA | CAA | CAG | CAC | CCA | CAT | TTA | CGT | AAA | GTT | TCA | 1104 |
| Gln | Arg | Ile 355 | Ser | Ser | Ser | Gln | Gln 360 | His | Pro | His | Leu | Arg 365 | Lys | Val | Ser | |
| GTG | TCT | GAA | TCA | AAT | GTT | CTC | TTG | GAT | GAA | GAA | GTA | CTT | ACT | GAT | CCG | 1152 |
| Val | Ser 370 | Glu | Ser | Asn | Val 375 | Leu | Leu | Asp | Glu | Glu 380 | Val | Leu | Thr | Asp | Pro | |
| AAG | ATC | CAG | GCG | CTG | CTT | CTT | ACT | GTT | CTA | GCT | ACA | CTG | GTA | AAA | TAT | 1200 |
| Lys 385 | Ile | Gln | Ala | Leu | Leu 390 | Leu | Thr | Val | Leu | Ala 395 | Thr | Leu | Val | Lys | Tyr 400 | |
| ACC | ACA | GAT | GAG | TTT | GAT | CAA | CGA | ATT | CTT | TAT | GAA | TAC | TTA | GCA | GAG | 1248 |
| Thr | Thr | Asp | Glu | Phe 405 | Asp | Gln | Arg | Ile | Leu 410 | Tyr | Glu | Tyr | Leu | Ala 415 | Glu | |
| GCC | AGT | GTT | GTG | TTT | CCC | AAA | GTC | TTT | CCT | GTT | GTG | CAT | AAT | TTG | TTG | 1296 |
| Ala | Ser | Val | Val 420 | Phe | Pro | Lys | Val | Phe 425 | Pro | Val | Val | His | Asn 430 | Leu | Leu | |
| GAC | TCT | AAG | ATC | AAC | ACC | CTG | TTA | TCA | TTG | TGC | CAA | GAT | CCA | AAT | TTG | 1344 |
| Asp | Ser | Lys 435 | Ile | Asn | Thr | Leu | Leu 440 | Ser | Leu | Cys | Gln | Asp 445 | Pro | Asn | Leu | |
| TTA | AAT | CCA | ATC | CAT | GGA | ATT | GTG | CAG | AGT | GTG | GTG | TAC | CAT | GAA | GAA | 1392 |
| Leu | Asn 450 | Pro | Ile | His | Gly 455 | Ile | Val | Gln | Ser | Val 460 | Val | Tyr | His | Glu | Glu | |
| TCC | CCA | CCA | CAA | TAC | CAA | ACA | TCT | TAC | CTG | CAA | AGT | TTT | GGT | TTT | AAT | 1440 |
| Ser 465 | Pro | Pro | Gln | Tyr | Gln 470 | Thr | Ser | Tyr | Leu | Gln 475 | Ser | Phe | Gly | Phe | Asn 480 | |
| GGC | TTG | TGG | CGG | TTT | GCA | GGA | CCG | TTT | TCA | AAG | CAA | ACA | CAA | ATT | CCA | 1488 |
| Gly | Leu | Trp | Arg | Phe 485 | Ala | Gly | Pro | Phe | Ser 490 | Lys | Gln | Thr | Gln | Ile 495 | Pro | |
| GAC | TAT | GCT | GAG | CTT | ATT | GTT | AAG | TTT | CTT | GAT | GCC | TTG | ATT | GAC | ACG | 1536 |
| Asp | Tyr | Ala | Glu 500 | Leu | Ile | Val | Lys | Phe 505 | Leu | Asp | Ala | Leu | Ile 510 | Asp | Thr | |
| TAC | CTG | CCT | GGA | ATT | GAT | GAA | GAA | ACC | AGT | GAA | GAA | TCC | CTC | CTG | ACT | 1584 |
| Tyr | Leu | Pro 515 | Gly | Ile | Asp | Glu | Glu 520 | Thr | Ser | Glu | Glu | Ser 525 | Leu | Leu | Thr | |
| CCC | ACA | TCT | CCT | TAC | CCT | CCT | GCA | CTG | CAG | AGC | CAG | CTT | AGT | ATC | ACT | 1632 |
| Pro | Thr | Ser | Pro 530 | Tyr | Pro | Pro | Ala | Leu 535 | Gln | Ser | Gln | Leu | Ser 540 | Ile | Thr | |
| GCC | AAC | CTT | AAC | CTT | TCT | AAT | TCC | ATG | ACC | TCA | CTT | GCA | ACT | TCC | CAG | 1680 |
| Ala 545 | Asn | Leu | Asn | Leu | Ser 550 | Asn | Ser | Met | Thr | Ser 555 | Leu | Ala | Thr | Ser | Gln 560 | |
| CAT | TCC | CCA | GGA | ATC | GAC | AAG | GAG | AAC | GTT | GAA | CTC | TCC | CCT | ACC | ACT | 1728 |
| His | Ser | Pro | Gly | Ile 565 | Asp | Lys | Glu | Asn | Val 570 | Glu | Leu | Ser | Pro | Thr 575 | Thr | |

```
GGC CAC TGT AAC AGT GGA CGA ACT CGC CAC GGA TCC GCA AGC CAA GTG        1776
Gly His Cys Asn Ser Gly Arg Thr Arg His Gly Ser Ala Ser Gln Val
        580                     585                 590

CAG AAG CAA AGA AGC GCT GGC AGT TTC AAA CGT AAT AGC ATT AAG AAG        1824
Gln Lys Gln Arg Ser Ala Gly Ser Phe Lys Arg Asn Ser Ile Lys Lys
        595                     600                 605

ATC GTG TGA AGCTTGCTTG CTTTCTTTTT TAAAATCAAC TTAACATGGG                1873
Ile Val *
610

CTCTTCACTA GTGACCCCTT CCCTGTCCTT GCCCTTTCCC CCCATGTTGT AATGCTGCAC      1933

TTCCTGTTTT ATAATGAACC CATCCGGTTT GCCATGTTGC CAGATGATCA ACTCTTCGAA      1993

GCCTTGCCTA AATTTAATG                                                    2012
```

( 2 ) INFORMATION FOR SEQ ID NO:4:

( i ) SEQUENCE CHARACTERISTICS:
( A ) LENGTH: 610 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Thr Glu Leu Ala Gln Arg Phe Ala Phe Gln Tyr Asn Pro Ser Leu Gln
 1               5                  10                  15

Pro Arg Ala Leu Val Val Phe Gly Cys Ile Ser Lys Arg Val Ser His
                20                  25                  30

Gly Gln Ile Lys Gln Ile Ile Arg Ile Leu Ser Lys Ala Leu Glu Ser
            35                  40                  45

Cys Leu Lys Gly Pro Asp Thr Tyr Asn Ser Gln Val Leu Ile Glu Ala
        50                  55                  60

Thr Val Ile Ala Leu Thr Lys Leu Gln Pro Leu Leu Asn Lys Asp Ser
65                  70                  75                  80

Pro Leu His Lys Ala Leu Phe Trp Val Ala Val Ala Val Leu Gln Leu
                85                  90                  95

Asp Glu Val Asn Leu Tyr Ser Ala Gly Thr Ala Leu Leu Glu Gln Asn
                100                 105                 110

Leu His Thr Leu Asp Ser Leu Arg Ile Phe Asn Asp Lys Ser Pro Glu
            115                 120                 125

Glu Val Phe Met Ala Ile Arg Asn Pro Leu Glu Trp His Cys Lys Gln
        130                 135                 140

Met Asp His Phe Val Gly Leu Asn Phe Asn Ser Asn Phe Asn Phe Ala
145                 150                 155                 160

Leu Val Gly His Leu Leu Lys Gly Tyr Arg His Pro Ser Pro Ala Ile
                165                 170                 175

Val Ala Arg Thr Val Arg Ile Leu His Thr Leu Leu Thr Leu Val Asn
            180                 185                 190

Lys His Arg Asn Cys Asp Lys Phe Glu Val Asn Thr Gln Ser Val Ala
        195                 200                 205

Tyr Leu Ala Ala Leu Leu Thr Val Ser Glu Glu Val Arg Ser Arg Cys
        210                 215                 220

Ser Leu Lys His Arg Lys Ser Leu Leu Leu Thr Asp Ile Ser Met Glu
225                 230                 235                 240

Asn Val Pro Met Asp Thr Tyr Pro Ile His His Gly Asp Pro Ser Tyr
                245                 250                 255

Arg Thr Leu Lys Glu Thr Gln Pro Trp Ser Ser Pro Lys Gly Ser Glu
            260                 265                 270
```

Gly Tyr Leu Ala Ala Thr Tyr Pro Thr Val Gly Gln Thr Ser Pro Arg
            275                 280                 285

Ala Arg Lys Ser Met Ser Leu Asp Met Gly Gln Pro Ser Gln Ala Asn
    290                 295                 300

Thr Lys Lys Leu Leu Gly Thr Arg Lys Ser Phe Asp His Leu Ile Ser
305                 310                 315                 320

Asp Thr Lys Ala Pro Lys Arg Gln Glu Met Glu Ser Gly Ile Thr Thr
                325                 330                 335

Pro Pro Lys Met Arg Arg Val Ala Glu Thr Asp Tyr Glu Met Glu Thr
            340                 345                 350

Gln Arg Ile Ser Ser Ser Gln Gln His Pro His Leu Arg Lys Val Ser
            355                 360                 365

Val Ser Glu Ser Asn Val Leu Leu Asp Glu Glu Val Leu Thr Asp Pro
    370                 375                 380

Lys Ile Gln Ala Leu Leu Leu Thr Val Leu Ala Thr Leu Val Lys Tyr
385                 390                 395                 400

Thr Thr Asp Glu Phe Asp Gln Arg Ile Leu Tyr Glu Tyr Leu Ala Glu
                405                 410                 415

Ala Ser Val Val Phe Pro Lys Val Phe Pro Val Val His Asn Leu Leu
            420                 425                 430

Asp Ser Lys Ile Asn Thr Leu Leu Ser Leu Cys Gln Asp Pro Asn Leu
            435                 440                 445

Leu Asn Pro Ile His Gly Ile Val Gln Ser Val Val Tyr His Glu Glu
    450                 455                 460

Ser Pro Pro Gln Tyr Gln Thr Ser Tyr Leu Gln Ser Phe Gly Phe Asn
465                 470                 475                 480

Gly Leu Trp Arg Phe Ala Gly Pro Phe Ser Lys Gln Thr Gln Ile Pro
            485                 490                 495

Asp Tyr Ala Glu Leu Ile Val Lys Phe Leu Asp Ala Leu Ile Asp Thr
                500                 505                 510

Tyr Leu Pro Gly Ile Asp Glu Glu Thr Ser Glu Glu Ser Leu Leu Thr
            515                 520                 525

Pro Thr Ser Pro Tyr Pro Pro Ala Leu Gln Ser Gln Leu Ser Ile Thr
    530                 535                 540

Ala Asn Leu Asn Leu Ser Asn Ser Met Thr Ser Leu Ala Thr Ser Gln
545                 550                 555                 560

His Ser Pro Gly Ile Asp Lys Glu Asn Val Glu Leu Ser Pro Thr Thr
                565                 570                 575

Gly His Cys Asn Ser Gly Arg Thr Arg His Gly Ser Ala Ser Gln Val
            580                 585                 590

Gln Lys Gln Arg Ser Ala Gly Ser Phe Lys Arg Asn Ser Ile Lys Lys
    595                 600                 605

Ile Val
    610

( 2 ) INFORMATION FOR SEQ ID NO:5:

( i ) SEQUENCE CHARACTERISTICS:
        ( A ) LENGTH: 1212 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo Sapiens ( i x ) FEATURE:
    ( A ) NAME/KEY: CDS
    ( B ) LOCATION: 211..1212

( i x ) FEATURE:
    ( A ) NAME/KEY: misc_feature
    ( B ) LOCATION: 52..54
    ( D ) OTHER INFORMATION: /note= "Upstream in frame stop codon"

( i x ) FEATURE:
    ( A ) NAME/KEY: misc_feature
    ( B ) LOCATION: 98..119
    ( D ) OTHER INFORMATION: /note= "Oligonucleotide used for primer extension"

( i x ) FEATURE:
    ( A ) NAME/KEY: misc_feature
    ( B ) LOCATION: (270  271)
    ( D ) OTHER INFORMATION: /note= "Position of the first intron and alternate sequences(SEQ ID NO:6 through SEQ ID NO:8) diverge"

( x i ) SEQUENCE DESCRIPTION: SEQ ID NO:5:

```
CCCCAGCCTC  CTTGCCAACC  CCCCTTTCCC  TCTCCCCCTC  CCGCTCGGCG  CTGACCCCCC        60

ATCCCCACCC  CCGTGGGAAC  ACTGGGAGCC  TGCACTCCAC  AGACCCTCTC  CTTGCCTCTT       120

CCCTCACCTC  AGCCTCCGCT  CCCCGCCCTC  TTCCCGGCCC  AGGGCGCCGG  CCCACCCTTC       180

CCTCCGCCGC  CCCCCGGCCG  CGGGGAGGAC  ATG GCC GCG CAC AGG CCG GTG GAA         234
                                   Met Ala Ala His Arg Pro Val Glu
                                                       615

TGG GTC CAG GCC GTG GTC AGC CGC TTC GAC GAG CAG CTT CCA ATA AAA           282
Trp Val Gln Ala Val Val Ser Arg Phe Asp Glu Gln Leu Pro Ile Lys
620             625                 630                 635

ACA GGA CAG CAG AAC ACA CAT ACC AAA GTC AGT ACT GAG CAC AAC AAG           330
Thr Gly Gln Gln Asn Thr His Thr Lys Val Ser Thr Glu His Asn Lys
                640             645                 650

GAA TGT CTA ATC AAT ATT TCC AAA TAC AAG TTT TCT TTG GTT ATA AGC           378
Glu Cys Leu Ile Asn Ile Ser Lys Tyr Lys Phe Ser Leu Val Ile Ser
            655             660                 665

GGC CTC ACT ACT ATT TTA AAG AAT GTT AAC AAT ATG AGA ATA TTT GGA           426
Gly Leu Thr Thr Ile Leu Lys Asn Val Asn Asn Met Arg Ile Phe Gly
        670             675                 680

GAA GCT GCT GAA AAA AAT TTA TAT CTC TCT CAG TTG ATT ATA TTG GAT           474
Glu Ala Ala Glu Lys Asn Leu Tyr Leu Ser Gln Leu Ile Ile Leu Asp
    685             690                 695

ACA CTG GAA AAA TGT CTT GCT GGG CAA CCA AAG GAC ACA ATG AGA TTA           522
Thr Leu Glu Lys Cys Leu Ala Gly Gln Pro Lys Asp Thr Met Arg Leu
700             705                 710                 715

GAT GAA ACG ATG CTG GTC AAA CAG TTG CTG CCA GAA ATC TGC CAT TTT           570
Asp Glu Thr Met Leu Val Lys Gln Leu Leu Pro Glu Ile Cys His Phe
            720                 725                 730

CTT CAC ACC TGT CGT GAA GGA AAC CAG CAT GCA GCT GAA CTT CGG AAT           618
Leu His Thr Cys Arg Glu Gly Asn Gln His Ala Ala Glu Leu Arg Asn
        735                 740                 745

TCT GCC TCT GGG GTT TTA TTT TCT CTC AGC TGC AAC AAC TTC AAT GCA           666
Ser Ala Ser Gly Val Leu Phe Ser Leu Ser Cys Asn Asn Phe Asn Ala
    750                 755                 760

GTC TTT AGT CGC ATT TCT ACC AGG TTA CAG GAA TTA ACT GTT TGT TCA           714
Val Phe Ser Arg Ile Ser Thr Arg Leu Gln Glu Leu Thr Val Cys Ser
765                 770                 775
```

-continued

| | | | | | | | | | | | | | | | | |
|---|---|---|---|---|---|---|---|---|---|---|---|---|---|---|---|---|
| GAA | GAC | AAT | GTT | GAT | GTT | CAT | GAT | ATA | GAA | TTG | TTA | CAG | TAT | ATC | AAT | 762 |
| Glu | Asp | Asn | Val | Asp | Val | His | Asp | Ile | Glu | Leu | Leu | Gln | Tyr | Ile | Asn | |
| 780 | | | | 785 | | | | | 790 | | | | | | 795 | |
| GTG | GAT | TGT | GCA | AAA | TTA | AAA | CGA | CTC | CTG | AAG | GAA | ACA | GCA | TTT | AAA | 810 |
| Val | Asp | Cys | Ala | Lys | Leu | Lys | Arg | Leu | Leu | Lys | Glu | Thr | Ala | Phe | Lys | |
| | | | 800 | | | | | 805 | | | | | 810 | | | |
| TTT | AAA | GCC | CTA | AAG | AAG | GTT | GCG | CAG | TTA | GCA | GTT | ATA | AAT | AGC | CTG | 858 |
| Phe | Lys | Ala | Leu | Lys | Lys | Val | Ala | Gln | Leu | Ala | Val | Ile | Asn | Ser | Leu | |
| | | | 815 | | | | 820 | | | | | 825 | | | | |
| GAA | AAG | GCA | TTT | TGG | AAC | TGG | GTA | GAA | AAT | TAT | CCA | GAT | GAA | TTT | ACA | 906 |
| Glu | Lys | Ala | Phe | Trp | Asn | Trp | Val | Glu | Asn | Tyr | Pro | Asp | Glu | Phe | Thr | |
| | | 830 | | | | | 835 | | | | | 840 | | | | |
| AAA | CTG | TAC | CAG | ATC | CCA | CAG | ACT | GAT | ATG | GCT | GAA | TGT | GCA | GAA | AAG | 954 |
| Lys | Leu | Tyr | Gln | Ile | Pro | Gln | Thr | Asp | Met | Ala | Glu | Cys | Ala | Glu | Lys | |
| | 845 | | | | | 850 | | | | | 855 | | | | | |
| CTA | TTT | GAC | TTG | GTG | GAT | GGT | TTT | GCT | GAA | AGC | ACC | AAA | CGT | AAA | GCA | 1002 |
| Leu | Phe | Asp | Leu | Val | Asp | Gly | Phe | Ala | Glu | Ser | Thr | Lys | Arg | Lys | Ala | |
| 860 | | | | | 865 | | | | | 870 | | | | | 875 | |
| GCA | GTT | TGG | CCA | CTA | CAA | ATC | ATT | CTC | CTT | ATC | TTG | TGT | CCA | GAA | ATA | 1050 |
| Ala | Val | Trp | Pro | Leu | Gln | Ile | Ile | Leu | Leu | Ile | Leu | Cys | Pro | Glu | Ile | |
| | | | | 880 | | | | | 885 | | | | | 890 | | |
| ATC | CAG | GAT | ATA | TCC | AAA | GAC | GTG | GTT | GAT | GAA | AAC | AAC | ATG | AAT | AAG | 1098 |
| Ile | Gln | Asp | Ile | Ser | Lys | Asp | Val | Val | Asp | Glu | Asn | Asn | Met | Asn | Lys | |
| | | | 895 | | | | | 900 | | | | | 905 | | | |
| AAG | TTA | TTT | CTG | GAC | AGT | CTA | CGA | AAA | GCT | CTT | GCT | GGC | CAT | GGA | GGA | 1146 |
| Lys | Leu | Phe | Leu | Asp | Ser | Leu | Arg | Lys | Ala | Leu | Ala | Gly | His | Gly | Gly | |
| | | 910 | | | | | 915 | | | | | 920 | | | | |
| AGT | AGG | CAG | CTG | ACA | GAA | AGT | GCT | GCA | ATT | GCC | TGT | GTC | AAA | CTG | TGT | 1194 |
| Ser | Arg | Gln | Leu | Thr | Glu | Ser | Ala | Ala | Ile | Ala | Cys | Val | Lys | Leu | Cys | |
| | 925 | | | | | 930 | | | | | 935 | | | | | |
| AAA | GCA | AGT | ACT | TAC | ATC | | | | | | | | | | | 1212 |
| Lys | Ala | Ser | Thr | Tyr | Ile | | | | | | | | | | | |
| 940 | | | | | 945 | | | | | | | | | | | |

(2) INFORMATION FOR SEQ ID NO:6:

(i) SEQUENCE CHARACTERISTICS:
        (A) LENGTH: 334 amino acids
        (B) TYPE: amino acid
        (D) TOPOLOGY: linear (ii) MOLECULE TYPE: protein (xi) SEQUENCE DESCRIPTION: SEQ ID NO:6:

| | | | | | | | | | | | | | | |
|---|---|---|---|---|---|---|---|---|---|---|---|---|---|---|
| Met | Ala | Ala | His | Arg | Pro | Val | Glu | Trp | Val | Gln | Ala | Val | Val | Ser | Arg |
| 1 | | | | 5 | | | | | 10 | | | | | 15 | |
| Phe | Asp | Glu | Gln | Leu | Pro | Ile | Lys | Thr | Gly | Gln | Gln | Asn | Thr | His | Thr |
| | | | 20 | | | | | 25 | | | | | 30 | | |
| Lys | Val | Ser | Thr | Glu | His | Asn | Lys | Glu | Cys | Leu | Ile | Asn | Ile | Ser | Lys |
| | | | 35 | | | | 40 | | | | | 45 | | | |
| Tyr | Lys | Phe | Ser | Leu | Val | Ile | Ser | Gly | Leu | Thr | Thr | Ile | Leu | Lys | Asn |
| | 50 | | | | | 55 | | | | | 60 | | | | |
| Val | Asn | Asn | Met | Arg | Ile | Phe | Gly | Glu | Ala | Ala | Glu | Lys | Asn | Leu | Tyr |
| 65 | | | | | 70 | | | | | 75 | | | | | 80 |
| Leu | Ser | Gln | Leu | Ile | Ile | Leu | Asp | Thr | Leu | Glu | Lys | Cys | Leu | Ala | Gly |
| | | | | 85 | | | | | 90 | | | | | 95 | |
| Gln | Pro | Lys | Asp | Thr | Met | Arg | Leu | Asp | Glu | Thr | Met | Leu | Val | Lys | Gln |
| | | | 100 | | | | | 105 | | | | | 110 | | |
| Leu | Leu | Pro | Glu | Ile | Cys | His | Phe | Leu | His | Thr | Cys | Arg | Glu | Gly | Asn |
| | | | 115 | | | | 120 | | | | | 125 | | | |

| Gln | His | Ala | Ala | Glu | Leu | Arg | Asn | Ser | Ala | Ser | Gly | Val | Leu | Phe | Ser |
|---|---|---|---|---|---|---|---|---|---|---|---|---|---|---|---|
| 130 | | | | | 135 | | | | | | 140 | | | | |

| Leu | Ser | Cys | Asn | Asn | Phe | Asn | Ala | Val | Phe | Ser | Arg | Ile | Ser | Thr | Arg |
|---|---|---|---|---|---|---|---|---|---|---|---|---|---|---|---|
| 145 | | | | | 150 | | | | 155 | | | | | | 160 |

| Leu | Gln | Glu | Leu | Thr | Val | Cys | Ser | Glu | Asp | Asn | Val | Asp | Val | His | Asp |
|---|---|---|---|---|---|---|---|---|---|---|---|---|---|---|---|
| | | | | 165 | | | | | 170 | | | | | 175 | |

| Ile | Glu | Leu | Leu | Gln | Tyr | Ile | Asn | Val | Asp | Cys | Ala | Lys | Leu | Lys | Arg |
|---|---|---|---|---|---|---|---|---|---|---|---|---|---|---|---|
| | | | 180 | | | | | 185 | | | | | 190 | | |

| Leu | Leu | Lys | Glu | Thr | Ala | Phe | Lys | Phe | Lys | Ala | Leu | Lys | Lys | Val | Ala |
|---|---|---|---|---|---|---|---|---|---|---|---|---|---|---|---|
| | | 195 | | | | | 200 | | | | | 205 | | | |

| Gln | Leu | Ala | Val | Ile | Asn | Ser | Leu | Glu | Lys | Ala | Phe | Trp | Asn | Trp | Val |
|---|---|---|---|---|---|---|---|---|---|---|---|---|---|---|---|
| | 210 | | | | | 215 | | | | | 220 | | | | |

| Glu | Asn | Tyr | Pro | Asp | Glu | Phe | Thr | Lys | Leu | Tyr | Gln | Ile | Pro | Gln | Thr |
|---|---|---|---|---|---|---|---|---|---|---|---|---|---|---|---|
| 225 | | | | | 230 | | | | | 235 | | | | | 240 |

| Asp | Met | Ala | Glu | Cys | Ala | Glu | Lys | Leu | Phe | Asp | Leu | Val | Asp | Gly | Phe |
|---|---|---|---|---|---|---|---|---|---|---|---|---|---|---|---|
| | | | | 245 | | | | | 250 | | | | | 255 | |

| Ala | Glu | Ser | Thr | Lys | Arg | Lys | Ala | Ala | Val | Trp | Pro | Leu | Gln | Ile | Ile |
|---|---|---|---|---|---|---|---|---|---|---|---|---|---|---|---|
| | | | 260 | | | | | 265 | | | | | 270 | | |

| Leu | Leu | Ile | Leu | Cys | Pro | Glu | Ile | Ile | Gln | Asp | Ile | Ser | Lys | Asp | Val |
|---|---|---|---|---|---|---|---|---|---|---|---|---|---|---|---|
| | | 275 | | | | | 280 | | | | | 285 | | | |

| Val | Asp | Glu | Asn | Asn | Met | Asn | Lys | Lys | Leu | Phe | Leu | Asp | Ser | Leu | Arg |
|---|---|---|---|---|---|---|---|---|---|---|---|---|---|---|---|
| | 290 | | | | | 295 | | | | | 300 | | | | |

| Lys | Ala | Leu | Ala | Gly | His | Gly | Gly | Ser | Arg | Gln | Leu | Thr | Glu | Ser | Ala |
|---|---|---|---|---|---|---|---|---|---|---|---|---|---|---|---|
| 305 | | | | | 310 | | | | | 315 | | | | | 320 |

| Ala | Ile | Ala | Cys | Val | Lys | Leu | Cys | Lys | Ala | Ser | Thr | Tyr | Ile |
|---|---|---|---|---|---|---|---|---|---|---|---|---|---|
| | | | | 325 | | | | | 330 | | | | |

( 2 ) INFORMATION FOR SEQ ID NO:7:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: group(28..34, 59..60)
        ( D ) OTHER INFORMATION: /note= "Consensus AG and lariat
            sequences"

( x i ) SEQUENCE DESCRIPTION: SEQ ID NO:7:

TATTTATGGT CGTTTTTAAG GATAAGCTGT TAACGTGTTT TTTTTTTCTT TTTTTTTCAG    60

( 2 ) INFORMATION FOR SEQ ID NO:8:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..84

( i x ) FEATURE:
        ( A ) NAME/KEY: misc_feature
        ( B ) LOCATION: (60 61)
        ( D ) OTHER INFORMATION: /note= "Position of the first
            splice junction separating exon 2 to the right and
            exon 1 to the left"

( x i ) SEQUENCE DESCRIPTION: SEQ ID NO:8:

| ATG | GCC | GCG | CAC | AGG | CCG | GTG | GAA | TGG | GTC | CAG | GCC | GTG | GTC | AGC | CGC | 48 |
| Met | Ala | Ala | His | Arg | Pro | Val | Glu | Trp | Val | Gln | Ala | Val | Val | Ser | Arg | |
| 335 | | | | 340 | | | | | 345 | | | | | 350 | | |

| TTC | GAC | GAG | CAG | CTT | CCA | ATA | AAA | ACA | GGA | CAG | CAG | 84 |
| Phe | Asp | Glu | Gln | Leu | Pro | Ile | Lys | Thr | Gly | Gln | Gln | |
| | | | | 355 | | | | | 360 | | | |

( 2 ) INFORMATION FOR SEQ ID NO:9:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Met | Ala | Ala | His | Arg | Pro | Val | Glu | Trp | Val | Gln | Ala | Val | Val | Ser | Arg |
| 1 | | | | 5 | | | | | 10 | | | | | 15 | |

| Phe | Asp | Glu | Gln | Leu | Pro | Ile | Lys | Thr | Gly | Gln | Gln |
| | | | | 20 | | | | | 25 | | |

( 2 ) INFORMATION FOR SEQ ID NO:10:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 19..60

( i x ) FEATURE:
        ( A ) NAME/KEY: misc_feature
        ( B ) LOCATION: 16..18
        ( D ) OTHER INFORMATION: /note= "In frame stop codon"

( x i ) SEQUENCE DESCRIPTION: SEQ ID NO:10:

| AGCCTCTTGT | GGCTTTGA | ATT | TTG | TTT | CAT | CAA | TTC | CTA | GGG | TTT | TGG | CAA | 51 |
| | | Ile | Leu | Phe | His | Gln | Phe | Leu | Gly | Phe | Trp | Gln | |
| | | | | 30 | | | | | 35 | | | | |

| CTT | CTC | CTG | 60 |
| Leu | Leu | Leu | |
| 40 | | | |

( 2 ) INFORMATION FOR SEQ ID NO:11:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| Ile | Leu | Phe | His | Gln | Phe | Leu | Gly | Phe | Trp | Gln | Leu | Leu | Leu |
| 1 | | | | 5 | | | | | 10 | | | | |

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
AGAGGCAAGG  AGAGGGTCTG  TG                                                    2 2
```

(2) INFORMATION FOR SEQ ID NO:13:

(i) SEQUENCE CHARACTERISTICS:
  (A) LENGTH: 18 amino acids
  (B) TYPE: amino acid
  (C) STRANDEDNESS: single
  (D) TOPOLOGY: linear (xi) SEQUENCE DESCRIPTION: SEQ ID NO:13:

```
Ala  Ser  Leu  Pro  Cys  Ser  Asn  Ser  Ala  Val  Phe  Met  Gln  Leu  Phe  Pro
 1                   5                        10                       15
His  Gln
```

(2) INFORMATION FOR SEQ ID NO:14:

(i) SEQUENCE CHARACTERISTICS:
  (A) LENGTH: 21 amino acids
  (B) TYPE: amino acid
  (C) STRANDEDNESS: single
  (D) TOPOLOGY: linear (xi) SEQUENCE DESCRIPTION: SEQ ID NO:14:

```
Ala  Thr  Cys  His  Ser  Leu  Leu  Asn  Lys  Ala  Thr  Val  Lys  Glu  Lys  Lys
 1                   5                        10                       15
Glu  Asn  Lys  Lys  Ser
               20
```